(12) United States Patent
Oh et al.

(10) Patent No.: US 12,016,915 B2
(45) Date of Patent: *Jun. 25, 2024

(54) AGENTS THAT ENGAGE ANTIGEN-PRESENTING CELLS THROUGH DENDRITIC CELL ASIALOGLYCOPROTEIN RECEPTOR (DC-ASGPR)

(71) Applicant: BAYLOR RESEARCH INSTITUTE, Dallas, TX (US)

(72) Inventors: SangKon Oh, Baltimore, MD (US); Dapeng Li, Davis, CA (US); Jacques Banchereau, Montclair, NJ (US); Gerard Zurawski, Midlothian, TX (US); Sandra Zurawski, Midlothian, TX (US)

(73) Assignee: BAYLOR RESEARCH INSTITUTE, Dallas, TX (US)

( * ) Notice: Subject to any disclaimer, the term of this patent is extended or adjusted under 35 U.S.C. 154(b) by 101 days.

This patent is subject to a terminal disclaimer.

(21) Appl. No.: 17/454,108

(22) Filed: Nov. 9, 2021

(65) Prior Publication Data

US 2022/0152192 A1    May 19, 2022

Related U.S. Application Data

(60) Continuation of application No. 16/372,832, filed on Apr. 2, 2019, now Pat. No. 11,173,202, which is a continuation of application No. 15/265,236, filed on Sep. 14, 2016, now Pat. No. 10,279,030, which is a continuation of application No. 14/254,206, filed on Apr. 16, 2014, now Pat. No. 9,453,074, which is a continuation of application No. 13/551,198, filed on Jul. 17, 2012, now Pat. No. 8,728,481, which is a division of application No. 12/025,010, filed on Feb. 2, 2008, now Pat. No. 8,236,934.

(60) Provisional application No. 60/888,036, filed on Feb. 2, 2007.

(51) Int. Cl.
| | |
|---|---|
| A61K 39/145 | (2006.01) |
| A61K 39/00 | (2006.01) |
| A61K 47/68 | (2017.01) |
| A61K 51/10 | (2006.01) |
| C07K 14/005 | (2006.01) |
| C07K 14/195 | (2006.01) |
| C07K 14/37 | (2006.01) |
| C07K 14/405 | (2006.01) |
| C07K 14/435 | (2006.01) |
| C07K 16/28 | (2006.01) |
| C12N 5/0784 | (2010.01) |
| C12N 7/00 | (2006.01) |

(52) U.S. Cl.
CPC ........ *A61K 39/145* (2013.01); *A61K 47/6849* (2017.08); *A61K 51/1027* (2013.01); *C07K 14/005* (2013.01); *C07K 14/195* (2013.01); *C07K 14/37* (2013.01); *C07K 14/405* (2013.01); *C07K 14/435* (2013.01); *C07K 16/28* (2013.01); *C12N 5/0639* (2013.01); *C12N 7/00* (2013.01); *A61K 2039/5154* (2013.01); *C07K 2317/24* (2013.01); *C07K 2317/33* (2013.01); *C07K 2317/56* (2013.01); *C07K 2317/74* (2013.01); *C07K 2317/75* (2013.01); *C07K 2317/92* (2013.01); *C12N 2760/16122* (2013.01); *C12N 2760/16134* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs |
| 3,949,064 A | 4/1976 | Bornstein |
| 4,174,384 A | 11/1979 | Ullman |
| 4,554,101 A | 11/1985 | Hopp |
| 5,738,985 A | 4/1998 | Miles et al. |
| 5,945,308 A | 8/1999 | Tang |
| 6,046,158 A | 4/2000 | Ariizumi |
| 6,277,959 B1 | 8/2001 | Valladeau |
| 6,410,241 B1 | 6/2002 | Sykes |
| 6,451,995 B1 | 9/2002 | Cheung |
| 6,541,011 B2 | 4/2003 | Punnonen |
| 6,738,985 B2 | 5/2004 | Hahn |
| 7,129,039 B2 | 10/2006 | Ariizumi |
| 7,179,595 B2 | 2/2007 | Li |
| 7,592,003 B2 | 9/2009 | Nagai |
| 7,666,596 B2 | 2/2010 | Halloran |
| 7,786,267 B2 | 8/2010 | Flamar |
| 8,236,934 B2 | 8/2012 | Banchereau et al. |
| 8,449,888 B2 | 5/2013 | Zurawski et al. |
| 8,481,314 B2 | 7/2013 | Banchereau et al. |
| 8,728,481 B2 | 5/2014 | Banchereau et al. |
| 9,339,556 B2 | 5/2016 | Banchereau et al. |

(Continued)

FOREIGN PATENT DOCUMENTS

| | | |
|---|---|---|
| EP | 1 418 234 | 5/2004 |
| EP | 1 441 030 | 7/2004 |

(Continued)

OTHER PUBLICATIONS

Accession No. NP_498023, Nov. 2008, pp. 1-2.

(Continued)

*Primary Examiner* — Amy E Juedes
(74) *Attorney, Agent, or Firm* — Norton Rose Fulbright US LLP

(57) ABSTRACT

The present invention includes compositions and methods for making and using anti DC-ASGPR antibodies that can, e.g., activate DCs and other cells.

7 Claims, 12 Drawing Sheets

Figure 1A:
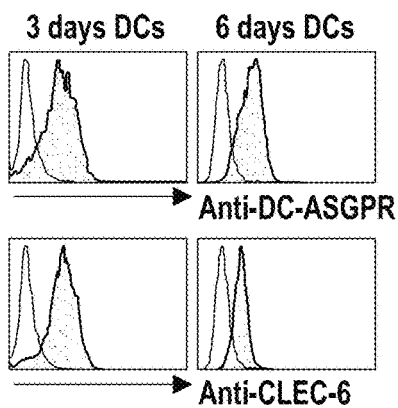
Figure 1B:
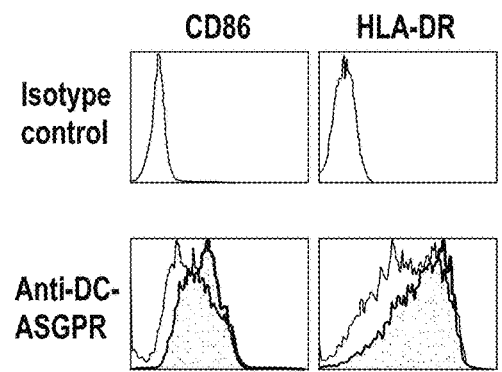

Specification includes a Sequence Listing.

(56) References Cited

U.S. PATENT DOCUMENTS

| | | |
|---|---|---|
| 9,453,074 B2 | 9/2016 | Oh et al. |
| 2002/0055618 A1 | 5/2002 | Landridge et al. |
| 2004/0126357 A1 | 7/2004 | Segal |
| 2004/0192892 A1 | 9/2004 | Valladeau et al. |
| 2004/0258688 A1 | 12/2004 | Hawiger et al. |
| 2004/0265901 A1 | 12/2004 | Li |
| 2005/0037001 A1 | 2/2005 | Germeraad |
| 2005/0064509 A1 | 3/2005 | Bradbury |
| 2005/0106700 A1 | 5/2005 | Nomura et al. |
| 2006/0257412 A1 | 11/2006 | Bowdish |
| 2006/0269949 A1 | 11/2006 | Halloran |
| 2008/0233140 A1 | 9/2008 | Banchereau et al. |
| 2008/0254044 A1 | 10/2008 | Zurawski |
| 2009/0186025 A1 | 7/2009 | Colaco |
| 2012/0039916 A1 | 2/2012 | Zurawski et al. |
| 2012/0121592 A1 | 5/2012 | Oh et al. |
| 2012/0231023 A1 | 9/2012 | Zurawski et al. |
| 2012/0237513 A1 | 9/2012 | Zurawski et al. |
| 2012/0244155 A1 | 9/2012 | Lecine et al. |
| 2012/0282281 A1 | 11/2012 | Banchereau et al. |
| 2012/0301465 A1 | 11/2012 | Dutartre et al. |
| 2012/0315269 A1 | 12/2012 | Klechevsky et al. |
| 2016/0375126 A1 | 12/2016 | Oh et al. |

FOREIGN PATENT DOCUMENTS

| | | |
|---|---|---|
| FR | 2748479 | 11/1997 |
| JP | 2000-157282 | 6/2000 |
| JP | 2004-236504 | 8/2004 |
| WO | WO 1997/14789 | 4/1997 |
| WO | WO 00/063251 | 10/2000 |
| WO | WO 2000/63151 | 10/2000 |
| WO | WO 2002/035242 | 5/2002 |
| WO | WO 2003/036895 | 5/2003 |
| WO | WO 2003/073827 | 9/2003 |
| WO | WO 2006/004663 | 1/2006 |
| WO | WO 2006/107617 | 10/2006 |
| WO | WO 2008/097817 | 8/2008 |

OTHER PUBLICATIONS

Ahmad-Nejad, et al., "Bacterial CpG-DNA and Lipopolysaccharides Activate Toll-Like Receptors at Distinct Cellular Compartments," European J. Immunol., (2002), 32:1958-1968.

Arce, Ignacio et al., "The human C-type lectin CLECSF18 is a novel monocyte/macrophage endocytic receptor", European Journal of Immunology, 2004, vol. 34(1 ), pp. 210-220.

Asea, A., et al., "HSP70 Stimulates Cytokine Production Through a CD14-Dependant Pathway, Demonstrating its Dual Role as a Chaperone and Cytokine," Nat Med, (2000), 6:435-442.

Balazs, F., et al., "Blood Dendritic Cells Interact with Splenic Marginal Zone B Cells to Initiate T-Independent Immune Responses," Immunity, (2002), 17:341-352.

Balch, et al., *J Biol Chem*. 273(29): 18656-64, 1998.

Banchereau J., et al., "Immune and Clinical Responses in Patients with Metastatic Melanoma to CD34(+) Progenitor-Derived Dendritic Cell Vaccine," Cancer Res, (2001), 61(17):6451-8.

Banchereau, J., et al., "Dendritic Cells and the Control of Immunity," Nature, (1998), 392:245-252.

Banchereau, J., et al., "Dendritic Cells as Vectors for Thereapy," Cell, (2001), 106(3):271-4.

Banchereau, J., et al., "Immunobiology of Dendritic Cells," Annu Rev Immunol, (2000), 18:767-811.

Barak, Y. et al., "Matching Fusion Protein Systems for Affinity Analysis of Two Interacting Families of Proteins: the Cohesin-Dockerin Interaction", J. Mo. Recognit, 2005:18:491-501.

Barrios, et al., "Length of the Antibody Heavy Chain Complementarity Determining Region 3 as a Specificity-Determining Factor", J. Mol. Recognit. 2004: 17:332-338.

Bates, E. E., et al., "APCs Express DCIR, a Novel C-Type Lectin Surface Receptor Containing an Immunoreceptor Tyrosine-Based Inhibitory Motif," J Immunol, (1999), 163(4):1973-83.

Bausinger, H., et al., "Endotoxin-Free Heat-Shock Protein 70 Fails to Induce APC Activation," Eur J Immunol (2002), 32:3708-3713.

Bayer, et al., *Trends Biotechnol*. 12: 379-386, 1994.

Bendsten, J.D., et al., "Improved Prediction of Signal Peptides: SignaiP 3.0." J Mol Bioi, (2004), 340(4):783-95.

Berard, F., et al., "Cross-Priming of Naive CDS T Cells Against Melanoma Antigens Using Dendritic Cells Loaded with Killed Allogeneic Melanoma Cells," J Exp Med, (Dec. 2000), 192(11):1535-44.

Bergtold, A., et al., "Cell Surface Recycling of Internalized Antigen Permits Dendritic Cell Priming of B Cells," Immunity (2005), 23:503-514.

Bernasconi, N. L., et al., "Maintenance of Serological Memory by Polyclonal Activation of Human Memory B Cells," Science (2002), 298:2199-2202.

Beutler, B., et al., "Genetic Analysis of Host Resistance: Toll-Like Receptor Signaling and Immunity at Large," Annu Rev Immunol (2006), 24:353-389.

Bonifaz, L.C., et al., "In Vivo Targeting of Antigens to Maturing Dendritic Cells via the DEC-205 Receptor Improves T Cell Caccination" J Exp Med, (Mar. 2004), 199(6):815-24.

Bonifaz, Laura, et al., "Efficient Targeting of Protein Antigen to the Dendritic Cell Receptor DEC-205 in the Steady 8 State Leads to Antigen Presentation on Major Histocompatibility Complex Class I Products and Peripheral CD8 T Cell D Tolerance," J. Exp. Med., Dec. 16, 2002, vol. 196, No. 12, pp. 1627-1638.

Brown, G. D., "Dectin-1: a signalling non-TLR pattern-recognition receptor," Nat Rev Immunol (2006), 6:33-43.

Burgdorf et al., *J Immunol*. 176:6770-6, 2006.

Cambi, A., et al., "The C-type lectin DC-SIGN (CD209) is an antigenuptake receptor for Candida albicans on dendritic cells," Eur J Immunol (2003), 33:532-538.

Carter, et al., "Preferential Induction of CD4+ T Cell Responses through In Vivo Targeting of Antigen to Dendritic Cell-Associated C-Type Lectin-1", J. of Immunol., vol. 177, No. 4, 2006, pp. 2276-2284.

Carvalho, A.L., et al., "Cellulosome Assembly Reveal by the Crystal Structure of the Cohesin-Dockerin Complex." Proc Natl Acad Sci USA, (2003), 100(24):13809-14.

Chu. et al., "CpG Oligodeoxynucleotides Down-Regulate Macrophage Class II MHC Antigen Processing", J Immunol 1999:163:1188-1194.

Colonna, M., et al., "Molecular Characterization of Two Novel C-Type Lectin-Like Receptors, one of which is Selectively Expressed in Human Dendritic Cells," Eur J Immunol (2000), 30:697-704.

Cooper, A.M., et al., "Mice Lacking Bioactive IL-12 Can Generate Protective, Antigen-Specific Cellular Responses to Mycobacterial Infection Only if the IL-12 p40 Subunit Is Present," J Immunol (2002), 168:1322-1327.

Craig et al., 2006, J. Biotech. vol. 121: 165-173.

Craxton, A., et al., "Macrophage and Dendritic Cell-Dependent Regulation of Human B-Cell Proliferation Requires the TNF Family Ligand BAFF," Blood, (2003), 101:4464-4471.

Daly, et al., *Anal Lett*. 34:1799-1827, 2001.

Deineste, Y., G et al., "Involvement of LOX-1 in Dendritic Cell-Mediated Antigen Cross-Presentation." Immunity (2002), 17(3):353-62.

Deyev, S.M. et al., "Design of multivalent complexes using the barnase-barstar module", Nature Biotechnology, vol. 21, No. 12, Dec. 2003, pp. 1486-1492.

Ding, et al., "A Scaffoldin of the Bacteriodes cellulosolvens Celluslosome That Contains 11 Type II Cohesins", J. Bacteriology 182(17):4915-4925, Sep. 2000.

Ding, et al., "The Bacterial Scaffoldin: Structure, Function and Potential Applications in the Nanosciences", Genetic Engineering, vol. 25:209-225, (2003).

D'Ostiani, C. F., et al., "Dendritic Cells Discriminate between Yeasts and Hyphae of the Fungus *Candida albicans*: Implications for Initiation ofT Helper Cell Immunity In Vitro and In Vivo," J Exp Med {2000), 191:1661-1673.

Dubois, B., et al., "Dendritic cells directly modulate B cell growth and differentiation," J Leukoc Bioi (1999), 66:224-230.

Engering, et al., *Trends Immunol*. 23(10): 480-5, 2002.

(56) References Cited

OTHER PUBLICATIONS

Extended European Search Report for Application No. 08714180.0, dated Sep. 29, 2011, 14 pages.
European Search Report for Application No. 08728767.8, dated Aug. 24, 2010, 11 pages.
Extended European Search Report for Application No. 08799678.1, dated Feb. 5, 2010, 12 pages.
Fierobe, H-P et al., "Design and Production of Active Cellulosome Chimeras," J Bioi Chem (2001 ), 276:21257-21261.
Figdor, C. G., et al., "C-Type Lectin Receptors on Dendritic Cells and Langerhans Cells," Nat Rev Immunol, (2002), 2{2}: 77-84.
Flamar, A.L. et al., "Antibody and Antigen Complexes Based on Cohesin and Dockerin Interaction are Versatile Tools for Eliciting and Monitoring Specific Immune Responses", Clinical Immunology, US Lnkd-DOI:1 0.1016/J. D Clim.2009.03.019, vol. 131, Jan. 1, 2009, pp. S9.
Flomes, L.M. et al., "Identification of Lectin-Like Receptors Expressed by Antigen Presenting Cells and Neutrophils and their Mapping to a Novel Gene Complex," Immunogenetics, (2004), vol. 56, pp. 506-517.
Fradin, C., et al., "~-1 ,2-Linked Oligomannosides from Candida albicans Bind to a 32-Kilodalton Macrophage Membrane Protein Homologous to the Mammalian Lectin Galectin-3," Infect Immun (2000), 68:4391-4398.
Frankel, A. F., "Increased Sophistication of Immunotoxins," Clin Can Res, {2002), 8:942-944.
Gantner, B. N., et al., "Collaborative Induction of Inflammatory Responses by Dectin-1 and Toll-like Receptor 2," J Exp Med (2003), 197:1107-1117.
Geijtenbeek, T. B., et al., "DC-SIGN-ICAM-2 Interaction Mediates Dendritic Cell Trafficking," Nat Immunol {2000), 1:353-357.
Geijtenbeek, T. B., et al., "Identification of DC-SIGN, a Novel Dendritic Cell-Specific ICAM-3 Receptor that Supports Primary Immune Responses," Cell (2000), 100:575-585.
Geijtenbeek, T. B., et al., "Mycobacteria Target DC-SIGN to Suppress Dendritic Cell Function," J Exp Med (2003), 197:7-17.
Geijtenbeek, T.B., et al., "Self-and Nonself-Recognition by C-type Lectins on Dendritic Cells." Annu Rev Immunol (2004), 22:33-54.
Gross, J. A., et al., "TACI and BCMA are Receptors for a TNF Homologue Implicated in B-cell Autoimmune Disease," Nature (2000), 404:995-999.
Grueneback, et al., "Human {h) Dectin-1 is a Member of C-Type-Lectin-Like Receptor Family that was Shown to be the Major Receptor for Fungal Beta-Giucans . . . " Abstract from 49th Annual Meeting of the American Society of Dematology, Dec. 2007, XP002563205, 2 pages.
Hayashida, K., et al., "Lectin-Like Oxidized LDL Receptor-1 (LOX-1) Supports Adhesion of Mononuclear Leukocytes and a Monocyte-Like Cell Line THP-1 Cells Under Static and Flow Conditions," FEBS Letters, (2002), 511:133-138.
Huang, et al., "Cloning and Characterization of a Novel ITIM Containing Lectin-like Immunoreceptor LLIR and Its Two Transmembrane Region Deletion Variants", Biochem. Biophys. Res. Commun., 281(1):131-140, (2001).
International search Report and Written Opinion for PCT/US08/52865, dated Aug. 13, 2008, 8 pages.
International Search Report and Written Opinion for PCT/US2008/052714, dated Jul. 8, 2008, 8 pages.
International Search Report and Written Opinion for PCT/US2008/054785, dated Sep. 25, 2008, 12 pages.
International Search Report and Written Opinion for PCT/US2008/054792, dated Aug. 13, 2008, 10 pages.
International Search Report and Written Opinion for PCT/US2008/054798, dated Dec. 8, 2008, 13 pages.
International Search Report and Written Opinion for PCT/US2008/52850, dated Sep. 24, 2008, 9 pages.
Janeway, et al., Immunobiol. 3:3-3: 4, 1997.
Jeannin, P., et al., "Complexity and Complementarity of Outer Membrane Protein A Recognition by Cellular and Humoral Innate Immunity Receptors," Immunity (2005), 22:551-560.
Jego, G., et al., "Plasmacytoid Dendritic Cells Induce Plasma Cell Differentiation through Type I Interferon and Interleukin 6," Immunity (2003), 19:225-234.
Jiang, W., et al., Nature, 375, pp. 151-155, May 11, 1995.
Jindou, S. et al., "Interaction between a Type-11 Dockerin Domain and a Type-11 Cohesin Domain from Clostridium thermocellum Cellulosome", Biosci. Biotechnol. Biochem. 68(4):924-926,(2004).
Kakutani, M., et al., "A platelet-endothelium interaction mediated by lectin-like oxidized low-density lipoprotein receptor-1," PNAS (2000), 97:360-364.
Karni et al., Journal of Immunology vol. 177: 4196-4202, 2006.
Karpol, A. et al., "Engineering a Reversible, High-Affinity System for Efficient Protein Purification Based on the Cohesin-Dockerin Interaction", J. Mol. Recognit. 2009, vol. 22:91-98.
Kikuchi, T., et al., "Dendritic Cells Genetically Modified to Express CD40 Ligand and Pulsed with Antigen can Initiate Antigen-Specific Humoral Immunity Independent of CD4+ T Cells," Nat Med, (2000), 6:1154-1159.
Klimka et al., "Human Anti-CD30 Recombinant Antibodies by Guided Phage Antibody Selection Using Cell Planning", Brit. J. Cancer, vol. 83, 252-260, 2000.
Kobrin, et al., "A V Region Mutation in a Phosphocholine-Bindng Monoclonal Antibody Results in Loss of Antigen Binding", J. Immunology, 146:2017-2020 (1991).
Latz, et al., "TLR9 Signals After Translocating from the ER to CpG DNA in the Lysosome", Nat. Immunol., (2004), vol. 5:190-198.
Lee, S. J., et al., "Mannose Receptor-Mediated Regulation of Serum Glycoprotein Homeostasis," Science (2002), 295:1898-1901.
Li, et al., "Targeting Self and Foreign Antigens to Dendritic Cells Via DC-ASGPR Generates IL-10-Producing Suppressive CD4+T Cells," J. Exp. Med., 209: 109-121, 2012.
Li, et al., Clin Exp Immunol. 162:251-61, 2010.
Luft, et al., International Immunology 14(4):367-380, 2002.
Ma, "Genome-Wide Analysis of Human Peripheral Leukocyte Gene Expression," PhD Thesis, p. 51 & 60, 2003.
Maclennan, C., et al., "Dendritic Cells, BAFF, and APRIL: Innate Players in Adaptive Antibody Responses," Immunity (2002), 17:235-238.
Maeda, N., et al., "The Cell Surface Receptor DC-SIGN Discriminates between Mycobacterium Species through Selective Recognition of the Mannose Caps on Lipoarabinomannan," J Bioi Chern, (2003), 278:5513-5513.
Marks et al., "By-Passing Immunization: Human Antibodies from V-gene Libraries Displayed on Phage", J. Mol. Bioi., (1991), 222:581-597.
Mechaly, A. et al., "Cohesin-Dockerin Interaction in Cellulosome Assembly", J. Biological Chemistry, Mar. 30, 2001, vol. 276, No. 13, pp. 9883-9888.
Mehta et al., "Lectin-like, oxidized low-density lipoprotein receptor-1 (LOX-1): a critical player in the development of atherosclerosis and related disorders", Cardiovasc. Res., 69:36-45, 2006.
Mellman, I. et al., "Dendritic Cells: Specialized and Regulated Antigen Processing Machines," Cell, (2001), 106 (3):255-8.
Moore, P. A., et al., "BLyS: Member of the Tumor Necrosis Factor Family and B Lymphocyte Stimulator," Science (1999), 285:260-263.
Moriwaki, H., et al., "Expression of Lectin-Like Oxidized Low Density Lipoprotein Receptor-1 in Human and Murine Macrophages: Upregulated Expression by TN F-a," FEBS Letters, (1998), 440:29-32.
Neidhardt-Berard, E.M., et al., "Dendritic Cells Loaded with Killed Breast Cancer Cells Induce Differentiation of Tumor-Specific Cytotoxic T Lymphocytes" Breast Cancer Res, (2004), 6(4):R322-8.
Netea, M.G., et al., "CD40/CD40 Ligand Interactions in the Host Defense Against Disseminated Candida Albicans Infection: the Role of Macrophage-Derived Nitric Oxide," Eur J Immunol, (2002), 32:1455-1463.
Office Communication in Israeli Patent Application No. 224539 dated Apr. 23, 2013.
Palucka, A.K., et al., "Human Dendritic Cell Subsets in NOD/SCID Mice Engrafted with CD34+ Hematopoieticprogenitors," Blood, (2003), 102(9):3302-1 0.

(56) References Cited

OTHER PUBLICATIONS

Proudfoot et al., "Receptor-Mediated Delivery of Antigens to Dendritic Cells: Anticancer Applications", Molec. Pharm., vol. 4, 2007, pp. 58-72.
Pyz, E., et al., "C-Type Lectin-Like Receptors on Myeloid Cells," Ann Med, (2006), 38:242-251.
Q1, H., et al., "Extrafollicular Activation of Lymph Node B Cells by Antigen-Bearing Dendritic Cells," Science (2006), 312:1672-1676.
Ramakrishna, et al., "Toll-like Receptor Activation Enhances Cell-Mediated Immunity Inducted by an Antibody Vaccine Targeting Human Dendritic Cells", Journal of Translational Medicine, vol. 5:5, pp. 1-14, Jan. 2007.
Ramakrishna, V., et al., "Mannose Receptor Targeting of Tumor Antigen PMEL 17 to Human Dendritic Cells Directs Antimelanoma T Cell Responses via Multiple HLA Molecules" J Immunol, (2004), 172(5):2845-52.
Reddy, M.P., et al., "Elimination of FC Receptor-Dependent Effector Functions of a Modified lgG4 Monoclonal Antibody to Human CD4," J Immunol ,(2000), 164(4):1925-33.
Riemer, et al., *Mol Immunol*. 42: 1121-4, 2005.
Rocca-Serra, et al., *Nature*. 304:353-355, 1983.
Rose, et al., *J. Immunol*. MRC1 mannose receptor, C type 1 [*Homo sapiens*], 1999, http://www.ncbi.nlm.nih.gov/gene/4360.
Rossi, E.A. et al., "Development of New Multivalent-bispecific Agents for Pretargeting Tumor Localization and Therapy", Clinical Cancer Research, vol. 9, Sep. 1, 2003, pp. 3886S-3896S.
Ruprecht, C. R., et al., "Toll-like Receptor Stimulation as a Third Signal Required for Activation of Human Naive B Cells," Eur J Immunol, (2006), 36:810-816.
Saeland, S., "Langerin and the DC Asialoglycoprotein Receptor: Two Closely Related Endocytic Type-11 Lectins with Divergent Functions in Dendritic Cells," Journal of Investigative Dermatology, vol. 117, No. 4, Oct. 2001, p. 1003.
Sagoo, et al., "Regulatory T Cells and Therapeutic Cells," Curr. Opn. Organ Transplant, 13:645-653, 2008.
Schaft, Neils, et al., "Dendritic Cell Vaccination and Other Strategies to Tip the Balance of the Immune System," Cancer Immunol. Immunother, (2008), 57:913-928.
Shortman, Ken, et al., "Mouse and Human Dendritic Cell Subtypes," Nature Reviews, Immunology, vol. 2, Mar. 2002, pp. 454-465.
Smith, Daniel C., et al., "Lack of Dendritic Cell Maturation by the Plant Toxin Ricin," European J. Immunol., (2004), 34:2149-2157.
Spooner, RA, et al., "Expression of Immunoglobulin Heavy Chain-Ricin a Chain Fusions in Mammalian Cells," Mol. Immunol., Feb. 1994, 31(2):117-125.
Stancovski, et al., *PNAS*. 88:8691-5, 1991.
Starovasnik, Melissa A., et al., "Structural Mimicry of a Native Protein by a Minimized Binding Domain," Proc. Nat. Acad. Sci. USA, Sep. 1997, vol. 94, pp. 10080-10085.
Steinman, "In vitro production of antigen-activated dendritic cell precursor for use as an immunogen in a vaccine; application in juvenile diabetes, multiple sclerosis, myasthenia gravis and atopic dermatitis therapy", Vaccine, 12(5):478, 1994.
Steinman, Ralph M., et al., "Active Immunization Against Cancer with Dendritic Cells: The Near Future," Int. J. Cancer, {2001), 94, 459-473.
Tacken, Paul J., et al., "Effective Induction of Naive and Recall T-Cell Responses by Targeting Antigen to Human Dendritic Cells via a Humanized Anti-DC-SIGN Antibody," Blood, May 5, 2005, 106:1278-1285.
Tailleux, L., et al., "DC-SIGN Is the Major *Mycobacterium tuberculosis* Receptor on Human Dendritic Cells," J Exp Med (2003), 197:121-127.
Tan, et al., "Mannose Receptor-Mediated Uptake of Antigens Strongly Enhances HLA Class 11-Restricted Antigen Presentation by Cultured Dendritic Cells," Eur. J. Immunol., 1997, 27:2426-2435.
Trombetia, E. Sergio, et al., "Cell Biology of Antigen Processing in Vitro and In Vivo," Annu. Rev. Immunol., 2005, 23:975-1028.
Trumpfheller, Christine, et al., "Intensified and Protective CD4+ T Cell Immunity in Mice with Anti-Dendritic Cell HIV Gag Fusion Antibody Vaccine," Mar. 20, 2006, vol. 203, No. 3, pp. 607-617.
Valladeau, J., et al., "Immature Human Dendritic Cells Express Asialoglycoprotein Receptor Isoforms for Efficient Receptor-Mediated Endocytosis," J Immunol (2001), 167:5767-5774.
Wang, Y., et al., "CD40 Is a Cellular Receptor Mediating Mycobacterial Heat Shock Protein 70 Stimulation of CC—Chemokines," Immunity (2001), 15:971-983.
Wiley, K.N., et al., "The In-Vitro Inhibition of Rat Alloantigen Presentation by Immunotoxins—IMplications for Allografting," Clin. Exp. Immunol., (1989), 76:132-137.
Wykes, M. N., et al., "Dendritic cell-8-cell interaction: dendritic cells provide B cells with CD40-independent proliferation signals and CD40-dependent survival signals," Immunology (2000), 100:1-3.
Wykes, M. N., et al., "Dendritic cells and follicular dendritic cells express a novel ligand for CD38 which influences their maturation and antibody responses," Immunology (2004), 113:318-327.
Xie et al., "Generation of Anti-LOX-1 Cytotoxic T Lymphocytes by AAV Manipulation of Dendritic Cells towards Preventing Atheosclerosis", *Mol. Ther*., 11(Suppl. 1):S362-S363, 2005.
Zhu, Zhenping, et al., "Inhibition of Tumor Growth and Metastasis by Targeting Rumor-Associated Angiogenesis with Antagonists to the Receptors of Vascular Endothelial Growlh Factor," Investigational New Drugs, 1999, 17:195-212.
Zhu, Zhenping, et al., "Inhibition of Tumor Growth and Metastasis by Targeting Rumor-Associated Angiogenesis with Antagonists to the Receptors of Vascular Endothelial Growth Factor," Investigational New Drugs, 1999, 17:195-212.
Zymosan, Dectin-1 Review, "A Major Receptor in Antifungal Immunity" 2008.

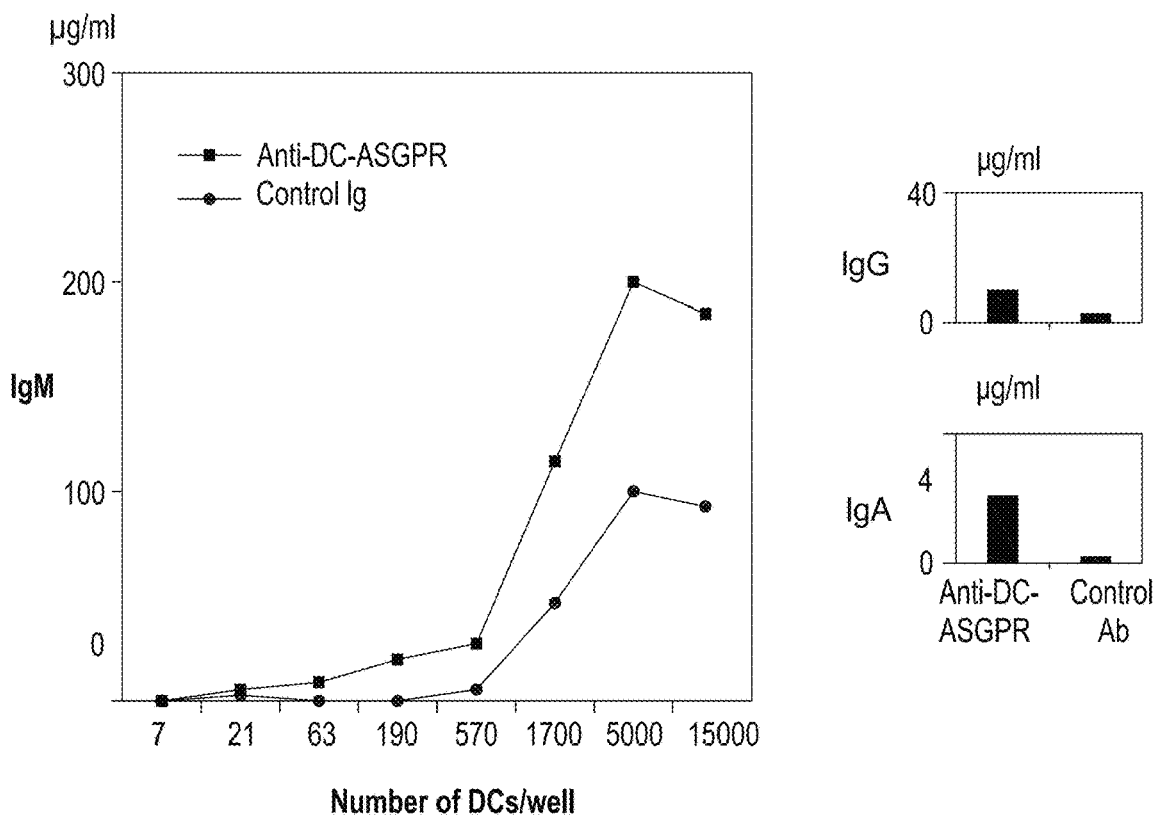
FIG. 2B
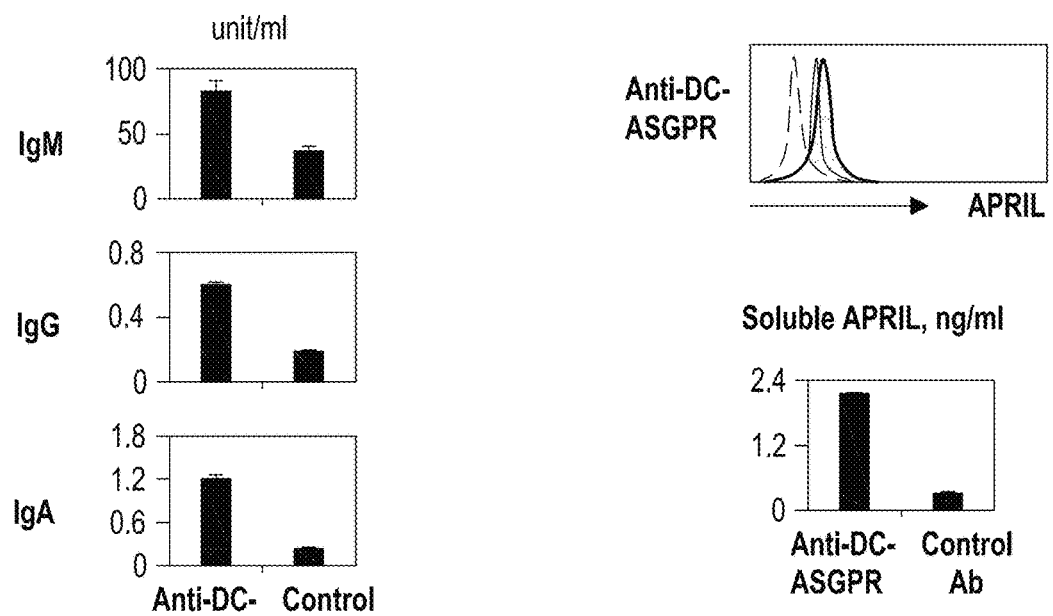
FIG. 2C
FIG. 2D

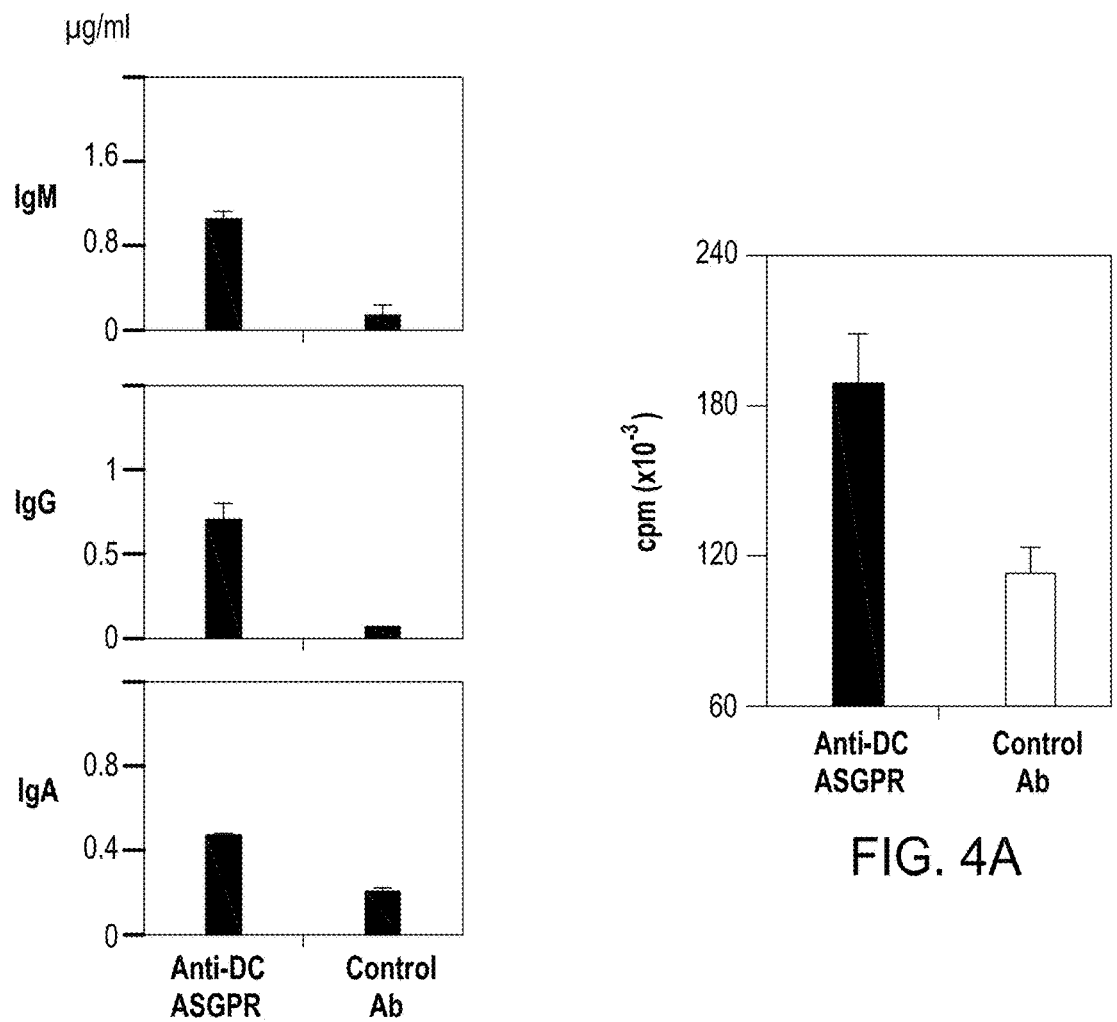
FIG. 3D
FIG. 4A
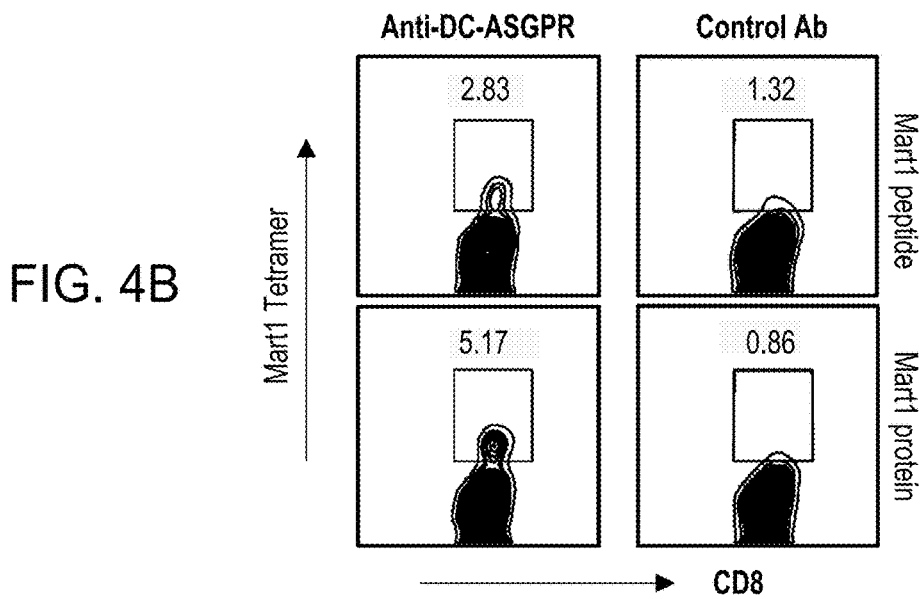
FIG. 4B

SEQUENCE LISTING

<160> NUMBER OF SEQ ID NOS: 17

<210> SEQ ID NO 1
<211> LENGTH: 9

```
<212> TYPE: PRT
<213> ORGANISM: Artificial
<220> FEATURE:
<223> OTHER INFORMATION: Chemically Synthesized Peptide

<400> SEQUENCE: 1

Gly Ile Leu Gly Phe Val Phe Thr Leu
1               5

<210> SEQ ID NO 2
<211> LENGTH: 10
<212> TYPE: PRT
<213> ORGANISM: Artificial
<220> FEATURE:
<223> OTHER INFORMATION: Chemically Synthesized Peptide

<400> SEQUENCE: 2

Glu Leu Ala Gly Ile Gly Ile Leu Thr Val
1               5                   10

<210> SEQ ID NO 3
<211> LENGTH: 186
<212> TYPE: DNA
<213> ORGANISM: Artificial
<220> FEATURE:
<223> OTHER INFORMATION: Chemically Synthesized Oligonucleotide

<400> SEQUENCE: 3
gacaccaccg aggcccgcca ccccaccccc ccgtgaccac ccccaccac caccgaccgg     60 aagggcacca ccgccgagga gctggccggc atcggcatcc tgaccgtgat cctgggcggc    120
aagcggacca caacagcac ccccaccaag ggcgaattct gcagatatcc atcacactgg   180
cggccg                                                               186

<210> SEQ ID NO 4
<211> LENGTH: 61
<212> TYPE: PRT
<213> ORGANISM: Artificial
<220> FEATURE:
<223> OTHER INFORMATION: Chemically Synthesized Peptide

<400> SEQUENCE: 4

Asp Thr Thr Glu Ala Arg His Pro His Pro Pro Val Thr Thr Pro Thr
1               5                   10                  15

Thr Asp Arg Lys Gly Thr Thr Ala Glu Glu Leu Ala Gly Ile Gly Ile
            20                  25                  30

Leu Thr Val Ile Leu Gly Gly Lys Arg Thr Asn Asn Ser Thr Pro Thr
        35                  40                  45

Lys Gly Glu Phe Cys Arg Tyr Pro Ser His Trp Arg Pro
    50                  55                  60

<210> SEQ ID NO 5
<211> LENGTH: 446
<212> TYPE: PRT
<213> ORGANISM: Artificial
<220> FEATURE:
<223> OTHER INFORMATION: Chemically Synthesized Peptide

<400> SEQUENCE: 5

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30
```

Tyr Ser Trp His Trp Ile Arg Gln Phe Pro Gly Asn Lys Leu Glu Trp
            35                  40                  45
Met Gly Tyr Ile Leu Phe Ser Gly Ser Thr Asn Tyr Asn Pro Ser Leu
 50                  55                  60
Lys Ser Arg Ile Ser Ile Thr Arg Asp Thr Ser Lys Asn Gln Phe Phe
 65                  70                  75                  80
Leu Gln Leu Asn Ser Val Thr Thr Glu Asp Thr Ala Thr Tyr Phe Cys
                85                  90                  95
Ala Arg Ser Asn Tyr Gly Ser Phe Ala Ser Trp Gly Gln Gly Thr Leu
            100                 105                 110
Val Thr Val Ser Ala Ala Lys Thr Thr Gly Pro Ser Val Phe Pro Leu
            115                 120                 125
Ala Pro Cys Ser Arg Ser Thr Ser Glu Ser Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
            195                 200                 205
Thr Lys Val Asp Lys Arg Val Glu Ser Lys Tyr Gly Pro Pro Cys Pro
            210                 215                 220
Pro Cys Pro Ala Pro Glu Phe Glu Gly Gly Pro Ser Val Phe Leu Phe
225                 230                 235                 240
Pro Pro Lys Pro Lys Asp Thr Leu Met Ile Ser Arg Thr Pro Glu Val
            245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
            275                 280                 285
Arg Glu Glu Gln Phe Asn Ser Thr Tyr Arg Val Val Ser Val Leu Thr
290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
            355                 360                 365
Phe Tyr Pro Ser Asp Ile Ala Val Glu Trp Glu Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly Lys Ala Ser
            435                 440                 445

```
<210> SEQ ID NO 6
<211> LENGTH: 213
<212> TYPE: PRT
<213> ORGANISM: Artificial
<220> FEATURE:
<223> OTHER INFORMATION: Chemically Synthesized Peptide

<400> SEQUENCE: 6

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser His Met
            20                  25                  30

His Trp Tyr Gln Gln Lys Ser Gly Thr Ser Pro Lys Arg Trp Ile Tyr
        35                  40                  45

Asp Thr Ser Arg Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser His Pro Trp Ser
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 7
<211> LENGTH: 449
<212> TYPE: PRT
<213> ORGANISM: Artificial
<220> FEATURE:
<223> OTHER INFORMATION: Chemically Synthesized Peptide

<400> SEQUENCE: 7

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Val Pro Gly Lys Gly Leu Arg Trp Met
        35                  40                  45

Gly Trp Met Asp Thr Phe Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Ser Leu Lys Asn Glu Asp Thr Ala Thr Tyr Phe Cys
                85                  90                  95
```

Ala Arg Gly Gly Ile Leu Arg Leu Asn Tyr Phe Asp Tyr Trp Gly Gln
            100                 105                 110

Gly Thr Thr Leu Thr Val Ser Ser Ala Lys Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Ala
        435                 440                 445

Ser

<210> SEQ ID NO 8
<211> LENGTH: 214
<212> TYPE: PRT
<213> ORGANISM: Artificial
<220> FEATURE:
<223> OTHER INFORMATION: Chemically Synthesized Peptide

<400> SEQUENCE: 8

Asp Ile Gln Met Thr Gln Ser Ser Ser Ser Phe Ser Val Ser Leu Gly

```
            1               5                   10                  15
Asp Arg Val Thr Ile Thr Cys Lys Ala Ser Glu Asp Ile Tyr Asn Arg
                20                  25                  30

Leu Gly Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
            50                  55                  60

Ser Gly Ser Gly Lys Asp Tyr Ala Leu Ser Ile Thr Ser Leu Gln Thr
65                  70                  75                  80

Glu Asp Leu Ala Thr Tyr Tyr Cys Gln Gln Cys Trp Thr Ser Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 9
<211> LENGTH: 445
<212> TYPE: PRT
<213> ORGANISM: Artificial
<220> FEATURE:
<223> OTHER INFORMATION: Chemically Synthesized Peptide

<400> SEQUENCE: 9

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Tyr Met Lys Trp Val Lys Gln Ser His Gly Lys Ser Leu Glu Trp Ile
            35                  40                  45

Gly Asp Ile Asn Pro Asn Tyr Gly Asp Thr Phe Tyr Asn Gln Lys Phe
            50                  55                  60

Glu Gly Lys Ala Thr Leu Thr Val Asp Lys Ser Ser Arg Thr Ala Tyr
65                  70                  75                  80

Met Gln Leu Asn Ser Leu Thr Ser Glu Asp Ser Ala Val Tyr Tyr Cys
                85                  90                  95

Gly Arg Gly Asp Tyr Gly Tyr Phe Asp Val Trp Gly Ala Gly Thr Thr
            100                 105                 110

Val Thr Val Ser Ser Ala Lys Thr Lys Gly Pro Ser Val Phe Pro Leu
            115                 120                 125

Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser Trp Asn Ser
```

```
                145                 150                 155                 160
Gly Ala Leu Thr Ser Gly Val His Thr Phe Pro Ala Val Leu Gln Ser
                    165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                    245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                    325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                    405                 410                 415

Gly Asn Val Phe Ser Cys Ser Val Met His Glu Ala Leu His Asn His
                420                 425                 430

Tyr Thr Gln Lys Ser Leu Ser Leu Gly Lys Ala Ser
            435                 440                 445

<210> SEQ ID NO 10
<211> LENGTH: 214
<212> TYPE: PRT
<213> ORGANISM: Artificial
<220> FEATURE:
<223> OTHER INFORMATION: Chemically Synthesized Peptide

<400> SEQUENCE: 10

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Asn Asn Val Gln Ser
```

```
            65                  70                  75                  80
Glu Asp Leu Ala Asp Tyr Phe Cys Gln Gln Tyr Ser Ser Asn Pro Tyr
                    85                  90                  95

Met Phe Gly Gly Gly Thr Lys Leu Glu Ile Lys Arg Thr Val Ala Ala
                100                 105                 110

Pro Ser Val Phe Ile Phe Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 11
<211> LENGTH: 447
<212> TYPE: PRT
<213> ORGANISM: Artificial
<220> FEATURE:
<223> OTHER INFORMATION: Chemically Synthesized Peptide

<400> SEQUENCE: 11

Gln Leu Gln Gln Ser Gly Pro Glu Leu Val Lys Pro Gly Ala Ser Val
1               5                   10                  15

Lys Ile Ser Cys Lys Thr Ser Gly Tyr Thr Phe Thr Glu Tyr Thr Met
                20                  25                  30

His Trp Val Arg Gln Ser His Gly Lys Ser Leu Glu Trp Ile Gly Gly
            35                  40                  45

Ile Asn Pro Ile Asn Gly Gly Pro Thr Tyr Asn Gln Lys Phe Lys Gly
        50                  55                  60

Lys Ala Thr Leu Thr Val Asp Lys Ser Ser Thr Ala Tyr Met Glu
65                  70                  75                  80

Leu Arg Ser Leu Thr Ser Glu Asp Ser Ala Val Tyr Tyr Cys Ala Arg
                    85                  90                  95

Trp Asp Tyr Gly Ser Arg Asp Val Met Asp Tyr Trp Gly Gln Gly Thr
                100                 105                 110

Ser Val Thr Val Ser Ser Ala Lys Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                    165                 170                 175

Ser Ser Gly Leu Tyr Ser Leu Ser Ser Val Val Thr Val Pro Ser Ser
                180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
```

-continued

```
                210                 215                 220
Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Asp Val Ser Gln Glu Asp Pro Glu Val Gln
        260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys Ala Ser
        435                 440                 445

<210> SEQ ID NO 12
<211> LENGTH: 214
<212> TYPE: PRT
<213> ORGANISM: Artificial
<220> FEATURE:
<223> OTHER INFORMATION: Chemically Synthesized Peptide

<400> SEQUENCE: 12

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Arg Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Thr Tyr Ser Tyr Ile Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
            130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 13
<211> LENGTH: 780
<212> TYPE: PRT
<213> ORGANISM: Artificial
<220> FEATURE:
<223> OTHER INFORMATION: Chemically Synthesized Peptide

<400> SEQUENCE: 13

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Ile Asn Pro Asn Tyr Gly Asp Thr Phe Tyr Asn Gln Lys Phe
    50                  55                  60

Glu Gly Lys Ala Thr Leu Thr Val Asp Lys Ser Ser Arg Thr Ala Tyr
65                  70                  75                  80

Met Gln Leu Asn Ser Leu Thr Ser Glu Asp Ser Ala Val Tyr Tyr Cys
                85                  90                  95

Gly Arg Gly Asp Tyr Gly Tyr Phe Asp Val Trp Gly Ala Gly Thr Thr
            100                 105                 110

Val Thr Val Ser Ser Ala Lys Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
```

```
                275                 280                 285
Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys Ala Ser Asp Thr
                435                 440                 445

Thr Glu Pro Ala Thr Pro Thr Thr Pro Val Thr Thr Asp Gln Ile Cys
450                 455                 460

Ile Gly Tyr His Ala Asn Asn Ser Thr Glu Gln Val Asp Thr Ile Met
465                 470                 475                 480

Glu Lys Asn Val Thr Val Thr His Ala Gln Asp Ile Leu Glu Lys Lys
                485                 490                 495

His Asn Gly Lys Leu Cys Asp Leu Asp Gly Val Lys Pro Leu Ile Leu
                500                 505                 510

Arg Asp Cys Ser Val Ala Gly Trp Leu Leu Gly Asn Pro Met Cys Asp
                515                 520                 525

Glu Phe Ile Asn Val Pro Glu Trp Ser Tyr Ile Val Glu Lys Ala Asn
530                 535                 540

Pro Val Asn Asp Leu Cys Tyr Pro Gly Asp Phe Asn Asp Tyr Glu Glu
545                 550                 555                 560

Leu Lys His Leu Leu Ser Arg Ile Asn His Phe Glu Lys Ile Gln Ile
                565                 570                 575

Ile Pro Lys Ser Ser Trp Ser Ser His Glu Ala Ser Leu Gly Val Ser
                580                 585                 590

Ser Ala Cys Pro Tyr Gln Gly Lys Ser Ser Phe Phe Arg Asn Val Val
                595                 600                 605

Trp Leu Ile Lys Lys Asn Ser Thr Tyr Pro Thr Ile Lys Arg Ser Tyr
610                 615                 620

Asn Asn Thr Asn Gln Glu Asp Leu Leu Val Leu Trp Gly Ile His His
625                 630                 635                 640

Pro Asn Asp Ala Ala Glu Gln Thr Lys Leu Tyr Gln Asn Pro Thr Thr
                645                 650                 655

Tyr Ile Ser Val Gly Thr Ser Thr Leu Asn Gln Arg Leu Val Pro Arg
                660                 665                 670

Ile Ala Thr Arg Ser Lys Val Asn Gly Gln Ser Gly Arg Met Glu Phe
                675                 680                 685

Phe Trp Thr Ile Leu Lys Pro Asn Asp Ala Ile Asn Phe Glu Ser Asn
690                 695                 700
```

-continued

Gly Asn Phe Ile Ala Pro Glu Tyr Ala Tyr Lys Ile Val Lys Lys Gly
705                 710                 715                 720

Asp Ser Thr Ile Met Lys Ser Glu Leu Glu Tyr Gly Asn Cys Asn Thr
            725                 730                 735

Lys Cys Gln Thr Pro Met Gly Ala Ile Asn Ser Ser Met Pro Phe His
        740                 745                 750

Asn Ile His Pro Leu Thr Ile Gly Glu Cys Pro Lys Tyr Val Lys Ser
    755                 760                 765

Asn Arg Leu Val Leu Ala His His His His His
770                 775                 780

<210> SEQ ID NO 14
<211> LENGTH: 521
<212> TYPE: PRT
<213> ORGANISM: Artificial
<220> FEATURE:
<223> OTHER INFORMATION: Chemically Synthesized Peptide

<400> SEQUENCE: 14

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile Leu Phe Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Phe Cys
                85                  90                  95

Ala Arg Ser Asn Tyr Gly Ser Phe Ala Ser Trp Gly Gln Gly Thr Leu
            100                 105                 110

Val Thr Val Ser Ala Ala Lys Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Ala Ser Asn Ser
        435                 440                 445

Pro Gln Asn Glu Val Leu Tyr Gly Asp Val Asn Asp Asp Gly Lys Val
    450                 455                 460

Asn Ser Thr Asp Leu Thr Leu Leu Lys Arg Tyr Val Leu Lys Ala Val
465                 470                 475                 480

Ser Thr Leu Pro Ser Ser Lys Ala Glu Lys Asn Ala Asp Val Asn Arg
                485                 490                 495

Asp Gly Arg Val Asn Ser Ser Asp Val Thr Ile Leu Ser Arg Tyr Leu
            500                 505                 510

Ile Arg Val Ile Glu Lys Leu Pro Ile
        515                 520

<210> SEQ ID NO 15
<211> LENGTH: 68
<212> TYPE: DNA
<213> ORGANISM: Artificial
<220> FEATURE:
<223> OTHER INFORMATION: Chemically Synthesized Oligonucleotide

<400> SEQUENCE: 15
gaattcgcta gccaccatga catatgaaaa cttccaagac ttggagagtg aggagaaagt    60
ccaagggg                                                             68

<210> SEQ ID NO 16
<211> LENGTH: 62
<212> TYPE: DNA
<213> ORGANISM: Artificial
<220> FEATURE:
<223> OTHER INFORMATION: Chemically Synthesized Oligonucleotide

<400> SEQUENCE: 16
cgaattcgcg gccgctcagt gactctcctg gctggcctgg gtcagaccag cctcgcagac    60
cc                                                                   62

<210> SEQ ID NO 17
<211> LENGTH: 62
<212> TYPE: DNA
<213> ORGANISM: Artificial

```
<220> FEATURE:
<223> OTHER INFORMATION: Chemically Synthesized Oligonucleotide

<400> SEQUENCE: 17
gggtctgcga ggctggtctg acccaggcca gccaggagag tcactgagcg gccgcgaatt    60
cg                                                                    62
```

AGENTS THAT ENGAGE ANTIGEN-PRESENTING CELLS THROUGH DENDRITIC CELL ASIALOGLYCOPROTEIN RECEPTOR (DC-ASGPR)

CROSS-REFERENCE TO RELATED APPLICATIONS

This application is a continuation of U.S. patent application Ser. No. 16/372,832, filed Apr. 2, 2019, which is a continuation of U.S. patent application Ser. No. 15/265,236, filed Sep. 14, 2016, now U.S. Pat. No. 10,279,030, issued May 7, 2019, which is a continuation application of U.S. patent application Ser. No. 14/254,206, filed Apr. 16, 2014, now U.S. Pat. No. 9,453,074, issued Sep. 27, 2016, which is a continuation application of U.S. patent application Ser. No. 13/551,198, filed Jul. 17, 2012, now U.S. Pat. No. 8,728,481, issued May 20, 2014, which is a divisional of U.S. patent application Ser. No. 12/025,010 filed Feb. 2, 2008, now U.S. Pat. No. 8,236,934, issued Aug. 7, 2012, which claims priority to U.S. Provisional Application Ser. No. 60/888,036, filed Feb. 2, 2007, the contents of each of which are incorporated by reference herein in their entirety.

STATEMENT OF FEDERALLY FUNDED RESEARCH

This invention was made with government support under Grant No. U19 A1057234 awarded by the National Institutes of Health (NIH). The government has certain rights in the invention.

TECHNICAL FIELD OF THE INVENTION

The present invention relates in general to the field of agents that engage antigen-presenting cells through dendritic cell asialoglycoprotein receptor (DC-ASGPR).

REFERENCE TO A SEQUENCE LISTING

The present application includes a Sequence Listing filed separately as required by 37 CFR 1.821-1.825.

BACKGROUND OF THE INVENTION

Without limiting the scope of the invention, its background is described in connection with antigen presentation.

Dendritic Cells play a pivotal role in controlling the interface of innate and acquired immunity by providing soluble and intercellular signals, followed by recognition of pathogens. These functions of DCs are largely dependent on the expression of specialized surface receptors, 'pattern recognition receptors' (PRRs), represented, most notably, by toll-like receptors (TLRs) and C-type lectins or lectin-like receptors (LLRs) (1-3).

In the current paradigm, a major role of TLRs is to alert DCs to produce interleukin 12 (IL-12) and other inflammatory cytokines for initiating immune responses. C-type LLRs operate as constituents of the powerful antigen capture and uptake mechanism of macrophages and DCs (1). Compared to TLRs, however, LLRs might have broader ranges of biological functions that include cell migrations (4), intercellular interactions (5). These multiple functions of LLRs might be due to the facts that LLRs, unlike TLRs, can recognize both self and non-self. However, the complexity of LLRs, including the redundancy of a number of LLRs expressed in immune cells, has been one of the major obstacles to understand the detailed functions of individual LLRs. In addition, natural ligands for most of these receptors remain unidentified. Nonetheless, evidence from recent studies suggests that LLRs, in collaboration with TLRs, may contribute to the activation of immune cells during microbial infections (6-14).

Valladeau et al. (The Journal of Immunology, 2001, 167: 5767-5774) described a novel LLR receptor on immature human Dendritic Cells related to hepatic Asialoglycoprotein Receptor and demonstrated that it efficiently mediated endocytosis. DC-ASGPR mRNA was observed predominantly in immune tissues—in DC and granulocytes, but not in T, B, or NK cells, or monocytes. DC-ASGPR species were restricted to the CD14-derived DC obtained from CD34-derived progenitors, while absent from the CD1a-derived subset. Both monocyte-derived DC and tonsillar interstitial-type DC expressed DC-ASGPR protein, while Langerhans-type cells did not. Furthermore, DC-ASGPR was a feature of immaturity, as expression was lost upon CD40 activation. In agreement with the presence of tyrosine-based and dileucine motifs in the intracytoplasmic domain, mAb against DC-ASGPR was rapidly internalized by DC at 37° C. Finally, intracellular DC-ASGPR was localized to early endosomes, suggesting that the receptor recycles to the cell surface following internalization of ligand. These findings identified DC-ASGPR/human macrophage lectin as a feature of immature DC, and as another lectin important for the specialized Ag-capture function of DC.

SUMMARY OF THE INVENTION

While DC-ASGPR is known to be capable of directing the internalization of surrogate antigen into human DC, the invention uses novel biological activities of DC-ASGPR to effect particularly desirable changes in the immune system, some in the context of antigen uptake (e.g., vaccination), others through the unique action of DC-ASGPR effectors (alone or in concert with other immune regulatory molecules) capable of eliciting signaling through this receptor on DC, B cells, and monocytes. The invention disclosure reveals means of developing unique agents capable of activating cells bearing DC-ASGPR, as well as the effect of the resulting changes in cells receiving these signals regards action on other cells in the immune system. These effects (either alone, or in concert with other signals (i.e., co-stimulation)) are highly predictive of therapeutic outcomes for certain disease states or for augmenting protective outcomes in the context of vaccination.

The present invention includes compositions and methods for increasing the effectiveness of antigen presentation by a DC-ASGPR-expressing antigen presenting cell by isolating and purifying a DC-ASGPR-specific antibody or fragment thereof to which a targeted agent is attached that forms an antibody-antigen complex, wherein the agent is processed and presented by, e.g., a dendritic cell, that has been contacted with the antibody-agent complex. In one embodiment, the antigen presenting cell is a dendritic cell and the DC-ASGPR-specific antibody or fragment thereof is bound to one half of a Coherin/Dockerin pair. The DC-ASGPR-specific antibody or fragment thereof may also be bound to one half of a Coherin/Dockerin pair and an antigen is bound to the complementary half of the Coherin/Dockerin pair to form a complex. Non-limiting examples agents include one or more peptides, proteins, lipids, carbohydrates, nucleic acids and combinations thereof.

The agent may one or more cytokine selected from interleukins, transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors, B/T-cell differentiation factors, B/T-cell growth factors, mitogenic cytokines, chemotactic cytokines, colony stimulating factors, angiogenesis factors, IFN-α, IFN-β, IFN-γ, III, IL2, IL3, IL4, IL5, IL6, IL7, IL8, IL9, IL10, IL11, IL12, IL13, IL14, IL15, IL16, IL17, IL18, etc., leptin, myostatin, macrophage stimulating protein, platelet-derived growth factor, TNF-α, TNF-β, NGF, CD40L, CD137L/4-1BBL, human lymphotoxin-β, G-CSF, M-CSF, GM-CSF, PDGF, IL-1α, IL1-β, IP-10, PF4, GRO, 9E3, erythropoietin, endostatin, angiostatin, VEGF, transforming growth factor (TGF) supergene family include the beta transforming growth factors (for example TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB). In another embodiment, the agent comprises an antigen that is a bacterial, viral, fungal, protozoan or cancer protein.

The present invention also includes compositions and methods for increasing the effectiveness of antigen presentation by dendritic cells comprising binding a DC-ASGPR-specific antibody or fragment thereof to which an antigen is attached that forms an antibody-antigen complex, wherein the antigen is processed and presented by a dendritic cell that has been contacted with the antibody-antigen complex. Another embodiment is the use of antibodies or other specific binding molecules directed to DC-ASGPR for delivering antigens to antigen-presenting cells for the purpose of eliciting protective or therapeutic immune responses. The use of antigen-targeting reagents specific to DC-ASGPR for vaccination via the skin; antigen-targeting reagents specific to DC-ASGPR in association with co-administered or linked adjuvant for vaccination or use for antigen-targeting (vaccination) purposes of specific antigens which can be expressed as recombinant antigen-antibody fusion proteins.

Another embodiment includes a method for increasing the effectiveness of dendritic cells by isolating patient dendritic cells; exposing the dendritic cells to activating amounts of anti-DC-ASGPR antibodies or fragments thereof and antigen to form antigen-loaded, activated dendritic cells; and reintroducing the antigen-loaded, activated dendritic cells into the patient. The antigen may be a bacterial, viral, fungal, protozoan or cancer protein. The present invention also includes an anti-DC-ASGPR immunoglobulin or portion thereof that is secreted from mammalian cells and an antigen bound to the immunoglobulin. The immunoglobulin is bound to one half of a cohesin/dockerin domain, or it may also include a complementary half of the cohesin-dockerin binding pair bound to an antigen that forms a complex with the modular rAb carrier, or a complementary half of the cohesin-dockerin binding pair that is a fusion protein with an antigen. The antigen specific domain may be a full length antibody, an antibody variable region domain, an Fab fragment, a Fab' fragment, an $F(ab)_2$ fragment, and Fv fragment, and Fabc fragment and/or a Fab fragment with portions of the Fc domain. The anti-DC-ASGPR immunoglobulin may also be bound to a toxin selected from wherein the toxin is selected from the group consisting of a radioactive isotope, metal, enzyme, botulin, tetanus, ricin, cholera, diphtheria, aflatoxins, perfringens toxin, mycotoxins, shigatoxin, staphylococcal enterotoxin B, T2, seguitoxin, saxitoxin, abrin, cyanoginosin, alphatoxin, tetrodotoxin, aconotoxin, snake venom and spider venom. The antigen may be a fusion protein with the immunoglobulin or bound chemically covalently or not.

The present invention also includes compositions and methods for increasing the effectiveness of dendritic cells by isolating patient dendritic cells, exposing the dendritic cells to activating amounts of anti-DC-ASGPR antibodies or fragments thereof and antigen to form antigen-loaded, activated dendritic cells; and reintroducing the antigen-loaded, activated dendritic cells into the patient. The agents may be used to engage DC-ASGPR, alone or with co-activating agents, to activate antigen-presenting cells for therapeutic or protective applications, to bind DC-ASGPR and/or activating agents linked to antigens, alone or with co-activating agents, for protective or therapeutic vaccination. Another use of is the development of specific antibody V-region sequences capable of binding to and activating DC-ASGPR, for use as anti-DC-ASGPR agents linked to toxic agents for therapeutic purposes in the context of diseases known or suspected to result from inappropriate activation of immune cells via DC-ASGPR and as a vaccine with a DC-ASGPR-specific antibody or fragment thereof to which an antigen is attached that forms an antibody-antigen complex, wherein the antigen is processed and presented by a dendritic cell that has been contacted with the antibody-antigen complex.

BRIEF DESCRIPTION OF THE DRAWINGS

For a more complete understanding of the features and advantages of the present invention, reference is now made to the detailed description of the invention along with the accompanying figures and in which:

Figure 1C:
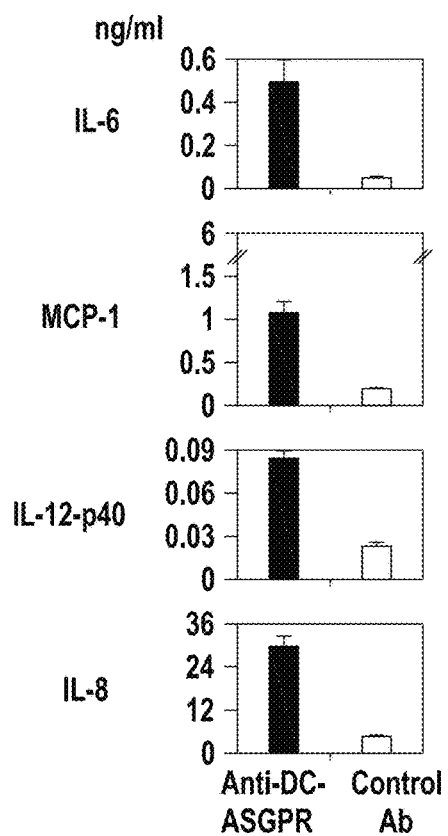
Figure 1D:
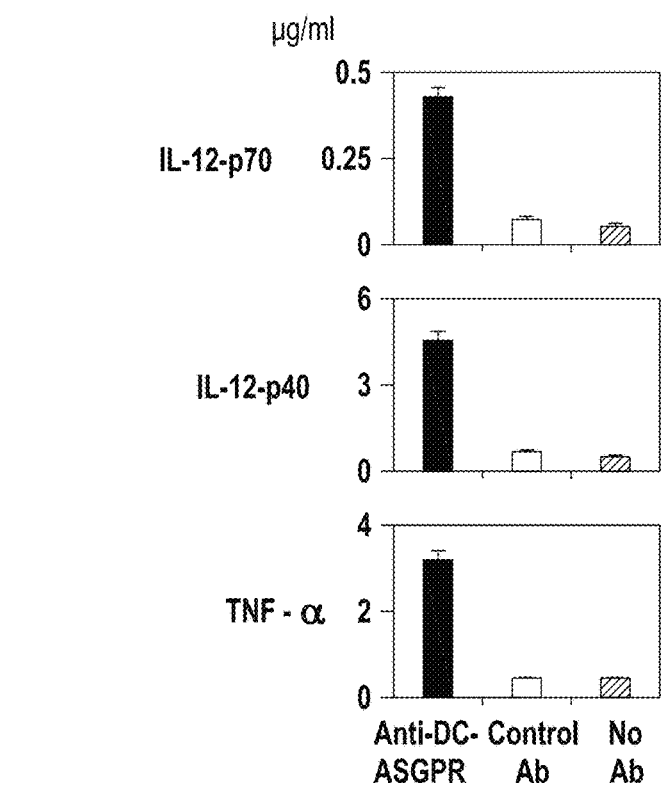
Figure 2A:
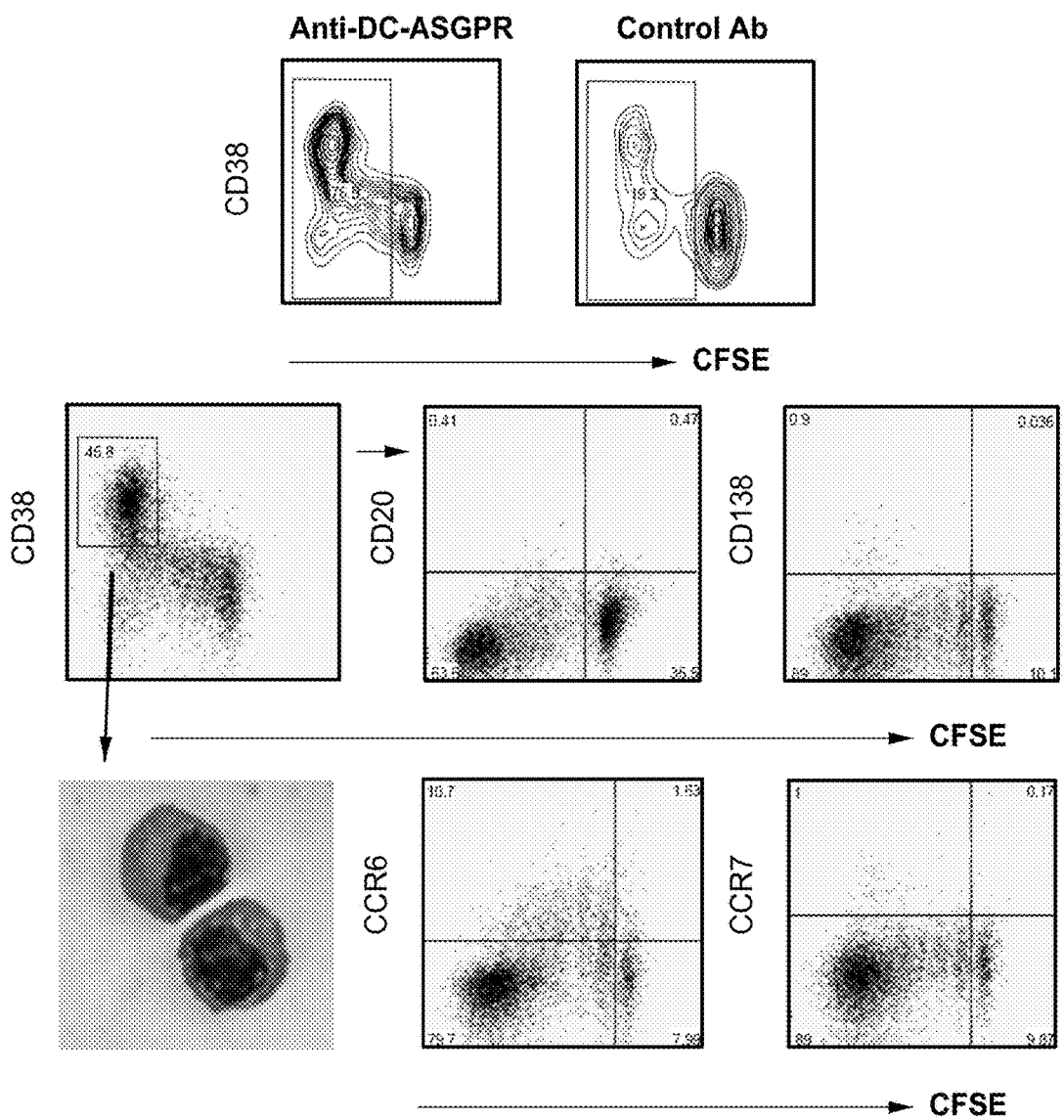

FIGS. 1A to 1E demonstrate signaling through lectin-like receptor DC-ASGPR activates DCs, resulting in increased levels of costimulatory molecules as well as cytokines and chemokines. FIG. 1A shows three day and six day GM/IL-4 DCs were stained with FITC-labeled goat anti-mouse IgG followed by mouse monoclonal anti-human DC-ASGPR, antibody. FIG. 1B shows six day GM/IL-4 DCs were cultured in plates coated with the anti-DC-ASGPR or control mAbs (1-2 ug/ml) for 16-18 h. Cells were stained with anti-CD86 and HLA-DR antibodies labeled with fluorescent dyes. Open and filled bars in the histograms represent cells activated with isotype control mAbs and anti-lectin mAbs, respectively. FIG. 1C shows six day GM/IL-4 DCs were cultured in plates coated with the mAbs for 12 h, and subjected to RNA isolation and Affymetrix Gene Chip analysis, as described in Methods. Fold increases of gene expression by anti-lectin mAbs were compared with the gene expression levels in DCs stimulated with control mAbs. FIG. 1D shows the cytokines and chemokines in the culture supernatants from the experiment shown in FIG. 1B were measured by Luminex. FIG. 1E shows six day GM/IL-4 DCs were cultured in plates coated with mAbs in the presence or absence of 50 ng/ml soluble CD40L, for 16-18 h, and then stained with anti-CD83 antibodies. Cytokines and chemokines in the culture supernatants from the experiment shown in FIG. 1E were measured by Luminex. Results shown are representative of three independent experiments using cells from different normal donors.

FIGS. 2A to 2D shows that DC-ASGPR expressed on DCs, contributes to enhanced humoral immune responses. Six day GM/IL-4 DCs, $5\times10^3$/well, were incubated in 96 well plates coated with anti-DC-ASGPR or control mAb for 16-18 h, and then 1×10$^5$ autologous CD19$^+$ B cells stained with CFSE were co-cultured in the presence of 20 units/ml IL-2 and 50 nM CpG. FIG. 2A is a FACS of day six cells stained with fluorescently labeled antibodies. CD3+ and 7-AAD$^+$ cells were gated out. CD38$^+$ and CFSE$^-$ cells were purified by FACS sorter and Giemsa staining was performed. FIG. 2B are culture supernatants on day thirteen were analyzed for total IgM, IgG, and IgM by sandwich ELISA. FIG. 1C shows DCs pulsed with 5 multiplicity of infection (moi) of heat-inactivated influenza virus (PR8), and cultured with B cells. Culture supernatant was analyzed for influenza-specific immunoglobulins (Igs) on day thirteen. FIG. 1D shows DC cultured with anti-DC-ASGPR or control mAb were stained for cell surface APRIL expression and the supernatants assayed for soluble APRIL.

Figure 3A:
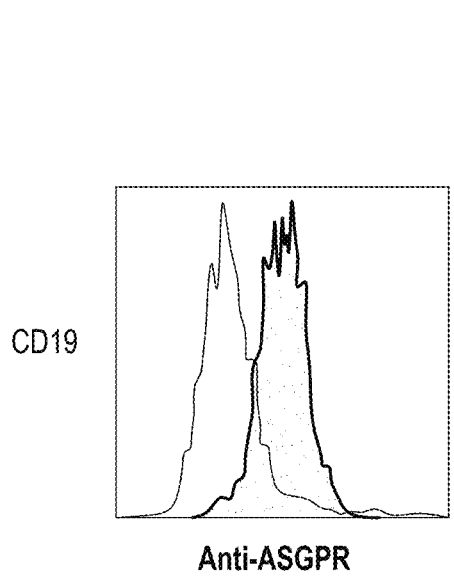
Figure 3B:
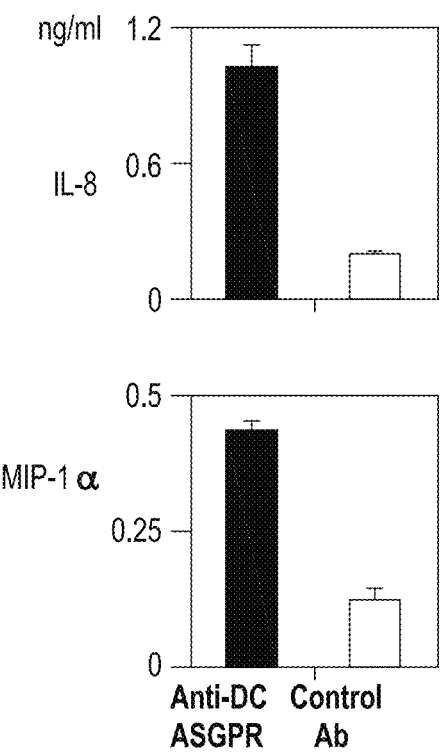
Figure 3C:
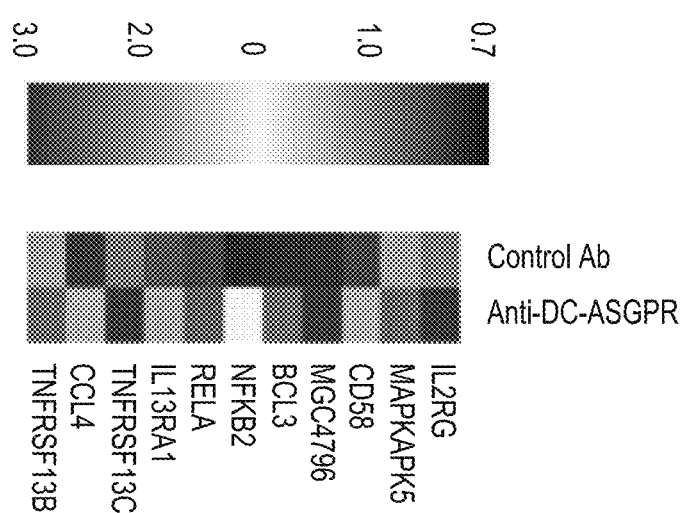

FIGS. 3A to 3D shows the cell surface expression of DC-ASGPR on B cells contribute to B cell activation and immunoglobulin production. FIG. 3A are PBMCs from buffy coats were stained with anti-CD19, anti-CD3, and anti-DC-ASGPR or control mAb. CD19$^+$ and CD3$^+$ cells were gated and the expression levels of the molecules on CD19$^+$ B cells were measured by flow cytometry. FIG. 3B are CD19$^+$ B cells from buffy coats were cultured in plates coated with the mAbs for 12 h, and subjected to RNA isolation and Affymetrix Gene Chip analysis as described in Methods. Fold increases of gene expression by anti-DC-ASGPR mAb were compared to the gene expression levels in CD19$^+$ B cells stimulated with control mAb. FIG. 3C shows CD19$^+$ B cells were cultured in plates coated with the mAbs for 16-18 h, and then culture supernatants were analyzed for cytokines and chemokines by Luminex. FIG. 3D shows 1×10$^5$ CD19$^+$ B cells were cultured in plates coated with the mAbs for thirteen days. Total Ig levels were measured by ELISA. Data are representative of two repeat experiments using cells from three different normal donors.

FIGS. 4A to 4D shows that the proliferation of purified allogeneic T cells was significantly enhanced by DCs stimulated with mAb specific for DC-ASGPR.

Figure 5:
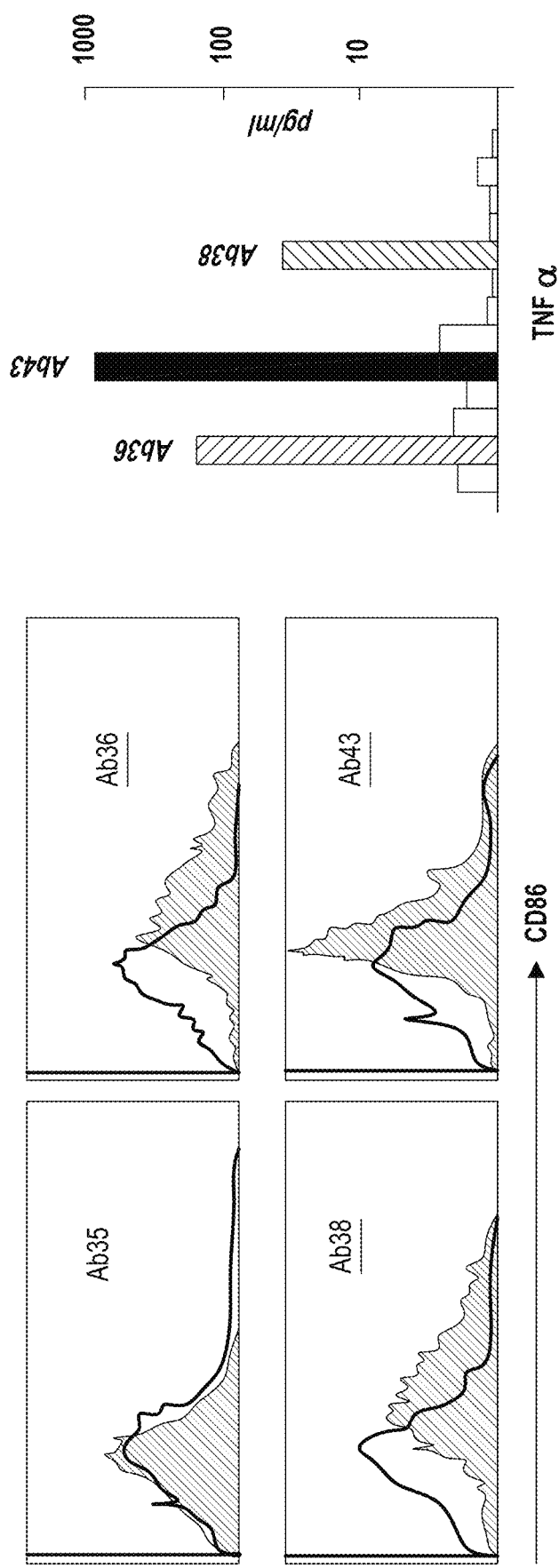

FIG. 5 shows that certain anti-DC-ASGPR mAbs can activate DC. GM-CSF/IL-4. DC were incubated for 24 hrs with one of a panel of 12 pure anti-ASGPR mAbs. Cells were then tested for expression of cell surface CD86 (a DC activation marker) and supernatants were assayed for secreted cytokines. Three mAbs (36, 38, 43) from the anti-ASGPR mAb panel activated DC.

Figure 6:
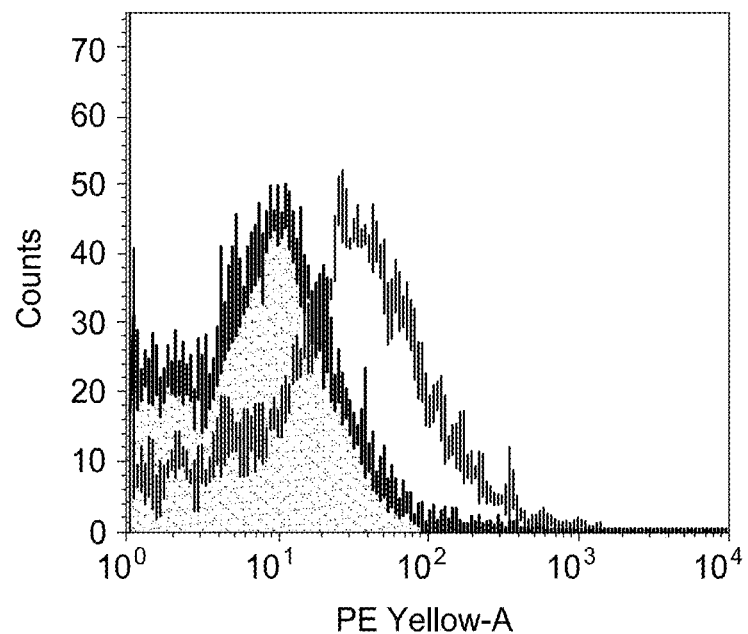

FIG. 6 shows that different antigens can be expressed in the context of a DC-ASGPR rAb. Such an anti-DC-ASGPR rAb.Doc protein can be simply mixed with any Cohesin.fusion protein to assemble a stable non-covalent [rAb.Doc:Coh.fusion] complex that functions just as a rAb.fusion protein.

Figure 7:
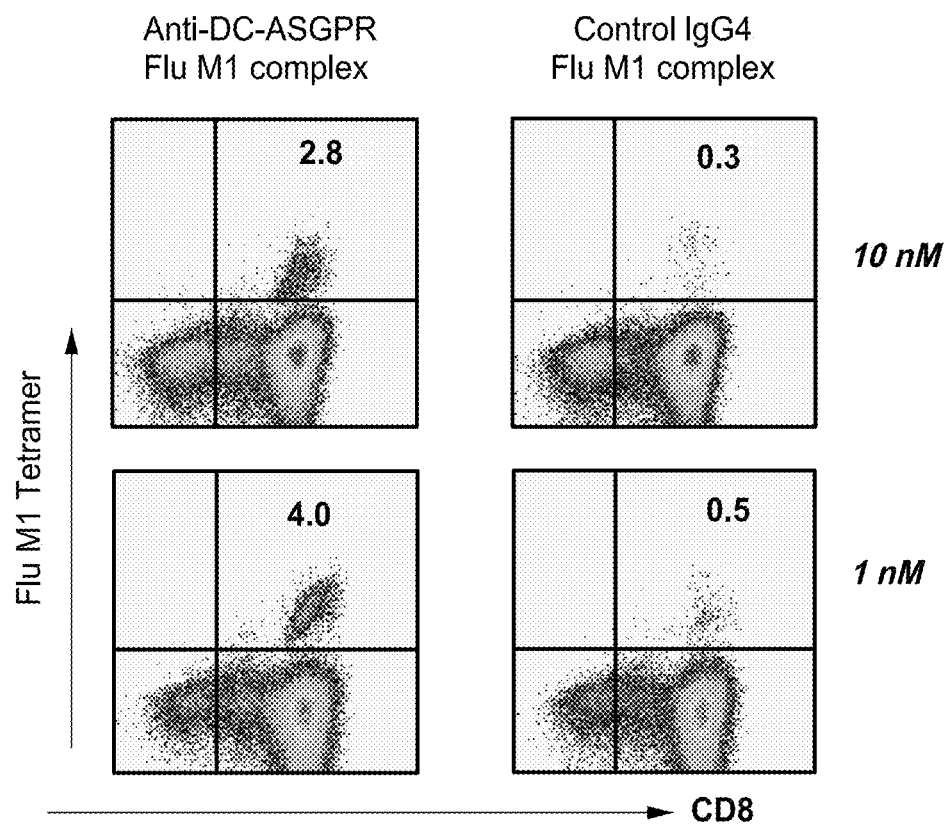
Figure 8A:
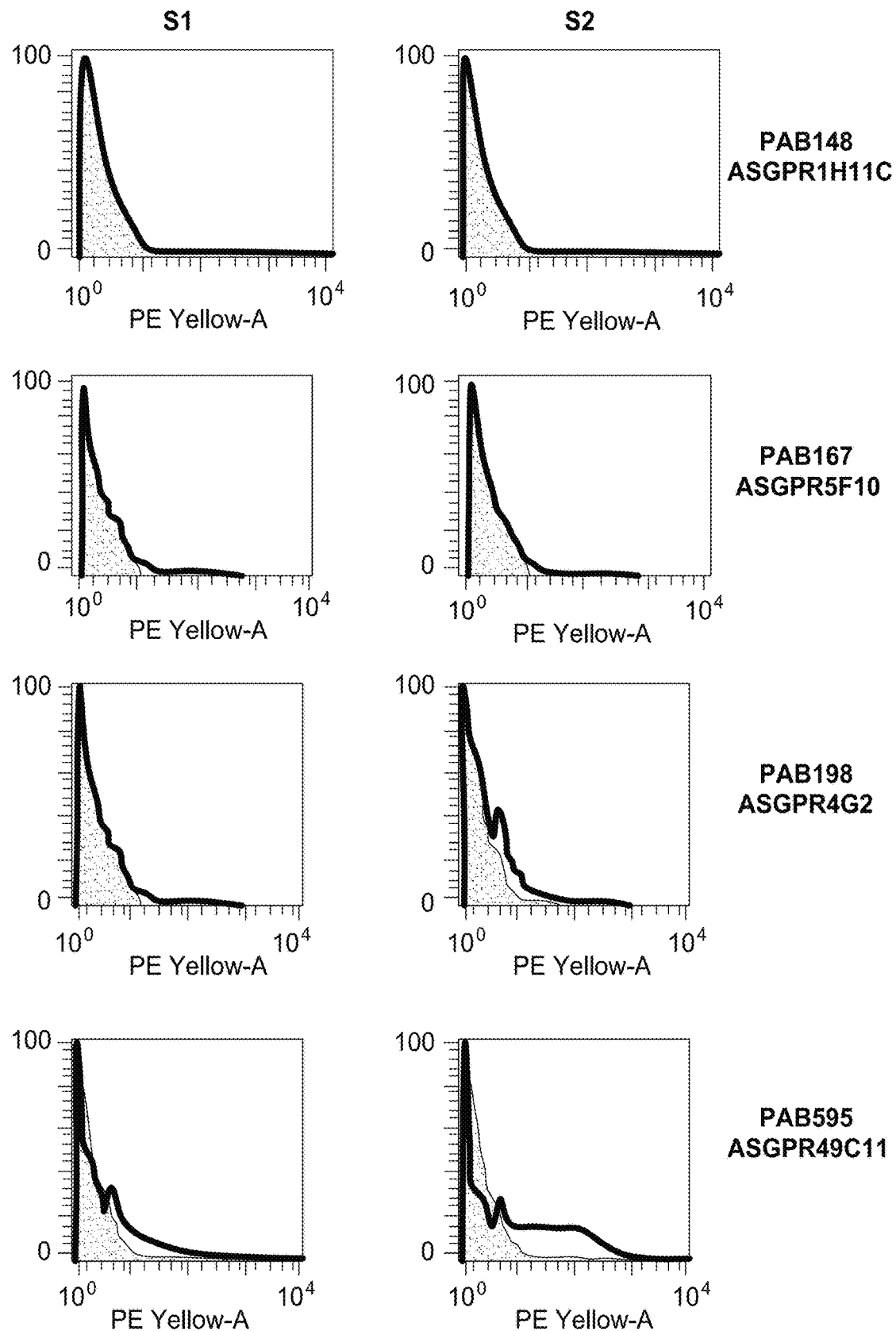
Figure 8B:
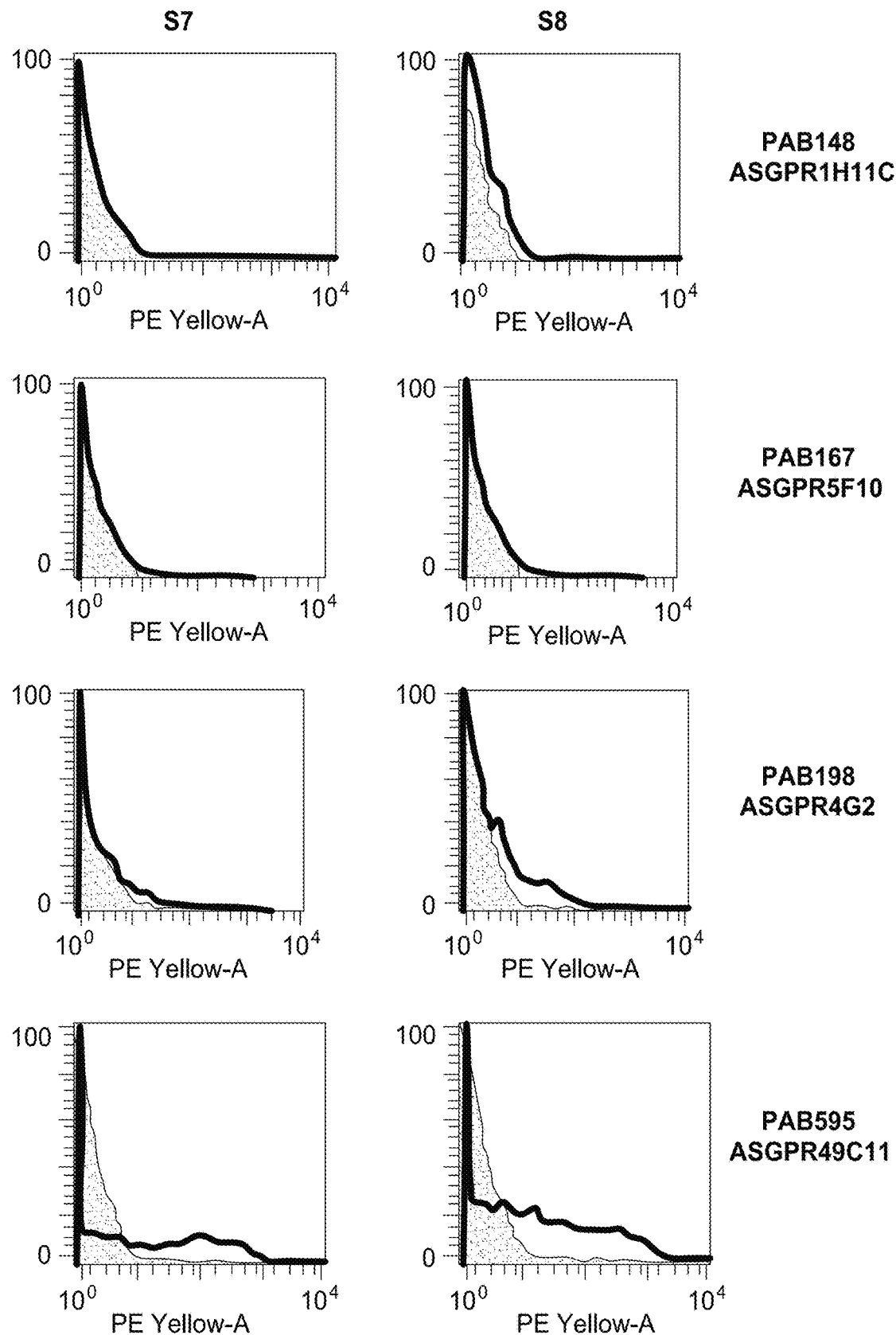
Figure 8C:
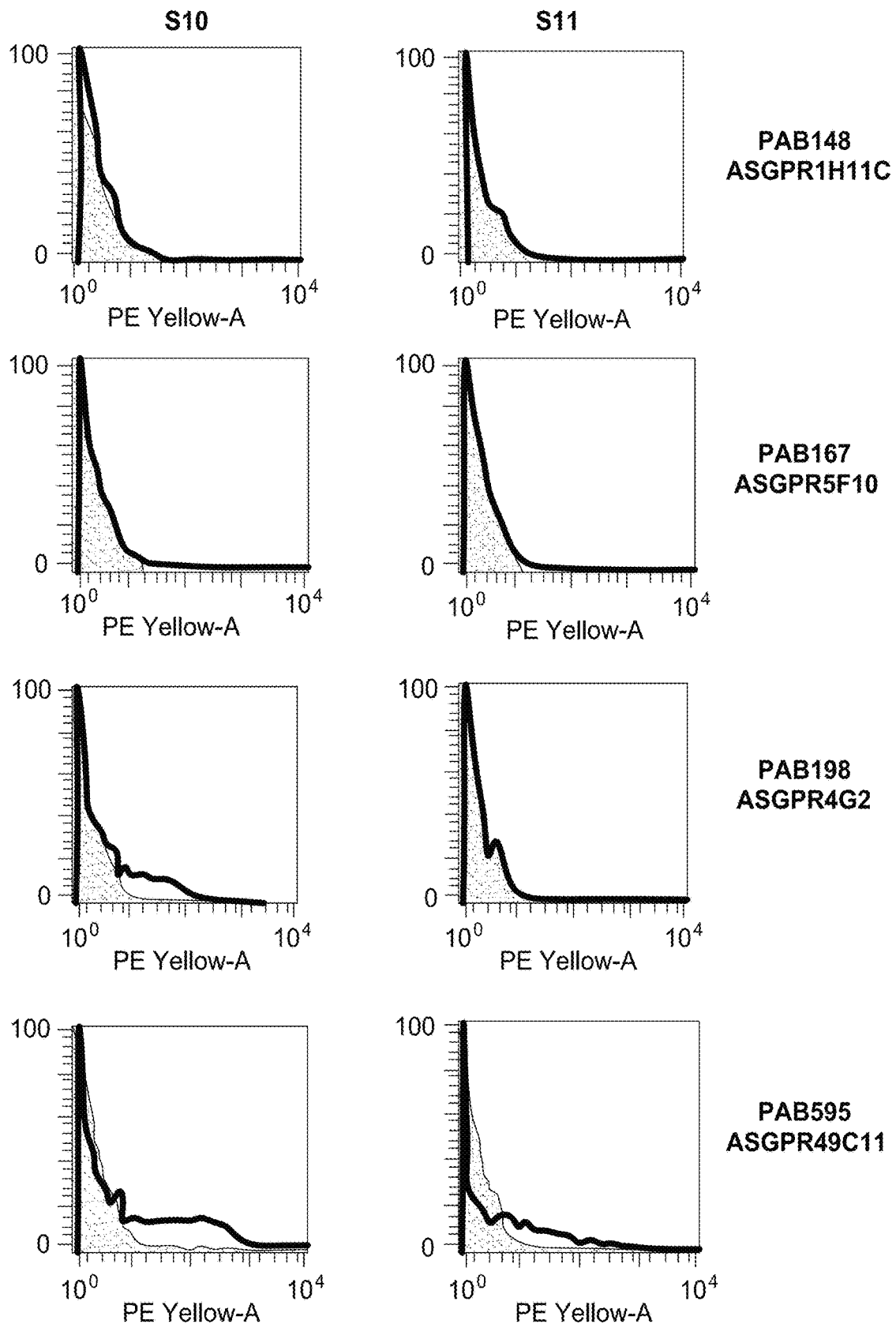
Figure 8D:
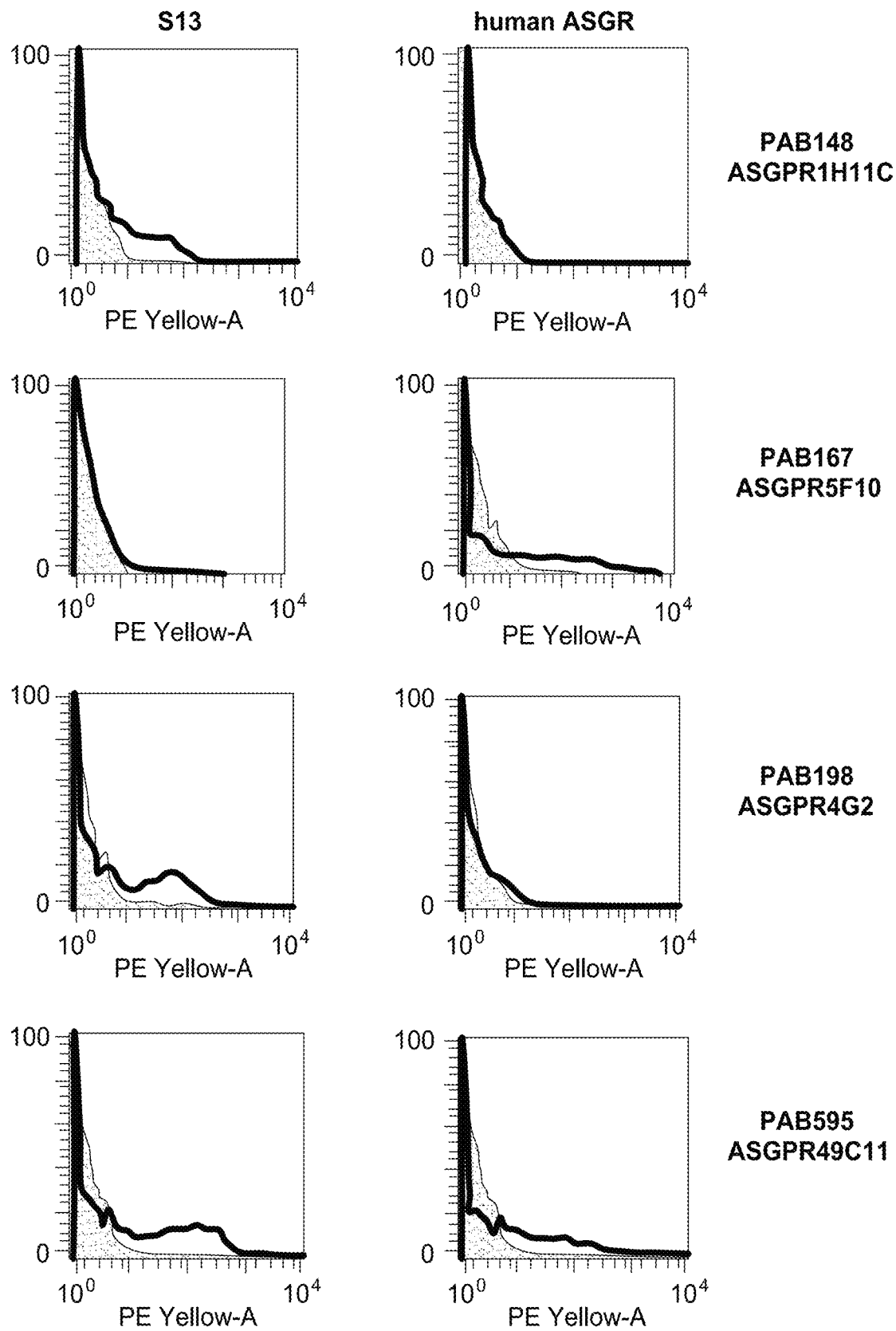

FIG. 7—GM-CSF/IFNa DCs (5,000/well) were loaded with 10 or 1 nM anti-DC-ASGPR.Doc:Coh.Flu M1, or hIgG4.Doc:Coh.Flu M1 complexes. After 6 h, autologous CD8+ T cells (200,000/well) were added into the cultures. At day 8, the CD8+ T cells were analyzed for expansion of cells bearing TCR specific for a HLA-A201 immuno-dominant peptide. The inner boxes indicate the percentage of tetramer-specific CD8+ T cells.

FIGS. 8A-8D demonstrated the cross reactivity of the different antibodies with monkey ASGPR.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Dendritic cells (DCs) are antigen-presenting cells that play a key role in regulating antigen-specific immunity (Mellman and Steinman 2001), (Banchereau, Briere et al. 2000), (Cella, Sallusto et al. 1997). DCs capture antigens, process them into peptides, and present these to T cells. Therefore delivering antigens directly to DC is a focus area for improving vaccines. One such example is the development of DC-based vaccines using ex-vivo antigen-loading of autologous DCs that are then re-administrated to patients (Banchereau, Schuler-Thurner et al. 2001), (Steinman and Dhodapkar 2001). Another strategy to improve vaccine efficacy is specific targeting to DC of antigen conjugated to antibodies against internalizing DC-specific receptors. The potential of targeting DC for vaccination is highlighted by key mouse studies. In vivo, targeting with an anti-LOX-1 mAb coupled to ovalbumin (OVA) induced a protective CD8+T cell response, via exogenous antigen cross-presentation toward the MHC class I pathway (Delneste, Magistrelli et al. 2002). Also, OVA conjugated to anti-DEC205 mAb in combination with a CD40L maturation stimulus enhanced the MHC class I-restricted presentation by DCs in vivo and led to the durable formation of effector memory CD8+ T cells (Bonifaz, Bonnyay et al. 2004). Both these studies showed dramatic dose-sparing (i.e., strong immune-responses at very low antigen doses) and suggested broader responses than normally seen with other types of OVA immunization. Recent work with targeting of HIV gag antigen to DC via DEC205 has extended these concepts to a clinically relevant antigen and confirmed the tenents of targeting antigen to DC—dramatic dose-sparing, protective responses from a single vaccination, and expansion of antigen-specific T cells in both the CD8 and CD4 compartments (Trumpfheller, Finke et al. 2006).

The present invention provides for the complexing of multiple antigens or proteins (engineered, expressed, and purified independently from the primary mAb) in a controlled, multivariable fashion, to one single primary recombinant mAb. Presently, there are methods for engineering site-specific biotinylation sites that provide for the addition of different proteins (each engineered separately linked to streptavidin) to the one primary mAb. However, the present invention provides for addition to the primary mAb of multiple combinations, in fixed equimolar ratios and locations, of separately engineered proteins.

As used herein, the term "modular rAb carrier" is used to describe a recombinant antibody system that has been engineered to provide the controlled modular addition of diverse antigens, activating proteins, or other antibodies to a single recombinant monoclonal antibody (mAb). The rAb may be a monoclonal antibody made using standard hybridoma techniques, recombinant antibody display, humanized monoclonal antibodies and the like. The modular rAb carrier can be used to, e.g., target (via one primary recombinant antibody against an internalizing receptor, e.g., a human dendritic cell receptor) multiple antigens and/or antigens and an activating cytokine to dendritic cells (DC). The modular rAb carrier may also be used to join two different recombinant mAbs end-to-end in a controlled and defined manner.

The antigen binding portion of the "modular rAb carrier" may be one or more variable domains, one or more variable and the first constant domain, an Fab fragment, a Fab' fragment, an F(ab)$_2$ fragment, and Fv fragment, and Fabc fragment and/or a Fab fragment with portions of the Fc domain to which the cognate modular binding portions are added to the amino acid sequence and/or bound. The antibody for use in the modular rAb carrier can be of any isotype or class, subclass or from any source (animal and/or recombinant).

In one non-limiting example, the modular rAb carrier is engineered to have one or more modular cohesin-dockerin protein domains for making specific and defined protein complexes in the context of engineered recombinant mAbs. The mAb is a portion of a fusion protein that includes one or more modular cohesin-dockerin protein domains carboxy from the antigen binding domains of the mAb. The cohesin-dockerin protein domains may even be attached post-translationally, e.g., by using chemical cross-linkers and/or disulfide bonding.

The term "antigen" as used herein refers to a molecule that can initiate a humoral and/or cellular immune response in a recipient of the antigen. Antigen may be used in two different contexts with the present invention: as a target for the antibody or other antigen recognition domain of the rAb or as the molecule that is carried to and/or into a cell or target by the rAb as part of a dockerin/cohesin-molecule complement to the modular rAb carrier. The antigen is usually an agent that causes a disease for which a vaccination would be advantageous treatment. When the antigen is presented on MHC, the peptide is often about 8 to about 25 amino acids. Antigens include any type of biologic molecule, including, for example, simple intermediary metabolites, sugars, lipids and hormones as well as macromolecules such as complex carbohydrates, phospholipids, nucleic acids and proteins. Common categories of antigens include, but are not limited to, viral antigens, bacterial antigens, fungal antigens, protozoal and other parasitic antigens, tumor antigens, antigens involved in autoimmune disease, allergy and graft rejection, and other miscellaneous antigens.

The modular rAb carrier is able to carry any number of active agents, e.g., antibiotics, anti-infective agents, antiviral agents, anti-tumoral agents, antipyretics, analgesics, anti-inflammatory agents, therapeutic agents for osteoporosis, enzymes, cytokines, anticoagulants, polysaccharides, collagen, cells, and combinations of two or more of the foregoing active agents. Examples of antibiotics for delivery using the present invention include, without limitation, tetracycline, aminoglycosides, penicillins, cephalosporins, sulfonamide drugs, chloramphenicol sodium succinate, erythromycin, vancomycin, lincomycin, clindamycin, nystatin, amphotericin B, amantidine, idoxuridine, p-amino salicyclic acid, isoniazid, rifampin, antinomycin D, mithramycin, daunomycin, adriamycin, bleomycin, vinblastine, vincristine, procarbazine, imidazole carboxamide, and the like.

Examples of anti-tumor agents for delivery using the present invention include, without limitation, doxorubicin, Daunorubicin, taxol, methotrexate, and the like. Examples of antipyretics and analgesics include aspirin, Motrin®, Ibuprofen®, naprosyn, acetaminophen, and the like.

Examples of anti-inflammatory agents for delivery using the present invention include, without limitation, include NSAIDS, aspirin, steroids, dexamethasone, hydrocortisone, prednisolone, Diclofenac Na, and the like.

Examples of therapeutic agents for treating osteoporosis and other factors acting on bone and skeleton include for delivery using the present invention include, without limitation, calcium, alendronate, bone GLa peptide, parathyroid hormone and its active fragments, histone H4-related bone formation and proliferation peptide and mutations, derivatives and analogs thereof.

Examples of enzymes and enzyme cofactors for delivery using the present invention include, without limitation, pancrease, L-asparaginase, hyaluronidase, chymotrypsin, trypsin, tPA, streptokinase, urokinase, pancreatin, collagenase, trypsinogen, chymotrypsinogen, plasminogen, streptokinase, adenyl cyclase, superoxide dismutase (SOD), and the like.

Examples of cytokines for delivery using the present invention include, without limitation, interleukins, transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Cytokines may be B/T-cell differentiation factors, B/T-cell growth factors, mitogenic cytokines, chemotactic cytokines, colony stimulating factors, angiogenesis factors, IFN-α, IFN-β, IFN-γ, IL1, IL2, IL3, IL4, IL5, IL6, IL7, IL8, IL9, IL10, IL11, IL12, IL13, IL14, IL15, IL16, IL17, IL18, etc., leptin, myostatin, macrophage stimulating protein, platelet-derived growth factor, TNF-α, TNF-β, NGF, CD40L, CD137L/4-1BBL, human lymphotoxin-β, G-CSF, M-CSF, GM-CSF, PDGF, IL-1α, IL1-β, IP-10, PF4, GRO, 9E3, erythropoietin, endostatin, angiostatin, VEGF or any fragments or combinations thereof. Other cytokines include members of the transforming growth factor (TGF) supergene family include the beta transforming growth factors (for example TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB).

Examples of growth factors for delivery using the present invention include, without limitation, growth factors that can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Examples of anticoagulants for delivery using the present invention include, without limitation, include warfarin, heparin, Hirudin, and the like. Examples of factors acting on the immune system include for delivery using the present invention include, without limitation, factors which control inflammation and malignant neoplasms and factors which attack infective microorganisms, such as chemotactic peptides and bradykinins.

Examples of viral antigens include, but are not limited to, e.g., retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS1, NS1-NS2A, 80% E, and other Japanese encephalitis viral antigen components; rabies viral antigens such as rabies glycoprotein, rabies nucleoprotein and other rabies viral antigen components. See Fundamental Virology, Second Edition, eds. Fields, B. N. and Knipe, D. M. (Raven Press, New York, 1991) for additional examples of viral antigens.

Antigenic targets that may be delivered using the rAb-DC/DC-antigen vaccines of the present invention include genes encoding antigens such as viral antigens, bacterial antigens, fungal antigens or parasitic antigens. Viruses include picornavirus, coronavirus, togavirus, flavirvirus, rhabdovirus, paramyxovirus, orthomyxovirus, bunyavirus, arenavirus, reovirus, retrovirus, papilomavirus, parvovirus, herpesvirus, poxvirus, hepadnavirus, and spongiform virus. Other viral targets include influenza, herpes simplex virus 1 and 2, measles, dengue, smallpox, polio or HIV. Pathogens include trypanosomes, tapeworms, roundworms, helminthes, and malaria. Tumor markers, such as fetal antigen or prostate specific antigen, may be targeted in this manner. Other examples include: HIV env proteins and hepatitis B surface antigen. Administration of a vector according to the present invention for vaccination purposes would require that the vector-associated antigens be sufficiently non-immunogenic to enable long term expression of the transgene, for which a strong immune response would be desired. In some cases, vaccination of an individual may only be required infrequently, such as yearly or biennially, and provide long term immunologic protection against the infectious agent. Specific examples of organisms, allergens and nucleic and amino sequences for use in vectors and ultimately as antigens with the present invention may be found in U.S. Pat. No. 6,541,011, relevant portions incorporated herein by reference, in particular, the tables that match organisms and specific sequences that may be used with the present invention.

Bacterial antigens for use with the rAb vaccine disclosed herein include, but are not limited to, e.g., bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components, *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; haemophilus influenza bacterial antigens such as capsular polysaccharides and other haemophilus influenza bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens. Partial or whole pathogens may also be: haemophilus influenza; *Plasmodium falciparum; Neisseria meningitidis; Streptococcus pneumoniae; Neisseria gonorrhoeae*; salmonella serotype typhi; shigella; *Vibrio cholerae*; Dengue Fever; Encephalitides; Japanese Encephalitis; Lyme disease; *Yersinia pestis*; west nile virus; yellow fever; tularemia; hepatitis (viral; bacterial); RSV (respiratory syncytial virus); HPIV 1 and HPIV 3; adenovirus; small pox; allergies and cancers.

Fungal antigens for use with compositions and methods of the invention include, but are not limited to, e.g., candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Examples of protozoal and other parasitic antigens include, but are not limited to, e.g., *Plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; *toxoplasma* antigens such as SAG-1, p30 and other toxoplasmal antigen components; schistosomae antigens such as glutathione-S-transferase, paramyosin, and other schistosomal antigen components; *Leishmania major* and other leishmaniae antigens such as gp63, lipophosphoglycan and its associated protein and other leishmanial antigen components; and *Trypanosoma cruzi* antigens such as the 75-77 kDa antigen, the 56 kDa antigen and other trypanosomal antigen components.

Antigen that can be targeted using the rAb of the present invention will generally be selected based on a number of factors, including: likelihood of internalization, level of immune cell specificity, type of immune cell targeted, level of immune cell maturity and/or activation and the like. Examples of cell surface markers for dendritic cells include, but are not limited to, MHC class I, MHC Class II, B7-2, CD18, CD29, CD31, CD43, CD44, CD45, CD54, CD58, CD83, CD86, CMRF-44, CMRF-56, DCIR and/or ASPGR and the like; while in some cases also having the absence of CD2, CD3, CD4, CD8, CD14, CD15, CD16, CD19, CD20, CD56, and/or CD57. Examples of cell surface markers for antigen presenting cells include, but are not limited to, MHC class I, MHC Class II, CD40, CD45, B7-1, B7-2, IFN-γ receptor and IL-2 receptor, ICAM-1 and/or Fcγ receptor. Examples of cell surface markers for T cells include, but are not limited to, CD3, CD4, CD8, CD 14, CD20, CD11b, CD16, CD45 and HLA-DR.

Target antigens on cell surfaces for delivery includes those characteristic of tumor antigens typically will be derived from the cell surface, cytoplasm, nucleus, organelles and the like of cells of tumor tissue. Examples of tumor targets for the antibody portion of the present invention include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia.

Examples of antigens that may be delivered alone or in combination to immune cells for antigen presentation using the present invention include tumor proteins, e.g., mutated oncogenes; viral proteins associated with tumors; and tumor mucins and glycolipids. The antigens may be viral proteins associated with tumors would be those from the classes of viruses noted above. Certain antigens may be characteristic of tumors (one subset being proteins not usually expressed by a tumor precursor cell), or may be a protein which is normally expressed in a tumor precursor cell, but having a mutation characteristic of a tumor. Other antigens include mutant variant(s) of the normal protein having an altered activity or subcellular distribution, e.g., mutations of genes giving rise to tumor antigens.

Specific non-limiting examples of tumor antigens include: CEA, prostate specific antigen (PSA), HER-2/neu, BAGE, GAGE, MAGE 1-4, 6 and 12, MUC (Mucin) (e.g., MUC-1, MUC-2, etc.), GM2 and GD2 gangliosides, ras, myc, tyrosinase, MART (melanoma antigen), Pmel 17(gp100), GnT-V intron V sequence (N-acetylglucoaminyltransferase V intron V sequence), Prostate Ca psm, PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP), Bcl-2, and Ki-67. In addition, the immunogenic molecule can be an autoantigen involved in the initiation and/or propagation of an autoimmune disease, the pathology of which is largely due to the activity of antibodies specific for a molecule expressed by the relevant target organ, tissue, or cells, e.g., SLE or MG. In such diseases, it can be desirable to direct an ongoing antibody-mediated (i.e., a Th2-type) immune response to the relevant autoantigen towards a cellular (i.e., a Th1-type) immune response. Alternatively, it can be desirable to prevent onset of or decrease the level of a Th2 response to the autoantigen in a subject not having, but who is suspected of being susceptible to, the relevant autoimmune disease by prophylactically inducing a Th1 response to the appropriate autoantigen. Autoantigens of interest include, without limitation: (a) with respect to SLE, the Smith protein, RNP ribonucleoprotein, and the SS-A and SS-B proteins; and (b) with respect to MG, the acetylcholine receptor. Examples of other miscellaneous antigens involved in one or more types of autoimmune response include, e.g., endogenous hormones such as luteinizing hormone, follicular stimulating hormone, testosterone, growth hormone, prolactin, and other hormones.

Antigens involved in autoimmune diseases, allergy, and graft rejection can be used in the compositions and methods of the invention. For example, an antigen involved in any one or more of the following autoimmune diseases or disorders can be used in the present invention: diabetes, diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis. Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of antigens involved in allergy include pollen antigens such as Japanese cedar pollen antigens, ragweed pollen antigens, rye grass pollen antigens, animal derived antigens such as dust mite antigens and feline antigens, histocompatiblity antigens, and penicillin and other therapeutic drugs. Examples of antigens involved in graft rejection include antigenic components of the graft to be transplanted into the graft recipient such as heart, lung, liver, pancreas, kidney, and neural graft components. The antigen may be an altered peptide ligand useful in treating an autoimmune disease.

As used herein, the term "epitope(s)" refer to a peptide or protein antigen that includes a primary, secondary or tertiary structure similar to an epitope located within any of a number of pathogen polypeptides encoded by the pathogen DNA or RNA. The level of similarity will generally be to such a degree that monoclonal or polyclonal antibodies directed against such polypeptides will also bind to, react with, or otherwise recognize, the peptide or protein antigen. Various immunoassay methods may be employed in conjunction with such antibodies, such as, for example, Western blotting, ELISA, RIA, and the like, all of which are known to those of skill in the art. The identification of pathogen epitopes, and/or their functional equivalents, suitable for use in vaccines is part of the present invention. Once isolated and identified, one may readily obtain functional equivalents. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

The preparation of vaccine compositions that includes the nucleic acids that encode antigens of the invention as the active ingredient, may be prepared as injectables, either as liquid solutions or suspensions; solid forms suitable for solution in, or suspension in, liquid prior to infection can also be prepared. The preparation may be emulsified, encapsulated in liposomes. The active immunogenic ingredients are often mixed with carriers which are pharmaceutically acceptable and compatible with the active ingredient.

The term "pharmaceutically acceptable carrier" refers to a carrier that does not cause an allergic reaction or other untoward effect in subjects to whom it is administered. Suitable pharmaceutically acceptable carriers include, for example, one or more of water, saline, phosphate buffered saline, dextrose, glycerol, ethanol, or the like and combinations thereof. In addition, if desired, the vaccine can contain minor amounts of auxiliary substances such as wetting or emulsifying agents, pH buffering agents, and/or adjuvants which enhance the effectiveness of the vaccine. Examples of adjuvants that may be effective include but are not limited to: aluminum hydroxide, N-acetyl-muramyl-L-threonyl-D-isoglutamine (thr-MDP), N-acetyl-nor-muramyl-L-alanyl-D-isoglutamine, MTP-PE and RIBI, which contains three components extracted from bacteria, monophosporyl lipid A, trehalose dimycolate and cell wall skeleton (MPL+TDM+CWS) in a 2% squalene/Tween 80 emulsion. Other examples of adjuvants include DDA (dimethyldioctadecylammonium bromide), Freund's complete and incomplete adjuvants and QuilA. In addition, immune modulating substances such as lymphokines (e.g., IFN-γ, IL-2 and IL-12) or synthetic IFN-γ inducers such as poly I:C can be used in combination with adjuvants described herein.

Pharmaceutical products that may include a naked polynucleotide with a single or multiple copies of the specific nucleotide sequences that bind to specific DNA-binding sites of the apolipoproteins present on plasma lipoproteins as described in the current invention. The polynucleotide may encode a biologically active peptide, antisense RNA, or ribozyme and will be provided in a physiologically acceptable administrable form. Another pharmaceutical product that may spring from the current invention may include a highly purified plasma lipoprotein fraction, isolated according to the methodology, described herein from either the patients blood or other source, and a polynucleotide containing single or multiple copies of the specific nucleotide sequences that bind to specific DNA-binding sites of the apolipoproteins present on plasma lipoproteins, prebound to the purified lipoprotein fraction in a physiologically acceptable, administrable form.

Yet another pharmaceutical product may include a highly purified plasma lipoprotein fraction which contains recombinant apolipoprotein fragments containing single or multiple copies of specific DNA-binding motifs, prebound to a polynucleotide containing single or multiple copies of the specific nucleotide sequences, in a physiologically acceptable administrable form. Yet another pharmaceutical product may include a highly purified plasma lipoprotein fraction which contains recombinant apolipoprotein fragments containing single or multiple copies of specific DNA-binding motifs, prebound to a polynucleotide containing single or multiple copies of the specific nucleotide sequences, in a physiologically acceptable administrable form.

The dosage to be administered depends to a great extent on the body weight and physical condition of the subject being treated as well as the route of administration and frequency of treatment. A pharmaceutical composition that includes the naked polynucleotide prebound to a highly purified lipoprotein fraction may be administered in amounts ranging from 1 µg to 1 mg polynucleotide and 1 µg to 100 mg protein.

Administration of an rAb and rAb complexes a patient will follow general protocols for the administration of chemotherapeutics, taking into account the toxicity, if any, of the vector. It is anticipated that the treatment cycles would be repeated as necessary. It also is contemplated that various standard therapies, as well as surgical intervention, may be applied in combination with the described gene therapy.

Where clinical application of a gene therapy is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention may include an effective amount of the compound, dissolved or dispersed in a pharmaceutically acceptable carrier or aqueous medium. Such compositions can also be referred to as inocula. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions. The compositions of the present invention may include classic pharmaceutical preparations. Dispersions also can be prepared in glycerol, liquid polyethylene glycols, and mixtures thereof and in oils. Under ordinary conditions of storage and use, these preparations contain a preservative to prevent the growth of microorganisms.

Disease States. Depending on the particular disease to be treated, administration of therapeutic compositions according to the present invention will be via any common route so long as the target tissue is available via that route in order to maximize the delivery of antigen to a site for maximum (or in some cases minimum) immune response. Administration will generally be by orthotopic, intradermal, subcutaneous, intramuscular, intraperitoneal or intravenous injection. Other areas for delivery include: oral, nasal, buccal, rectal, vaginal or topical. Topical administration would be particularly advantageous for treatment of skin cancers. Such compositions would normally be administered as pharmaceutically acceptable compositions that include physiologically acceptable carriers, buffers or other excipients.

Vaccine or treatment compositions of the invention may be administered parenterally, by injection, for example, either subcutaneously or intramuscularly. Additional formulations which are suitable for other modes of administration include suppositories, and in some cases, oral formulations or formulations suitable for distribution as aerosols. In the case of the oral formulations, the manipulation of T-cell subsets employing adjuvants, antigen packaging, or the addition of individual cytokines to various formulation that result in improved oral vaccines with optimized immune responses. For suppositories, traditional binders and carriers may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25-70%.

The antigen encoding nucleic acids of the invention may be formulated into the vaccine or treatment compositions as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups can also be derived from inorganic bases such as, for example, sodium, potassium, ammonium, calcium, or ferric hydroides, and such organic bases as isopropylamine, trimethylamine, 2-ethylamino ethanol, histidine, procaine, and the like.

Vaccine or treatment compositions are administered in a manner compatible with the dosage formulation, and in such amount as will be prophylactically and/or therapeutically effective. The quantity to be administered depends on the subject to be treated, including, e.g., capacity of the subject's immune system to synthesize antibodies, and the degree of protection or treatment desired. Suitable dosage ranges are of the order of several hundred micrograms active ingredient per vaccination with a range from about 0.1 mg to 1000 mg, such as in the range from about 1 mg to 300 mg, and preferably in the range from about 10 mg to 50 mg. Suitable regiments for initial administration and booster shots are also variable but are typified by an initial administration followed by subsequent inoculations or other administrations. Precise amounts of active ingredient required to be administered depend on the judgment of the practitioner and may be peculiar to each subject. It will be apparent to those of skill in the art that the therapeutically effective amount of nucleic acid molecule or fusion polypeptides of this invention will depend, inter alia, upon the administration schedule, the unit dose of antigen administered, whether the nucleic acid molecule or fusion polypeptide is administered in combination with other therapeutic agents, the immune status and health of the recipient, and the therapeutic activity of the particular nucleic acid molecule or fusion polypeptide.

The compositions can be given in a single dose schedule or in a multiple dose schedule. A multiple dose schedule is one in which a primary course of vaccination may include, e.g., 1-10 separate doses, followed by other doses given at subsequent time intervals required to maintain and or reinforce the immune response, for example, at 1-4 months for a second dose, and if needed, a subsequent dose(s) after several months. Periodic boosters at intervals of 1-5 years, usually 3 years, are desirable to maintain the desired levels of protective immunity. The course of the immunization can be followed by in vitro proliferation assays of peripheral blood lymphocytes (PBLs) co-cultured with ESAT6 or ST-CF, and by measuring the levels of IFN-γ released from the primed lymphocytes. The assays may be performed using conventional labels, such as radionucleotides, enzymes, fluorescent labels and the like. These techniques are known to one skilled in the art and can be found in U.S. Pat. Nos. 3,791,932, 4,174,384 and 3,949,064, relevant portions incorporated by reference.

The modular rAb carrier and/or conjugated rAb carrier-(cohesion/dockerin and/or dockerin-cohesin)-antigen complex (rAb-DC/DC-antigen vaccine) may be provided in one or more "unit doses" depending on whether the nucleic acid vectors are used, the final purified proteins, or the final vaccine form is used. Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. The subject to be treated may also be evaluated, in particular, the state of the subject's immune system and the protection desired. A unit dose need not be administered as a single injection but may include continuous infusion over a set period of time. Unit dose of the present invention may conveniently may be described in terms of DNA/kg (or protein/Kg) body weight, with ranges between about 0.05, 0.10, 0.15, 0.20, 0.25, 0.5, 1, 10, 50, 100, 1,000 or more mg/DNA or protein/kg body weight are administered. Likewise the amount of rAb-DC/DC-antigen vaccine delivered can vary from about 0.2 to about 8.0 mg/kg body weight. Thus, in particular embodiments, 0.4 mg, 0.5 mg, 0.8 mg, 1.0 mg, 1.5 mg, 2.0 mg, 2.5 mg, 3.0 mg, 4.0 mg, 5.0 mg, 5.5 mg, 6.0 mg, 6.5 mg, 7.0 mg and 7.5 mg of the vaccine may be delivered to an individual in vivo. The dosage of rAb-DC/DC-antigen vaccine to be administered depends to a great extent on the weight and physical condition of the subject being treated as well as the route of administration and the frequency of treatment. A pharmaceutical composition that includes a naked polynucleotide prebound to a liposomal or viral delivery vector may be administered in amounts ranging from 1 µg to 1 mg polynucleotide to 1 µg to 100 mg protein. Thus, particular compositions may include between about 1 µg, 5 µg, 10 µg, 20µg, 30 µg, 40 µg, 50 µg, 60 µg, 70 µg, 80 µg, 100 µg, 150 µg, 200 µg, 250 µg, 500 µg, 600 µg, 700 µg, 800 µg, 900 µg or 1,000 µg polynucleotide or protein that is bound independently to 1 µg, 5 µg, 10 µg, 20 µg, 3.0 µg, 40 µg 50 µg, 60 µg, 70 µg, 80 µg, 100 µg, 150 µg, 200 µg, 250 µg, 500 µg, 600 µg, 700 µg, 800 µg, 900 µg, 1 mg, 1.5 mg, 5 mg, 10 mg, 20 mg, 30 mg, 40 mg, 50 mg, 60 mg, 70 mg, 80 mg, 90 mg or 100 mg vector.

The present invention was tested in an in vitro cellular system that measures immune stimulation of human Flu-specific T cells by dendritic cells to which Flu antigen has been targeted. The results shown herein demonstrate the specific expansion of such antigen specific cells at doses of the antigen which are by themselves ineffective in this system.

The present invention may also be used to make a modular rAb carrier that is, e.g., a recombinant humanized mAb (directed to a specific human dendritic cell receptor) complexed with protective antigens from Ricin, Anthrax toxin, and *Staphylococcus* B enterotoxin. The potential market for this entity is vaccination of all military personnel and stored vaccine held in reserve to administer to large population centers in response to any biothreat related to these agents. The invention has broad application to the design of vaccines in general, both for human and animal use. Industries of interest include the pharmaceutical and biotechnology industries.

The present invention includes compositions and methods, including vaccines, that specifically target (deliver)

antigens to antigen-presenting cells (APCs) for the purpose of eliciting potent and broad immune responses directed against the antigen. These compositions evoke protective or therapeutic immune responses against the agent (pathogen or cancer) from which the antigen was derived. In addition the invention creates agents that are directly, or in concert with other agents, therapeutic through their specific engagement of a receptor called DC-ASGPR that is expressed on antigen-presenting cells.

Figure 1E:
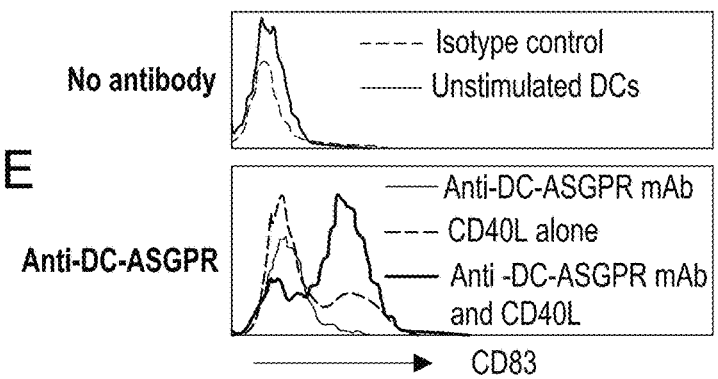

The novel recombinant humanized mAb (directed to the specific human dendritic cell receptor DC-ASGPR) fused through the antibody (Ab) heavy chain to antigens known or suspected to encode protective antigens. These include as examples for vaccination against various agents—hemagglutinins from Influenza H5N1; HIV gag from attenuated toxins from Ricin, Anthrax toxin, and *Staphylococcus* B enterotoxin; 'strings' of antigenic peptides from melanona antigens, etc. The present invention may be used as a preventative or therapeutic vaccination for at risk or infected patients. The invention has broad application for vaccination against many diseases and cancers, both for human and animal use. Industries that can use the present invention include the pharmaceutical and biotechnological.

The present invention can be used to target antigens to APC for vaccination purposes. It is not known which antigen internalizing receptor will be best suited for this purpose. The invention describes particularly advantageous features of DC-ASGPR as for this purpose. Furthermore, the invention shows that engaging DC-ASGPR can be beneficial in the sense of activating the immune system with highly predicted significant therapeutic benefit.

The present invention includes the development of high affinity monoclonal antibodies against human DC-ASGPR. Receptor ectodomain.hIgG (human IgG1Fc) and AP (human placental alkaline phosphatase) fusion proteins were produced for immunization of mice and screening of mAbs, respectively. An expression construct for hDCIR ectodomain.IgG was described previously (Bates, Fournier et al. 1999) and used the mouse SLAM (mSLAM) signal peptide to direct secretion (Bendtsen, Nielsen et al. 2004). An expression vector for hDCIR ectodomain.AP was generated using PCR to amplify AP resides 133-1581 (gbIBC0096471) while adding a proximal in-frame Xho I site and a distal TGA stop codon and Not I site. This Xho I-Not I fragment replaced the IgG coding sequence in the above hDCIR ectodomain.IgG vector. DC-ASGPR ectodomain constructs in the same Ig and AP vector series contained inserts encoding (bp 484-1251, gi153832017). DC-ASGPR fusion proteins were produced using the FreeStyle™ 293 Expression System (Invitrogen) according to the manufacturer's protocol (1 mg total plasmid DNA with 1.3 ml 293 Fectin reagent/L of transfection). For rAb production, equal amounts of vector encoding the H and L chain were co-transfected. Transfected cells are cultured for 3 days, the culture supernatant was harvested and fresh media added with continued incubation for two days. The pooled supernatants were clarified by filtration. Receptor ectodomain-.hIgG was purified by HiTrap protein A affinity chromatography with elution by 0.1 M glycine pH 2.7 and then dialyzed versus PBS. rAbs (recombinant antibodies described later) were purified similarly, by using HiTrap MabSelect™ columns. Mouse mAbs were generated by conventional cell fusion technology. Briefly, 6-week-old BALB/c mice were immunized intraperitonealy with 20 μg of receptor ectodomain.hIgGFc fusion protein with Ribi adjuvant, then boosts with 20 μg antigen 10 days and 15 days later. After 3 months, the mice were boosted again three days prior to taking the spleens. Alternately, mice were injected in the footpad with 1-10 μg antigen in Ribi adjuvant every 3-4 days over a 30-40 day period. 3-4 days after a final boost, draining lymph nodes were harvested. B cells from spleen or lymph node cells were fused with SP2/O-Ag 14 cells (Shulman, Wilde et al. 1978) using conventional techniques.

ELISA was used to screen hybridoma supernatants against the receptor ectodomain fusion protein compared to the fusion partner alone, or versus the receptor ectodomain fused to AP (Bates, Fournier et al. 1999). Positive wells were then screened in FACS using 293F cells transiently transfected with expression plasmids encoding full-length receptor cDNAs. Selected hybridomas were single cell cloned and expanded in CELLine flasks (Intergra). Hybridoma supernatants were mixed with an equal volume of 1.5 M glycine, 3 M NaCl, 1×PBS, pH 7.8 and tumbled with MabSelect resin. The resin was washed with binding buffer and eluted with 0.1 M glycine, pH 2.7. Following neutralization with 2 M Tris, mAbs were dialyzed versus PBS.

Characterization of purified anti-DC-ASGPR monoclonal antibodies by direct ELISA. the relative affinities of several anti-DC-ASGPR mAbs by ELISA were determined (i.e., DC-ASGPR.Ig protein is immobilized on the microplate surface and the antibodies are tested in a dose titration series for their ability to bind to DC-ASGPR.Ig (as detected by an anti-mouse IgG.HRP conjugate reagent. In this example, PAB42 and PAB44 show higher affinity binding than other mAbs. The same mAbs fail to bind significantly to human Ig bound to the microplate surface. This shows that the mAbs react to the DC-ASGPR ectodomain part of the DC-ASGPR.Ig fusion protein (data not shown).

Characterization of purified anti-DC-ASGPR monoclonal antibodies by indirect ELISA. Next, the relative affinities of several anti-DC-ASGPR mAbs were determined by ELISA (i.e., anti-DC-ASGPR mAb is immobilized on the microplate surface and tested in a dose titration series for their ability to bind to DC-ASGPR.AP reagent. It was found that the supernatants from the hybridomas listed as: PAB42, PAB44 and PAB54 show higher affinity binding than other mAbs (data not shown).

Characterization of anti-DC-ASGPR mAbs by FACS. The panel of mAbs was also tested by FACS versus 293F cells transfected with expression plasmid directing synthesis of cell surface DC-ASGPR. Mean fluorescence intensity of the signal was subtracted from the analogous signal versus non-transfected 293F cells. By this criterion, the mAbs are able to bind to specifically to the surface of cells bearing DC-ASGPR. Some mAbs, e.g., 37A7 appear particularly advantageous in this regard (data not shown).

FIGS. 1A to 1D shows that signaling through DC-ASGPR activates DCs. DCs are the primary immune cells that determine the results of immune responses, either induction or tolerance, depending on their activation (15). The role of LLRs in DC activation is not clear yet. Therefore, we tested whether triggering the LLR DC-ASGPR can result in the activation of DCs. Both three and six day in vitro cultured GM/IL-4 DCs express LOX-1, ASGPR, and CLEC-6 (FIG. 1A). Six day DCs were stimulated with mAb specific to DC-ASGPR, and data in FIG. 1B show that signals through DC-ASGPR could activate DCs, resulting in the increased expression of CD86 and HLA-DR. Triggering DC-ASGPR on DCs also resulted in the increased production of IL-6, MCP-1, IL-12p40, and IL-8 from DCs (FIG. 1C). Other cytokines and chemokines, TNFa, IP-10, MIP-1α, and IL-10, were also significantly increased (data not shown) by signaling through DC-ASGPR, suggesting that DC-ASGPR can deliver cellular signals to activate DCs. Consistently, DCs stimulated with DC-ASGPR specific mAb expressed increased levels of multiple genes, including co-stimulatory molecules as well as chemokine and cytokine-related genes (FIG. 1D). The possible contribution of LLRs in TLR2 and TLR4-mediated immune cell activation has been described previously (13, 16). We observed that signals through DC-ASGPR could synergize with signal through CD40 for a further activation of DCs (FIG. 1E). This is important because LLRs could serve as co-stimulatory molecules during in vivo DC activation. Taken together, data in FIG. 1 prove that signaling through DC-ASGPR can activate DCs and that DC-ASGPR serves as a co-stimulatory molecule for the activation of DCs. DC-ASGPR engagement during CD40-CD40L interaction results in dramatically increased production of IL-12p70.

DCs stimulated through DC-ASGPR induce potent humoral immune responses. DCs play an important role in humoral immune responses by providing signals for both T-dependent and T-independent B cell responses (19-22) and by transferring antigens to B cells (23, 24). In addition to DCs, signaling through TLR9 as a third signal is necessary for efficient B cell responses (25, 26).

Therefore, we tested the role of DC-ASGPR in DCs-mediated humoral immune responses in the presence of TLR9 ligand, CpG. Six day GM/IL-4 DCs were stimulated with anti-DC-ASGPR mAb, and then purified B cells were co-cultured. As shown in FIG. 2A, DCs activated with anti-DC-ASGPR mAb resulted in remarkably enhanced B cell proliferation (CFSE dilution) and plasma cell differentiation (CD38$^+$CD20$^-$), compared to DCs stimulated with control mAb. CD38$^+$CD20$^-$ B cells have a typical morphology of plasma cells, but they do not express CD138. The majority of proliferating cells did not express CCR2, CCR4, CCR6, or CCR7. The amounts of total immunoglobulins (Igs) produced were measured by ELISA (FIG. 2B). Consistent with the data in FIG. 2A, B cells cultured with anti-DC-ASGPR-stimulated DCs resulted in significantly increased production of total IgM, IgG, and IgA. In addition to the total Igs, we also observed that DCs activated by triggering DC-ASGPR are more potent than DCs stimulated with control mAb for the production of influenza-virus-specific IgM, IgG, and IgA (FIG. 2C) by B cells, suggesting that DC-ASGPR-mediated DC activation contributes to both total and antigen specific humoral immune responses. We tested the role of DC-ASGPR in ex vivo antigen presenting cells (APCs) in humoral immune responses. Parts of APCs in PBMCs, including CD19$^+$ and CD14$^+$ cells, express DC-ASGPR (Supplementary FIG. 2). PBMCs from buffy coats were cultured in the plates coated with anti-DC-ASGPR mAb, and the total Igs and B cell proliferation were measured. Consistent with the data generated from DCs (FIG. 2A), APCs stimulated through DC-ASGPR resulted in enhanced B cell proliferation and plasma cell differentiation in the absence (upper panels in FIG. 2d) or presence (lower panels in FIG. 2D) of TLR9 ligand. The total IgM, IgG, and IgA were also significantly increased when PBMCs were cultured in the plates coated with mAb against DC-ASGPR (FIG. 2e). As shown in FIG. 1, DCs activated by signaling through DC-ASGPR have matured phenotypes and produce large amounts of inflammatory cytokines and chemokines, and both matured DC phenotypes and soluble factors from DCs could contribute to the enhanced B cells responses (FIG. 2). However, DC-derived B lymphocyte stimulator protein (BLyS, BAFF) and a proliferation-inducing ligand (APRIL) are also important molecules by which DCs can directly regulate human B cell proliferation and function (27-30). Therefore, we tested whether signals through DC-ASGPR could alter the expression levels of BLyS and APRIL. Data in FIG. 2d show that DCs stimulated through DC-ASGPR expressed increased levels of intracellular APRIL as well as APRIL secreted, but not BLyS (not shown). Expression levels of BLyS and APRIL receptors on B cells in the mixed cultures were measured, but there was no significant change (not shown).

DC-ASGPR contributes to B cell activation and Ig production. CD19$^+$ B cells express DC-ASGPR (FIG. 3A). Therefore, we tested the role of DC-ASGPR in B cell activation. Data in FIG. 3B show that B cells stimulated through DC-ASGPR produced significantly higher amounts of chemokines. In addition to IL-8 and MIP-1α, slight increases in IL-6 and TNFα were also observed when B cells were stimulated with the anti-DC-ASGPR mAb, compared to control mAb. Genes related to cell activation were also up-regulated (FIG. 3C). B cells produced IgM, IgG, and IgA when they were stimulated through DC-ASGPR (FIG. 3D), suggesting that DC-ASGPR could play an important role in the maintenance of normal immunoglobulin levels in vivo. However, signaling through DC-ASGPR alone did not induce significant B cell proliferation.

Figure 4C:
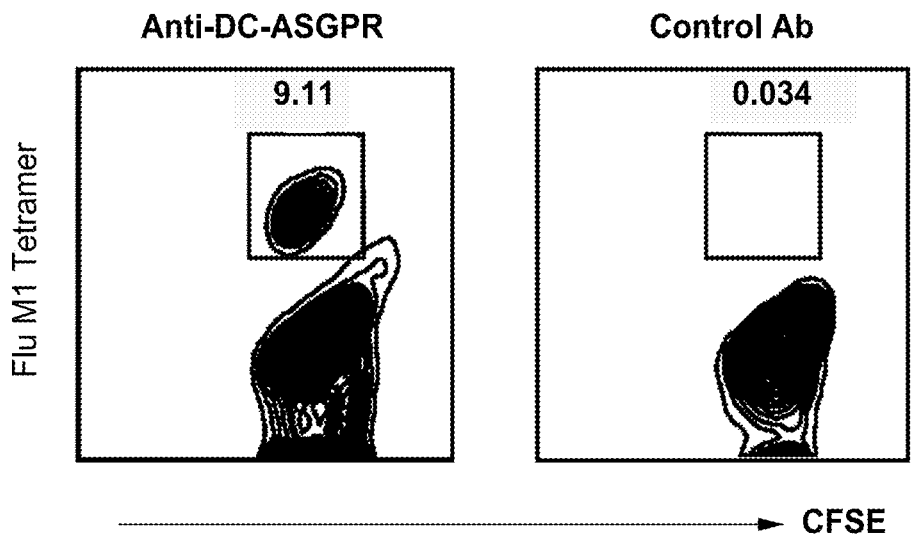
Figure 4D:
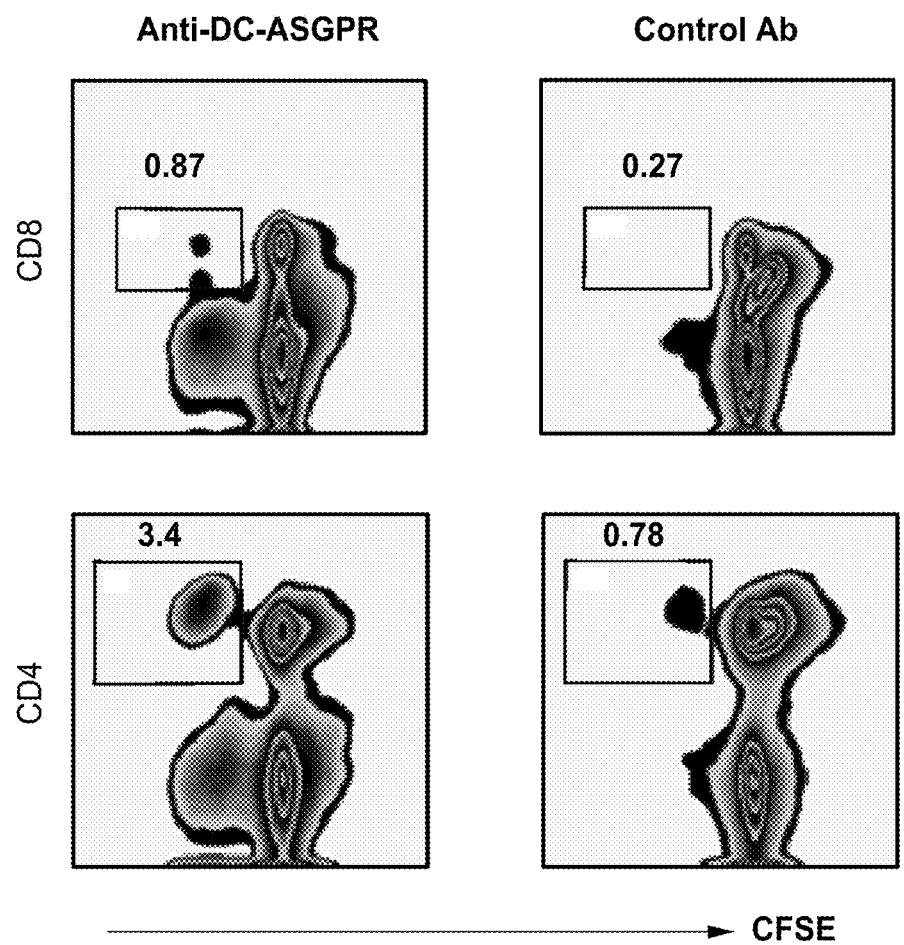

Role of DC-ASGPR in T cell responses. DCs stimulated through DC-ASGPR express enhanced levels of co-stimulatory molecules and produce increased amounts of cytokines and chemokines (see FIG. 1), suggesting that DC-ASGPR contributes to cellular immune responses as well as humoral immune responses. This was tested by a mixed lymphocyte reaction (MLR). Proliferation of purified allogeneic T cells was significantly enhanced by DCs stimulated with mAb specific for DC-ASGPR (FIG. 4A). DCs activated through DC-ASGPR could also prime Mart-1-specific CD8 T cells more efficiently than DC stimulated with control mAb (upper panels in FIG. 4B). More importantly, signaling through DC-ASGPR permitted DCs to cross-prime Mart-1 peptides to CD8 T cells (lower panels in FIG. 4B). This indicates that DC-ASGPR plays an important role in enhancing DC function, resulting in better priming and cross-priming of antigens to CD8 T cells. The role of DC-ASGPR expressed on the mixture of APCs in PBMCs in activation of T cell responses is shown in FIG. 4C where PBMCs stimulated with mAb to DC-ASGPR resulted in an increased frequency of Flu M1 tetramer specific CD8 T cells compared to DCs stimulated with control mAb. This enhanced antigen specific CD8 T cell response was supported by the data in FIG. 4D, showing that DCs stimulated through DC-ASGPR significantly increase CD4 T cell proliferation.

Antibodies and tetramers—Antibodies (Abs) for surface staining of DCs and B cells, including isotype control Abs, were purchased from BD Biosciences (CA). Abs for ELISA were purchased from Bethyl (TX). Anti-BLyS and anti-APRIL were from PeproTech (NJ). Tetramers, HLA-A*0201-GILGFVFTL (SEQ ID NO.: 1) (Flu M1) and HLA-A*0201-ELAGIGILTV (SEQ ID NO.: 2) (Mart-1), were purchased from Beckman Coulter (CA).

Cells and cultures—Monocytes ($1\times10^6$/ml) from normal donors were cultured in Cellgenics (France) media containing GM-CSF (100 ng/ml) and IL-4 (50 ng/ml) (R&D, CA). For day three and day six, DCs, the same amounts of cytokines were supplemented into the media on day one and day three, respectively. B cells were purified with a negative isolation kit (BD). CD4 and CD8 T cells were purified with magnetic beads coated with anti-CD4 or CD8 (Milteniy, Calif.). PBMCs were isolated from Buffy coats using Percoll™ gradients (GE Healthcare UK Ltd, Buckinghamshire, UK) by density gradient centrifugation. For DC activation, $1\times10^5$ DCs were cultured in the mAb-coated 96-well plate for 16-18 h. mAbs (1-2 µg/well) in carbonate buffer, pH 9.4, were incubated for at least 3 h at 37° C. Culture supernatants were harvested and cytokines/chemokines were measured by Luminex (Biorad, Calif.). For gene analysis, DCs were cultured in the plates coated with mAbs for 8 h. In some experiments, soluble 50 ng/ml of CD40L (R&D, CA) or 50 nM CpG (InVivogen, CA) was added into the cultures. In the DCs and B cell co-cultures, $5\times10^3$ DCs resuspended in RPMI 1640 with 10% FCS and antibiotics (Biosource, CA) were first cultured in the plates coated with mAbs for at least 6 h, and then $1\times10^5$ purified autologous B cells labeled with CFSE (Molecular Probes, OR) were added. In some experiments, DCs were pulsed with 5 moi (multiplicity of infection) of heat-inactivated influenza virus (A/PR/8 H1N1) for 2 h, and then mixed with B cells. For the DCs and T cell co-cultures, $5\times10^3$ DCs were cultured with $1\times10^5$ purified autologous CD8 T cells or mixed allogeneic T cells. Allogeneic T cells were pulsed with 1 µCi/well $^3$[H]-thymidine for the final 18 h of incubation, and then cpm were measured by a µ-counter (Wallac, Minn.). $5\times10^5$ PBMCs/well were cultured in the plates coated with mAbs. The frequency of Mart-1 and Flu M1 specific CD8 T cells was measured by staining cells with anti-CD8 and tetramers on day ten and day seven of the cultures, respectively. 10 µM of Mart-1 peptide (ELAGIGILTV) (SEQ ID NO.: 2) and 20 nM of recombinant protein containing Mart-1 peptides (see below) were added to the DC and CD8 T cell cultures. 20 nM purified recombinant Flu M1 protein (see below) was add to the PBMC cultures.

Monoclonal antibodies—Mouse mAbs were generated by conventional technology. Briefly, six-week-old BALB/c mice were immunized i.p. with 20 µg of receptor ectodomain.hIgGFc fusion protein with Ribi adjuvant, then boosts with 20 µg antigen ten days and fifteen days later. After three months, the mice were boosted again three days prior to taking the spleens. Alternately, mice were injected in the footpad with 1-10 µg antigen in Ribi adjuvant every three to four days over a thirty to forty day period. Three to four days after a final boost, draining lymph nodes were harvested. B cells from spleen or lymph node cells were fused with SP2/O-Ag 14 cells. Hybridoma supernatants were screened to analyze Abs to the receptor ectodomain fusion protein compared to the fusion partner alone, or the receptor ectodomain fused to alkaline phosphatase (44). Positive wells were then screened in FACS using 293F cells transiently transfected with expression plasmids encoding full-length receptor cDNAs. Selected hybridomas were single cell cloned and expanded in CELLine flasks (Integra, CA). Hybridoma supernatants were mixed with an equal volume of 1.5 M glycine, 3 M NaCl, 1×PBS, pH 7.8 and tumbled with MabSelect resin. The resin was washed with binding buffer and eluted with 0.1 M glycine, pH 2.7. Following neutralization with 2 M Tris, mAbs were dialyzed versus PBS.

ELISA—Sandwich ELISA was performed to measure total IgM, IgG, and IgA as well as flu-specific immunoglobulins (Igs). Standard human serum (Bethyl) containing known amounts of Igs and human AB serum were used as standard for total Igs and flu-specific Igs, respectively. Flu specific Ab titers, units, in samples were defined as dilution factor of AB serum that shows an identical optical density. The amounts of BAFF and BLyS were measured by ELISA kits (Bender MedSystem, CA).

RNA purification and gene analysis—Total RNA extracted with RNeasy columns (Qiagen), and analyzed with the 2100 Bioanalyser (Agilent). Biotin-labeled cRNA targets were prepared using the Illumina totalprep labeling kit (Ambion) and hybridized to Sentrix Human6 BeadChips (46K transcripts). These microarrays consist of 50mer oligonucleotide probes attached to 3 µm beads which are lodged into microwells etched at the surface of a silicon wafer. After staining with Streptavidin-Cy3, the array surface is imaged using a sub-micron resolution scanner manufactured by Illumina (Beadstation 500X). A gene expression analysis software program, GeneSpring, Version 7.1 (Agilent), was used to perform data analysis.

Expression and purification of recombinant Flu M1 and MART-1 proteins—PCR was used to amplify the ORF of Influenza A/Puerto Rico/8/34/Mount Sinai (H1N1) M1 gene while incorporating an Nhe I site distal to the initiator codon and a Not I site distal to the stop codon. The digested fragment was cloned into pET-28b(+) (Novagen), placing the M1 ORF in-frame with a His6 tag, thus encoding His.Flu M1 protein. A pET28b (+) derivative encoding an N-terminal 169 residue cohesin domain from *C. thermocellum* (unpublished) inserted between the Nco I and Nhe I sites expressed Coh.His. For expression of Cohesin-Flex-hMART-1-PeptideA-His, the sequence GACAC-CACCGAGGCCCGCCACCCCCACCCCCCGTGAC-CACCCCCACCACCACCGA CCGGAAGGGCACCACCACCGCCGAGGAGCTGGCCGG-CATCGGCATCCTGACCGTGATCC TGGGCGGCAAGCGGACCAACAACAGCACCCCCAC-CAAGGGCGAATTCTGCAGATAT CCAT-CACACTGGCGGCCG (SEQ ID NO.: 3) (encoding DTTEARHPHPPVTTPTTDRKGT<u>TAEELAGIGILT-V</u>ILGGKRTNNSTPTKGEFCRYPS<u>HWRP</u> (SEQ ID NO.: 4)—the marked residues are the immunodominant HLA-A2-restricted peptide and the underlined residues surrounding the peptide are from MART-1) was inserted between the Nhe I and Xho I sites of the above vector. The proteins were expressed in *E. coli* strain BL21 (DE3) (Novagen) or T7 Express (NEB), grown in LB at 37° C. with selection for kanamycin resistance (40 µg/ml) and shaking at 200 rounds/min to mid log phase growth when 120 mg/L IPTG was added. After three hours, the cells were harvested by centrifugation and stored at −80° C. *E. coli* cells from each 1 L fermentation were resuspended in 30 ml ice-cold 50 mM Tris, 1 mM EDTA pH 8.0 (buffer B) with 0.1 ml of protease inhibitor Cocktail II (Calbiochem, CA). The cells were sonicated on ice 2×5 min at setting 18 (Fisher Sonic Dismembrator 60) with a 5 min rest period and then spun at 17,000 r.p.m. (Sorvall SA-600) for 20 min at 4° C. For His.Flu M1 purification the 50 ml cell lysate supernatant fraction was passed through 5 ml Q Sepharose beads and 6.25 ml 160 mM Tris, 40 mM imidazole, 4 M NaCl pH 7.9 was added to the Q Sepharose flow through. This was loaded at 4 ml/min onto a 5 ml HiTrap chelating HP column charged with Ni++. The column-bound protein was washed with 20 mM NaPO$_4$, 300 mM NaCl pH 7.6 (buffer D) followed by another wash with 100 mM H$_3$COONa pH 4.0. Bound protein was eluted with 100 mM H$_3$COONa pH 4.0. The peak fractions were pooled and loaded at 4 ml/min onto a 5 ml HiTrap S column equilibrated with 100 mM H$_3$COONa pH 5.5, and washed with the equilibration buffer followed by elution with a gradient from 0-1 M NaCl in 50 mM NaPO$_4$ pH 5.5. Peak fractions eluting at about 500 mM NaCl were pooled. For Coh.Flu M1.His purification, cells from 2 L of culture were lysed as above. After centrifugation, 2.5 ml of Triton X114 was added to the supernatant with incubation on ice for 5 min. After further incubation at 25° C. for 5 min, the supernatant was separated from the Triton X114 following centrifugation at 25° C. The extraction was repeated and the supernatant was passed through 5 ml of Q Sepharose beads and 6.25 ml 160 mM Tris, 40 mM imidazole, 4 M NaCl pH 7.9 was added to the Q Sepharose flow through. The protein was then purified by Ni++ chelating chromatography as described above and eluted with 0-500 mM imidazole in buffer D.

Only particular anti-DC-ASGPR mAbs have DC activation properties—The invention discloses that DC activation is not a general property of anti-DC-ASGPR antibodies, rather only certain anti-DC-ASGPR mAbs have this function. FIG. 5 shows that only certain mAbs activate DCS through the DC-ASGPR, which must be characterized by screening against actual DCs.

Particular sequences corresponding to the L and H variable regions of anti-DC-ASGPR mAbs—The invention encompasses particular amino acid sequences shown below corresponding to anti-DC-ASGPR monoclonal antibodies that are desirable components (in the context of e.g., humanized recombinant antibodies) of therapeutic or protective products. The following are such sequences in the context of chimeric mouse V region—human C region recombinant antibodies.

```
[mAnti-ASGPR_49C11_7H-LV-hIgG4H-C] is
                                            (SEQ ID NO.: 5)
DVQLQESGPDLVKPSQSLSLTCTVTGYSITSGYSWHWIRQFPGNKLEWMGY

ILFSGSTNYNPSLKSRISITRDTSKNQFFLQLNSVTTEDTATYFCARSNYG

SFASWGQGTLVTVSAAKTTGPSVFPLAPCSRSTSESTAALGCLVKDYFPEP

VTVSWNSGALTSGVHTFPAVLQSSGLYSLSSVVTVPSSSLGTKTYTCNVDH

KPSNTKVDKRVESKYGPPCPPCPAPEFEGGPSVFLFPPKPKDTLMISRTPE

VTCVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYSRLT

VDKSRWQEGNVFSCSVMHEALHNHYTQKSLSLSLGKAS.
```

The above sequence is a chimera between the H chain V-region of the mAb 49C11 (shown underlined) and the C region of hIgG4.

```
[mAnti-ASGPR_49C11_7K-LV-hIgGK-C] is the corresponding
L chain chimera -
                                            (SEQ ID NO.: 6)
QIVLTQSPAIMSASPGEKVTMTCSASSSVSHMHWYQQKSGTSPKRWIYDTSRLASGVPA

RFSGSGSGTSYSLTISSMEAEDAATYYCQQWSSHPWSFGGGTKLEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC.

[mAnti-ASGPR_4G2.2_Hv-V-hIgG4H-C] is -
                                            (SEQ ID NO.: 7)
QIQLVQSGPELKKPGETVKISCKASGYTFTNYGMNWVKQVPGKGLRWMGWMDTFTGE

PTYADDFKGRFAFSLETSASTAYLQINSLKNEDTATYFCARGGILRLNYFDYWGQGTTL

TVSSAKTKGPSVFPLAPCSRSTSESTAALGCLVKDYFPEPVTVSWNSGALTSGVHTFPAV

LQSSGLYSLSSVVTVPSSSLGTKTYTCNVDHKPSNTKVDKRVESKYGPPCPPCPAPEFEG

GPSVFLFPPKPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSFFLYSRLTVD

KSRWQEGNVFSCSVMHEALHNHYTQKSLSLSLGKAS.

[mAnti-ASGPR_4G2.2_Kv-V-hIgGK-C] is -
                                            (SEQ ID NO.: 8)
DIQMTQSSSSFSVSLGDRVTITCKASEDIYNRLGWYQQKPGNAPRLLISGATSLETGVPSR

FSGSGSGKDYALSITSLQTEDLATYYCQQCWTSPYTFGGGTKLEIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC.

[mAnti-ASGPR_5F10H-LV-hIgG4H-C] is -
                                            (SEQ ID NO.: 9)
EVQLQQSGPELVKPGASVKMSCKASGYTFTDYYMKWVKQSHGKSLEWIGDINPNYGD

TFYNQKFEGKATLTVDKSSRTAYMQLNSLTSEDSAVYYCGRGDYGYFDVWGAGTTVT

VSSAKTKGPSVFPLAPCSRSTSESTAALGCLVKDYFPEPVTVSWNSGALTSGVHTFPAVL

QSSGLYSLSSVVTVPSSSLGTKTYTCNVDHKPSNTKVDKRVESKYGPPCPPCPAPEFEGG

PSVFLFPPKPKDTLMISRTPEVTCVVVDVSQEDPEVQFNWYVDGVEVHNAKTKPREEQF
```

-continued

NSTYRVVSVLTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFFLYS RLTVDK

SRWQEGNVFSCSVMHEALHNHYTQKSLLSLGKAS.

[mAnti-ASGPR_5F10K-LV-hIgGK-C] is -
(SEQ ID NO.: 10)
DIVMTQSHKFMSTSVGDRVSITCKASQDVGTAVAWYQQKPGQSPKLLIYWASTRHTGV

PDRFTGSSGTDFTLTINNVQSEDLADYFCQQYSSNPYMFGGGTKLEIKRTVAAPSVFIF

PPSDEQLKSGTASVVCLLNNFYPREAKVQWKVDNALQSGNSQESVTEQDSKDSTYSLSS

TLTLSKADYEKHKVYACEVTHQGLSSPVTKSFNRGEC.

[mAnti-ASGPR1H11H-V-hIgG4H-C] is -
(SEQ ID NO.: 11)
QLQQSGPELVKPGASVKISCKTSGYTFTEYTMHWVRQSHGKSLEWIGGINPINGGPTYN

QKFKGKATLTVDKSSSTAYMELRSLTSEDSAVYYCARWDYGSRDVMDYWGQGTSVT

VSSAKTKGPSVFPLAPCSRSTSESTAALGCLVKDYFPEPVTVSWNSGALTSGVHTFPAVL

QSSGLYSLSSVVTVPSSSLGTKTYTCNVDHKPSNTKVDKRVESKYGPPCPPCPAPEFEGG

PSVFLFPPKPKDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFFLYSRLTVDK

SRWQEGNVFSCSVMHEALHNHYTQKSLSLSLGKAS.

[mAnti-ASGPR1H11K-LV-hIgGK-C] is -
(SEQ ID NO.: 12)
NIVMTQSPKSMSMSVGERVTLSCKASENVGTYVSWYQQRPEQSPKLLIYGASNRYTGV

PDRFTGSGSATDFTLTISSVQAEDLADYHCGQTYSYIFTFGSGTKLEIKRTVAAPSVFIFPP

SDEQLKSGTASVVCLLNNFYPREAKVQWKVDNALQSGNSQESVTEQDSKDSTYSLSST

LTLSKADYEKHKVYACEVTHQGLSSPVTKSFNRGEC.

The invention envisions these V-region sequences and related sequences modified by those well versed in the art to e.g., enhance affinity for DC-ASGPR and/or integrated into human V-region framework sequences to be engineered into expression vectors to direct the expression of protein forms that can bind to DC-ASGPR on antigen presenting cells.

Engineered recombinant anti-DC-ASGPR recombinant antibody—antigen fusion proteins ((rAb.antigen) are efficacious prototype vaccines in vitro—Expression vectors can be constructed with diverse protein coding sequence e.g., fused in-frame to the H chain coding sequence. For example, antigens such as Influenza HA5, Influenza M1, HIV gag, or immuno-dominant peptides from cancer antigens, or cytokines, can be expressed subsequently as rAb.antigen or rAb.cytokine fusion proteins, which in the context of this invention, can have utility derived from using the anti-DC-ASGPR V-region sequence to bring the antigen or cytokine (or toxin) directly to the surface of the antigen presenting cell bearing DC-ASGPR. This permits internalization of e.g., antigen—sometimes associated with activation of the receptor and ensuing initiation of therapeutic or protective action (e.g., via initiation of a potent immune response, or via killing of the targeted cell. An exemplative prototype vaccine based on this concept could use a H chain vector such as

[mAnti-ASGPR_5F10H-LV-hIgG4H-C-Flex-FluHA5-1-6xHis] or -

(SEQ ID NO.: 13)

EVQLQQSGPELVKPGASVKMSCKASGYTFTDYYMKWVKQSHGKSLEWIGDI

NPNYGDTFYNQKFEGKATLTVDKSSRTAYMQLNSLTSEDSAVYYCGRGDYG

YFDVWGAGTTVTVSSAKTKGPSVFPLAPCSRSTSESTAALGCLVKDYFPEP

VTVSWNSGALTSGVHTFPAVLQSSGLYSLSSVVTVPSSSLGTKTYTCNVDH

KPSNTKVDKRVESKYGPPCPPCPAPEFEGGPSVFLFPPKPKDTLMISRTPE

VTCVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYSRLT

VDKSRWQEGNVFSCSVMHEALHNHYTQKSLSLSLGKA*SDTTEPATPTTPVT*

*T*DQICIGYHANNSTEQVDTIMEKNVTVTHAQDILEKKHNGKLCDLDGVKPL

ILRDCSVAGWLLGNPMCDEFINVPEWSVIVEKANPVNDLCYPGDFNDYEEL

KHLLSRINHFEKIQIIPKSSWSSHEASLGVSSACPYQGKSSFFRNVVWLIK

KNSTYPTIKRSYNNTNQEDLLVLWGIHHPNDAAEQTKLYQNPTTYISVGTS

TLNQRLVPRIATRSKVNGQSGRMEFFWTILKPNDAINFESNGNFIAPEYAY

KIVKKGDSTIMKSELEYGNCNTKCQTPMGAINSSMPFHNIHPLTIGECPKY

VKSNRLVLAHHHHHH.

The above sequence corresponds to the chimeric H chain shown already fused via a flexible linker sequence (shown italicized) to HA-1 domain of avian Flu HA5 (shown in bold). This can be co-expressed with the corresponding L chain chimeric sequence already shown above. Similarly, the sequence

[mAnti-ASGPR_49C11_7H-LV-hIgG4H-C-Dockerin]
(SEQ ID NO.: 14)
DVQLQESGPDLVKPSQSLSLTCTVTGYSITSGYSWHWIRQFPGNKLEWMGY

ILFSGSTNYNPSLKSRISITRDTSKNQFFLQLNSVTTEDTATYFCARSNYG

SFASWGQGTLVTVSAAKTKGPSVFPLAPCSRSTSESTAALGCLVKDYFPEP

VTVSWNSGALTSGVHTFPAVLQSSGLYSLSSVVTVPSSSLGTKTYTCNVDH

KPSNTKVDKRVESKYGPPCPPCPAPEFEGGPSVFLFPPKPKDTLMISRTPE

VTCVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYSRLT

VDKSRWQEGNVFSCSVMHEALHNHYTQKSLSLSLGKASNSPQNEVLYGDVN

DDGKVNSTDLTLLKRYVLKAVSTLPSSKAEKNADVNRDGRVNSSDVTILSR

YLIRVIEKLPI can be used to express via co-transfection of the corresponding L chain sequence already shown above a rAb.Dockerin fusion protein.

FIG. 5 shows that certain anti-DC-ASGPR mAbs can activate DC. GM-CSF/IL-4. DC were incubated for 24 hrs with one of a panel of 12 pure anti-ASGPR mAbs. Cells were then tested for expression of cell surface CD86 (a DC activation marker) and supernatants were assayed for secreted cytokines. Three mAbs (36, 38, 43) from the anti-ASGPR mAb panel activated DC.

FIG. 6 shows that different antigens can be expressed in the context of a DC-ASGPR rAb. Such an anti-DC-ASGPR rAb.Doc protein can be simply mixed with any Cohesin.fusion protein to assemble a stable non-covalent [rAb.Doc:Coh.fusion] complex that functions just as a rAb.fusion protein. FIG. 6 shows that such a [rAb.Doc:Coh.fusion] complex can focus antigen to the surface of cells expressing DC-ASGPR. The figure also shows anti-DC-ASGPR.Doc:Coh.Flu M1 complexes deliver Flu M1 to the surface of 293F cells transfected with DC-ASGPR cDNA. 1 μg/ml of anti-DC-ASGPR.Doc rAb (shown as the peak on the right) or control hIgG4.Doc rAb (shown as the peak on the left) were incubated with biotinylated Coh.Flu M1 (2 μg/ml) for 1 hr at R.T. transfected 293F cells were added and incubation continued for 20 min on ice. Cells were then washed and stained with PE-labeled streptavidin. Cells were then analyzed for PE fluorescence.

Anti-DC-ASGPR rAb complexed to Flu M1 via Dockerin:Cohesin interaction targets the antigen to human DCs and results in the expansion of Flu M1-specific CD8+ T cells—the potential utility of anti-DC-ASGPR rAbs as devices to deliver antigen to e.g., DC is shown in the figure below. FIG. 7 shows the dramatic expansion of Flu M1-specific CD8+ cells is highly predictive of potency of such an agent as a vaccine directed to eliciting protective immune responses against Flu M1.

FIGS. 8A-8D demonstrated the cross reactivity of the different antibodies with monkey ASGPR. For pIRES_ASGPR-mon (monkey) was cloned by inserting the PCR product into NheI-NotI sites of pIRES vector. The sequence of final product is base on clone 5S10. Most other clones are either similar to this with one aa difference or identical to this. However, one clone, 5S1, has an A deletion near the 3' end, which generated a shortened and different C' terminus and maybe used as a second variant. To clone the monkey ASGPR, the following oligos were used: DC-ASGPR_MoN: gaattcgctagcCACCATGACATAT-GAAAACTTCCAAGACTTGGAGAGTGAG-GAGAAAGTC CAAGGGG (SEQ ID NO.: 15); and DC-ASGPR_Mo: CGAATTCGCGGCCGCTCAGTGACT CTCCTGGCTGGCCTGGGTCAGACCAGCCTCGCA GACCC (SEQ ID NO.: 16), which is a reverse complement of GGGTCTGCGAGGCTGGTCT GACCCAGGCCAGCCAGGAGAGTCACT-GAGCGGCCGCG AATTCG (SEQ ID NO.: 17). Sequence comparisons indicate the likely regions of overlap and, hence, the cross-reactivity, as is known to those if skill in the art.

The following table demonstrated the binding of the DC-ASGPR 334998 200 ug/ml 12.05.07 cfg#558 anti-Human IgG PE

| Glycan number | Glycan name | Avg w/o Max & Min | StDev w/o Max & Min | SEM w/o Max & Min | % CV |
|---|---|---|---|---|---|
| 82 | GalNAcα1-3(Fucα1-2)Galβ1-4GlcNAcμ-Sp8 | 52930 | 10265 | 5132 | 19 |
| 210 | Neu5Acα2-3(GalNAcβ1-4)Galβ1-4GlcNAcβ-Sp8 | 49937 | 4969 | 2484 | 10 |
| 86 | GalNAcα1-3Galβ-Sp8 | 49067 | 4672 | 2336 | 10 |
| 89 | GalNAcβ1-3(Fucα1-2)Galβ-Sp8 | 47375 | 5453 | 2726 | 12 |
| 84 | GalNAcα1-3(Fucα1-2)Galβ-Sp8 | 46555 | 6618 | 3309 | 14 |
| 209 | Neu5Acα2-3(GalNAcβ1-4)Galβ1-4GlcNAcβ-Sp0 | 46169 | 2121 | 1060 | 5 |
| 175 | GlcNAcβ1-6GalNAcα-Sp8 | 44809 | 1939 | 969 | 4 |
| 301 | GalNAcα1-3(Fucα1-2)Galβ-Sp18 | 44147 | 6003 | 3002 | 14 |
| 211 | Neu5Acα2-3(GalNAcβ1-4)Galβ1-4Glcβ-Sp0 | 43603 | 3517 | 1759 | 8 |
| 10 | α-GalNAc-Sp8 | 43514 | 2476 | 1238 | 6 |
| 128 | Galβ1-3GalNAcβ1-4(Neu5Acα2-3)Galβ1-4Glcβ-Sp0 | 43152 | 13339 | 6669 | 31 |
| 151 | Galβ1-4GlcNAcβ1-6GalNAcα-Sp8 | 42871 | 2466 | 1233 | 6 |
| 92 | GalNAcβ1-4GlcNAcβ-Sp0 | 42845 | 3394 | 1697 | 8 |
| 93 | GalNAcβ1-4GlcNAcβ-Sp8 | 41764 | 7340 | 3670 | 18 |
| 87 | GalNAcα1-4(Fucα1-2)Galβ1-4GlcNAcβ-Sp8 | 41584 | 2925 | 1462 | 7 |
| 79 | GalNAcα1-3(Fucα1-2)Galβ1-3GlcNAcβ-Sp0 | 41406 | 14134 | 7067 | 34 |
| 20 | β-GalNAc-Sp8 | 40803 | 2388 | 1194 | 6 |
| 206 | Neu5Acα2-8Neu5Acα2-3(GalNAcβ1-4)Galβ1-4Glcβ-Sp0 | 38720 | 2736 | 1368 | 7 |
| 242 | Neu5Acα2-6GalNAcα-Sp8 | 37500 | 1934 | 967 | 5 |
| 91 | GalNAcβ1-4(Fucα1-3)GlcNAcβ-Sp0 | 37286 | 5046 | 2523 | 14 |

-continued

| Glycan number | Glycan name | Avg w/o Max & Min | StDev w/o Max & Min | SEM w/o Max & Min | % CV |
|---|---|---|---|---|---|
| 204 | Neu5Acα2-8Neu5Acα2-8Neu5Acα2-3(GalNAcβ1-4)Galβ1-4Glcβ-Sp0 | 37237 | 995 | 497 | 3 |
| 203 | NeuAcα2-8NeuAcα2-8NeuAcα2-3(GalNAcβ1-4)Galβ1-4Glcβ-Sp0 | 36746 | 2399 | 1200 | 7 |
| 243 | Neu5Acα2-6GalNAcβ1-4GlcNAcβ-Sp0 | 36375 | 1661 | 830 | 5 |
| 59 | Fucα1-2Galβ1-3GalNAcβ1-4(Neu5Acα2-3)Galβ1-4Glcβ-Sp0 | 35701 | 6903 | 3452 | 19 |
| 90 | GalNAcβ1-3Galα1-4Galβ1-4GlcNAcβ-Sp0 | 34350 | 760 | 380 | 2 |
| 83 | GalNAcα1-3(Fucα1-2)Galβ1-4Glcβ-Sp0 | 28846 | 9844 | 4922 | 34 |
| 302 | GalNAcβ1-3Galβ-Sp8 | 28745 | 15727 | 7864 | 55 |
| 300 | GalNAcα-Sp15 | 18125 | 18847 | 9424 | 104 |
| 127 | Galβ1-3GalNAcβ1-3Galα1-4Galβ1-4Glcβ-Sp0 | 17999 | 9798 | 4899 | 54 |
| 85 | GalNAcα1-3GalNAcβ-Sp8 | 12643 | 10843 | 5422 | 86 |
| 173 | GlcNAcβ1-4GlcNAcβ1-4GlcNAcβ-Sp8 | 8673 | 940 | 470 | 11 |
| 81 | GalNAcα1-3(Fucα1-2)Galβ1-4GlcNAcβ-Sp0 | 7672 | 12937 | 6469 | 169 |
| 30 | [3OSO3]Galβ1-4(6OSO3)Glcβ-Sp8 | 7394 | 292 | 146 | 4 |
| 120 | Galβ1-3(Galβ1-4GlcNAcβ1-6)GalNAcα-Sp8 | 5664 | 1311 | 655 | 23 |
| 80 | GalNAcα1-3(Fucα1-2)Galβ1-4(Fucα1-3)GlcNAcβ-Sp0 | 5444 | 907 | 454 | 17 |
| 147 | Galβ1-4GlcNAcβ1-3Galβ1-4GlcNAcβ-Sp0 | 4927 | 410 | 205 | 8 |
| 29 | [3OSO3]Galβ1-4(6OSO3)Glcβ-Sp0 | 4871 | 908 | 454 | 19 |
| 101 | Galα1-3GalNAcα-Sp8 | 4815 | 3163 | 1581 | 66 |
| 214 | Neu5Acα2-3GalNAcα-Sp8 | 4109 | 569 | 284 | 14 |
| 287 | [3OSO3][4OSO3]Galβ1-4GlcNacβ-SpSp0 | 3959 | 1646 | 823 | 42 |
| 40 | [4OSO3]Galβ1-4GlcNAcβ-Sp8 | 3848 | 673 | 337 | 17 |
| 45 | [6OSO3]Galβ1-4[6OSO3]Glcβ-Sp8 | 3790 | 993 | 497 | 26 |
| 166 | GlcNAcβ1-3Galβ1-4GlcNAcβ1-3Galβ1-4GlcNAcβ-SpO | 3720 | 435 | 218 | 12 |
| 227 | Neu5Acα2-3Galβ1-4[6OSO3]GlcNAcβ-Sp8 | 3576 | 793 | 397 | 22 |
| 218 | NeuAcα2-3Galβ1-3(Fucα1-4)GlcNAcβ1-3Galβ1-4(Fucα1-3)GlcNAcβSp0 | 3360 | 104 | 52 | 3 |
| 240 | Neu5Acα2-3Galβ1-4Glcβ-Sp8 | 3313 | 976 | 488 | 29 |
| 149 | Galβ1-4GlcNAcβ1-3Galβ1-4Glcβ-Sp8 | 3233 | 263 | 132 | 8 |
| 244 | Neu5Acα2-6Galβ1-4[6OSO3]GlcNAcβ-Sp8 | 3195 | 757 | 379 | 24 |
| 270 | Fucα1-2Galβ1-4[6OSO3]GlcNAc-Sp8 | 3161 | 2563 | 1282 | 81 |
| 42 | [6OSO3]Galβ1-4Glcβ-Sp0 | 3084 | 529 | 264 | 17 |
| 271 | Fucα1-2[6OSO3]Galβ1-4[6OSO3]Glc-Sp0 | 3063 | 377 | 188 | 12 |
| 172 | (GlcNAcβ1-4)5β-Sp8 | 3032 | 1058 | 529 | 35 |
| 47 | [6OSO3]GlcNAcβ-Sp8 | 3008 | 159 | 80 | 5 |
| 143 | Neu5Acα2-3Galβ1-4GlcNAcβ1-2Manα13(Neu5Acα2-3Galβ1-4GlcNAcβ1-2Manα1-6)Manβ1-4GlcNAcβ1-4GlcNAcβ-Sp12 | 3008 | 309 | 155 | 10 |
| 265 | [3OSO3]Galβ1-4(Fucα1-3)(6OSO3)Glc-Sp0 | 2995 | 1841 | 921 | 61 |
| 139 | Galβ1-4[6OSO3]Glcβ-Sp0 | 2988 | 1070 | 535 | 36 |
| 27 | [3OSO3][6OSO3]Galβ1-4GlcNAcβ-Sp0 | 2930 | 317 | 158 | 11 |
| 273 | Fucα1-2-Galβ1-4[6OSO3]Glc-Sp0 | 2919 | 495 | 247 | 17 |
| 319 | Neu5Acα2-6Galβ1-4GlcNAcβ1-2Manα1-3(Galβ1-4GlcNAcβ1-2Manα1-6)Manβ1-4GlcNAcβ1-4GlcNAcβ-Sp12 | 2730 | 993 | 497 | 36 |
| 35 | [3OSO3]Galβ1-4[6OSO3]GlcNAcβ-Sp8 | 2722 | 516 | 258 | 19 |
| 28 | [3OSO3]Galβ1-4Glcβ-Sp8 | 2674 | 197 | 98 | 7 |
| 38 | [3OSO3]Galβ-Sp8 | 2652 | 1680 | 840 | 63 |
| 253 | Neu5Acα2-8Neu5Acα2-3Galβ1-4Glcβ-Sp0 | 2631 | 1136 | 568 | 43 |
| 289 | 6-H2PO3Glcβ-Sp10 | 2611 | 674 | 337 | 26 |
| 26 | [3OSO3][6OSO3]Galβ1-4GlcNAcβ-SpO | 2550 | 153 | 76 | 6 |
| 266 | [3OSO3]Galβ1-4(Fucα1-3)Glc-Sp0 | 2529 | 444 | 222 | 18 |
| 54 | Neu5Acα2-6Galβ1-4GlcNAcβ1-2Manα1-3(Neu5Acα2-6Galβ1-4GlcNAcβ1-2Manα1-6)Manβ1-4GlcNAcβ1-4GlcNAcβ-Sp8 | 2476 | 300 | 150 | 12 |
| 303 | GlcAβ1-3GlcNAcβ-Sp8 | 2463 | 130 | 65 | 5 |
| 32 | [3OSO3]Galβ1-3GalNAcα-Sp8 | 2461 | 622 | 311 | 25 |
| 53 | Neu5Acα2-6Galβ1-4GlcNAcβ1-2Manα1-3(Neu5Acα2-6Galβ1-4GlcNAcβ1-2Manα1-6)Manβ1-4GlcNAcβ1-4GlcNAcβ-Sp13 | 2455 | 283 | 142 | 12 |
| 181 | Glcβ1-6Glcβ-Sp8 | 2455 | 154 | 77 | 6 |
| 267 | [3OSO3]Galβ1-4[Fucα1-3][6OSO3]GlcNAc-Sp8 | 2447 | 1065 | 532 | 44 |
| 293 | Galβ1-3(Neu5Acα2-3Galβ1-4(Fucα1-3)GlcNAcβ1-6)GalNAc-Sp14 | 2359 | 648 | 324 | 27 |
| 202 | Neu5Acα2-3Galβ1-3GalNAcα-Sp8 | 2349 | 928 | 464 | 40 |
| 163 | GlcNAcβ1-3Galβ1-3GalNAcα-Sp8 | 2347 | 375 | 188 | 16 |
| 1 | Neu5Acα2-8Neu5Acα-Sp8 | 2339 | 1539 | 769 | 66 |
| 31 | [3OSO3]Galβ1-3(Fucα1-4)GlcNAcβ-Sp8 | 2332 | 319 | 160 | 14 |
| 230 | Neu5Acα2-3Galβ1-4(Fucα1-3)GlcNAcβ-Sp0 | 2306 | 164 | 82 | 7 |
| 286 | [3OSO3]Galβ1-4[6OSO3]GlcNAβ-Sp0 | 2290 | 472 | 236 | 21 |
| 318 | Neu5Acα2-3Galβ1-4GlcNAcβ1-2Manα1-3(Neu5Acα2-6Galβ1-4GlcNAcβ1-2Manα1-6)Manβ1-4GlcNAcβ1-4GlcNAcβ-Sp12 | 2262 | 246 | 123 | 11 |

-continued

| Glycan number | Glycan name | Avg w/o Max & Min | StDev w/o Max & Min | SEM w/o Max & Min | % CV |
|---|---|---|---|---|---|
| 199 | Neu5Acα2-6Galβ1-4GlcNAcβ1-2Manα1-3(Neu5Acα2-3Galβ1-4GlcNAcβ1-2Manα1-6)Manβ1-4GlcNAcβ1-4GlcNAcβ-Sp12 | 2217 | 138 | 69 | 6 |
| 39 | [4OSO3][6OSO3]Galβ1-4GlcNAcβ-Sp0 | 2215 | 619 | 310 | 28 |
| 77 | Fucα1-4GlcNAcβ-Sp8 | 2207 | 83 | 42 | 4 |
| 285 | Neu5Acα2-3Galβ1-4GlcNAcβ1-3Galβ1-3GlcNAcβ-Sp0 | 2193 | 1679 | 839 | 77 |
| 262 | Neu5Gcα2-6GalNAcα-Sp0 | 2192 | 734 | 367 | 33 |
| 216 | Neu5Acα2-3Galβ1-3(6OSO3)GlcNAc-Sp8 | 2163 | 1062 | 531 | 49 |
| 43 | [6OSO3]Galβ1-4Glcβ-Sp8 | 2149 | 700 | 350 | 33 |
| 297 | Galβ1-4GlcNAcβ1-3(GlcNAcβ1-6)Galβ1-4GlcNAc-Sp0 | 2141 | 983 | 491 | 46 |
| 224 | NeuAcα2-3Galβ1-3GlcNAcβ1-3Galβ1-4GlcNAcβ-Sp0 | 2133 | 1208 | 604 | 57 |
| 3 | Neu5Acα2-8Neu5Acα2-8Neu5Acβ-Sp8 | 2117 | 611 | 306 | 29 |
| 171 | (GlcNAcβ1-4)6β-Sp8 | 2112 | 302 | 151 | 14 |
| 316 | Neu5Acα2-3Galβ1-3(Neu5Acα2-6)GalNAc-Sp14 | 2105 | 1171 | 585 | 56 |
| 15 | α-Neu5Ac-Sp11 | 2099 | 250 | 125 | 12 |
| 52 | Galβ1-4GlcNAcβ1-2Manα1-3 (Galβ1-4GlcNAcβ1-2Manα1-6)Manβ1-4GlcNAcβ1-4GlcNAcβ-Sp13 | 2092 | 429 | 215 | 21 |
| 268 | [3OSO3]Galβ1-4[Fucα1-3]GlcNAc-Sp0 | 2085 | 955 | 477 | 46 |
| 313 | Manα1-2Manα1-2Manα1-3(Manα1-2Manα1-6(Manα1-3)Manα1-6)Manα-Sp9 | 2020 | 812 | 406 | 40 |
| 225 | Neu5Acα2-3Galβ1-3GlcNAcβ-Sp0 | 2019 | 1052 | 526 | 52 |
| 36 | [3OSO3]Galβ1-4GlcNAcβ-Sp0 | 2012 | 389 | 194 | 19 |
| 263 | Neu5Gcα2-6Galβ1-4GlcNAcβ-Sp0 | 1999 | 664 | 332 | 33 |
| 141 | Galβ1-4GalNAcα1-3(Fucα1-2)Galβ1-4GlcNAcβ-Sp8 | 1968 | 772 | 386 | 39 |
| 274 | Galβ1-3(Fucα1-4)GlcNAcβ1-3Galβ1-3(Fucα1-4)GlcNAcβ-Sp0 | 1961 | 78 | 39 | 4 |
| 275 | Galβ1-3-(Galβ1-4GlcNacβ1-6)GalNAc-Sp14 | 1953 | 409 | 205 | 21 |
| 7 | α-D-Gal-Sp8 | 1925 | 636 | 318 | 33 |
| 41 | 6-H2PO3Manα-Sp8 | 1919 | 223 | 111 | 12 |
| 247 | Neu5Acα2-6Galβ1-4GlcNAcβ1-3Galβ1-4(Fucα1-3)GlcNAcβ1-3Galβ1-4(Fucα1-3)GlcNAcβ-Sp0 | 1914 | 169 | 85 | 9 |
| 311 | Manα1-6Manβ-Sp10 | 1906 | 522 | 261 | 27 |
| 205 | Neu5Acα2-8Neu5Acα2-8Neu5Acα2-3Galβ1-4Glcβ-Sp0 | 1902 | 222 | 111 | 12 |
| 280 | Galβ1-4[Fucα1-3][6OSO3]GlcNAc-Sp0 | 1881 | 982 | 491 | 52 |
| 152 | Galβ1-4GlcNAcβ-Sp0 | 1868 | 924 | 462 | 49 |
| 113 | Galα1-6Glcβ-Sp8 | 1864 | 321 | 161 | 17 |
| 115 | Galβ1-3(Fucα1-4)GlcNAcβ1-3Galβ1-4(Fucα1-3)GlcNAcβ-Sp0 | 1855 | 338 | 169 | 18 |
| 251 | Neu5Acα2-6Galβ-Sp8 | 1842 | 316 | 158 | 17 |
| 116 | Galβ1-3(Fucα1-4)GlcNAcβ1-3Galβ1-4GlcNAcβ-Sp0 | 1836 | 798 | 399 | 43 |
| 194 | Manα1-2Manα1-2Manα1-3(Manα1-2Manα1-3(Manα1-2Manα1-6)Manα1-6)Manβ1-4GlcNAcβ1-4GlcNAcβ-Sp12 | 1829 | 176 | 88 | 10 |
| 33 | [3OSO3]Galβ1-3GlcNAcβ-Sp8 | 1812 | 889 | 445 | 49 |
| 272 | Fucα1-2-(6OSO3)-Galβ1-4Glc-Sp0 | 1805 | 86 | 43 | 5 |
| 207 | Neu5Acα2-8Neu5Acα2-8Neu5Acα-Sp8 | 1804 | 454 | 227 | 25 |
| 74 | Fucα1-2Galβ-Sp8 | 1796 | 648 | 324 | 36 |
| 213 | Neu5Acα2-3(Neu5Acα2-6)GalNAcα-Sp8 | 1768 | 312 | 156 | 18 |
| 234 | Neu5Acα2-3Galβ1-4GlcNAcβ1-3Galβ1-4(Fucα1-3)GlcNAc-Sp0 | 1767 | 178 | 89 | 10 |
| 50 | Manα1-3(Manα1-6)Manβ1-4GlcNAcβ1-4GlcNAcβ-Sp13 | 1759 | 553 | 277 | 31 |
| 111 | Galα1-4Galβ1-4Glcβ-Sp0 | 1740 | 635 | 318 | 36 |
| 291 | Galα1-3GalNAcα-Sp16 | 1738 | 1090 | 545 | 63 |
| 296 | Galβ1-4GlcNAcβ1-3(Galβ1-4GlcNAcβ1-6)Galβ1-4GlcNAc-Sp0 | 1726 | 850 | 425 | 49 |
| 154 | Galβ1-4Glcβ-Sp0 | 1725 | 457 | 229 | 27 |
| 56 | Fucα1-2Galβ1-3GalNAcβ1-3Galα1-4Galβ1-4Glcβ-Sp9 | 1719 | 384 | 192 | 22 |
| 66 | Fucα1-2Galβ1-4(Fucα1-3)GlcNAcβ1-3Galβ1-4(Fucα1-3)GlcNAcβ1-3Galβ1-4(Fucα1-3)GlcNAcβ-Sp0 | 1703 | 224 | 112 | 13 |
| 299 | Galβ1-4GlcNAcβ1-6Galβ1-4GlcNAcβ-Sp0 | 1658 | 820 | 410 | 49 |
| 44 | [6OSO3]Galβ1-4GlcNAcβ-Sp8 | 1632 | 242 | 121 | 15 |
| 237 | Neu5Acα2-3Galβ1-4GlcNAcβ-Sp8 | 1632 | 1049 | 524 | 64 |
| 233 | Neu5Acα2-3Galβ1-4(Fucα1-3)GlcNAcβ1-3Galβ1-4GlcNAcβ-Sp8 | 1620 | 862 | 431 | 53 |
| 192 | Manα1-6(Manα1-2Manα1-3)Manα1-6(Manα2Manα1-3)Manβ1-4GlcNAcβ1-4GlcNAcβ-Sp12 | 1608 | 903 | 452 | 56 |
| 64 | Fucα1-2Galβ1-3GlcNAcβ-Sp8 | 1602 | 625 | 313 | 39 |
| 62 | Fucα1-2Galβ1-4Galβ1-3Galβ1-4Glcβ-Sp8 | 1580 | 417 | 208 | 26 |
| 148 | Galβ1-4GlcNAcβ1-3Galβ1-4Glcβ-Sp0 | 1568 | 617 | 308 | 39 |
| 295 | Galβ1-4GlcNAcβ1-2Manα1-3(Neu5Acα2-6Galβ1-4GlcNAcβ1-2Manα1-6)Manβ1-4GlcNAcβ1-4GlcNAcβ-Sp12 | 1556 | 190 | 95 | 12 |
| 137 | Galβ1-4(Fucα1-3)GlcNAcβ1-4Galβ1-4(Fucα1-3)GlcNAcβ-Sp0 | 1552 | 1313 | 656 | 85 |
| 17 | β-D-Gal-Sp8 | 1544 | 871 | 435 | 56 |
| 168 | GlcNAcβ1-4MDPLys | 1542 | 345 | 172 | 22 |

-continued

| Glycan number | Glycan name | Avg w/o Max & Min | StDev w/o Max & Min | SEM w/o Max & Min | % CV |
|---|---|---|---|---|---|
| 254 | Neu5Acβ2-6GalNAcα-Sp8 | 1541 | 688 | 344 | 45 |
| 231 | Neu5Acα2-3Galβ1-4(Fucα1-3)GlcNAcβ-Sp8 | 1534 | 257 | 129 | 17 |
| 125 | Galβ1-3GalNAcα-Sp8 | 1483 | 1025 | 512 | 69 |
| 269 | Fucα1-2[6OSO3]Galβ1-4GlcNAc-Sp0 | 1473 | 191 | 96 | 13 |
| 182 | G-ol-Sp8 | 1471 | 264 | 132 | 18 |
| 37 | [3OSO3]Galβ1-4GlcNAcβ-Sp8 | 1462 | 1187 | 593 | 81 |
| 229 | Neu5Acα2-3Galβ1-4(Fucα1-3)GlcNAcβ1-3Galβ1-4(Fucα1-3)GlcNAcβ1-4(Fucα1-3)GlcNAcβ-Sp0 | 1451 | 333 | 167 | 23 |
| 315 | Neu5Acα2-3Galβ1-3(Neu5Acα2-3Galβ1-4GlcNAcβ1-6)GalNAc-Sp14 | 1448 | 1476 | 738 | 102 |
| 65 | Fucα1-2Galβ1-4(Fucα1-3)GlcNAcβ1-3Galβ1-4(Fucα1-3)GlcNAcβ-Sp0 | 1442 | 748 | 374 | 52 |
| 164 | GlcNAcβ1-3Galβ1-4GlcNAcβ-Sp0 | 1436 | 1332 | 666 | 93 |
| 305 | GlcNAcβ1-2Manα1-3(GlcNAcβ1-2Manα1-6)Manβ1-4GlcNAcβ1-4GlcNAcβ-Sp12 | 1428 | 288 | 144 | 20 |
| 304 | GlcNAcβ1-2Manα1-3(Neu5Acα2-6Galβ1-4GlcNAcβ1-2Manα1-6)Manβ1-4GlcNAcβ1-4GlcNAcβ-Sp12 | 1428 | 499 | 249 | 35 |
| 145 | Galβ1-4GlcNAcβ1-3Galβ1-4(Fucα1-3)GlcNAcβ1-3Galβ1-4(Fucα1-3)GlcNAcβ-Sp0 | 1422 | 323 | 162 | 23 |
| 117 | Galβ1-3(Fucα1-4)GlcNAc-Sp0 | 1407 | 681 | 341 | 48 |
| 193 | Manα1-2Manα1-6(Manα1-3)Manα1-6(Manα2Manα2Manα1-3)Manβ1-4GlcNAcβ1-4GlcNAcβ-Sp12 | 1404 | 285 | 142 | 20 |
| 19 | β-D-Man-Sp8 | 1389 | 635 | 317 | 46 |
| 176 | GlcNAcβ1-6Galβ1-4GlcNAcβ-Sp8 | 1383 | 1000 | 500 | 72 |
| 232 | Neu5Acα2-3Galβ1-4(Fucα1-3)GlcNAcβ1-3Galβ-Sp8 | 1355 | 374 | 187 | 28 |
| 219 | Neu5Acα2-3Galβ1-3(Neu5Acα2-3Galβ1-4)GlcNAcβ-Sp8 | 1350 | 753 | 377 | 56 |
| 123 | Galβ1-3(Neu5Acβ2-6)GalNAcα-Sp8 | 1350 | 852 | 426 | 63 |
| 276 | Galβ1-3(GlcNacβ1-6)GalNAc-Sp14 | 1345 | 353 | 176 | 26 |
| 208 | Neu5Acα2-3(6-O-Su)Galβ1-4(Fucα1-3)GlcNAcβ-Sp8 | 1341 | 642 | 321 | 48 |
| 55 | Fucα1-2Galβ1-3GalNAcβ1-3Galα-Sp9 | 1331 | 466 | 233 | 35 |
| 257 | Neu5Gcα2-3Galβ1-3(Fucα1-4)GlcNAcβ-Sp0 | 1315 | 108 | 54 | 8 |
| 201 | Fucα1-3(Galβ1-4)GlcNAcβ1-2Manα1-3(Galβ1-4)GlcNAcβ1-2Manα1-6)Manβ1-4GlcNAcβ1-4GlcNAcβ-Sp20 | 1294 | 289 | 144 | 22 |
| 97 | Galα1-3(Fucα1-2)Galβ1-4GlcNAc-Sp0 | 1282 | 583 | 291 | 45 |
| 150 | Galβ1-4GlcNAcβ1-6(Galβ1-3)GalNAcα-Sp8 | 1265 | 778 | 389 | 62 |
| 60 | Fucα1-2Galβ1-3GalNAcβ1-4(Neu5Acα2-3)Galβ1-4Glcβ-Sp9 | 1261 | 738 | 369 | 59 |
| 317 | Neu5Acα2-3Galβ1-3GalNAc-Sp14 | 1239 | 780 | 390 | 63 |
| 23 | β-GlcN(Gc)-Sp8 | 1219 | 436 | 218 | 36 |
| 279 | Galβ1-3GlcNAcβ1-3Galβ1-3GlcNAcβ-Sp0 | 1219 | 570 | 285 | 47 |
| 190 | Manα1-2Manα1-3(Manα1-2Manα1-6)Manα-Sp9 | 1217 | 1305 | 653 | 107 |
| 178 | Glcα1-4Glcα-Sp8 | 1216 | 560 | 280 | 46 |
| 146 | Galβ1-4GlcNAcβ1-3Galβ1-4GlcNAcβ1-3Galβ1-4GlcNAcβ-Sp0 | 1211 | 1315 | 658 | 109 |
| 292 | Galβ1-3GalNAcα-Sp16 | 1198 | 370 | 185 | 31 |
| 221 | Neu5Acα2-3Galβ1-3(Neu5Acα2-6)GalNAcα-Sp8 | 1194 | 238 | 119 | 20 |
| 99 | Galα1-3(Fucα1-2)Galβ-Sp8 | 1189 | 767 | 383 | 64 |
| 309 | HOOC(CH3)CH-3-O-GlcNAcβ1-4GlcNAcβ-Sp10 | 1186 | 1108 | 554 | 93 |
| 248 | Neu5Acα2-6Galβ1-4GlcNAcβ1-3Galβ1-4GlcNAcβ-Sp0 | 1181 | 334 | 167 | 28 |
| 107 | Galα1-3Galβ-Sp8 | 1148 | 688 | 344 | 60 |
| 236 | Neu5Acα2-3Galβ1-4GlcNAcβ-Sp0 | 1148 | 441 | 220 | 38 |
| 320 | Neu5Acα2-6Galβ1-4GlcNAcβ1-2Manα1-3(GlcNAcβ1-2Manα1-6)Manβ1-4GlcNAcβ1-4GlcNAcβ-Sp12 | 1142 | 55 | 27 | 5 |
| 197 | Manα1-6(Manα1-3)Manα1-6(Manα2Manα1-3)Manβ1-4GlcNAcβ1-4GlcNAcβ-Sp12 | 1134 | 200 | 100 | 18 |
| 185 | GlcAβ1-3Galβ-Sp8 | 1133 | 470 | 235 | 42 |
| 34 | [3OSO3]Galβ1-4(Fucα1-3)GlcNAcβ-Sp8 | 1117 | 980 | 490 | 88 |
| 109 | Galα1-4Galβ1-4GlcNAcβ-Sp0 | 1094 | 499 | 250 | 46 |
| 235 | Neu5Acα2-3Galβ1-4GlcNAcβ1-3Galβ1-4GlcNAcβ1-3Galβ1-4GlcNAcβ-Sp0 | 1092 | 1077 | 539 | 99 |
| 228 | Neu5Acα2-3Galβ1-4(Fucα1-3)(6OSO3)GlcNAcβ-Sp8 | 1090 | 771 | 385 | 71 |
| 184 | GlcAβ-Sp8 | 1072 | 476 | 238 | 44 |
| 282 | Galβ1-4(Fucα1-3)GlcNAcβ1-3Galβ1-3(Fucα1-4)GlcNAcβ-Sp0 | 1062 | 239 | 120 | 23 |
| 2 | Neu5Acα2-8Neu5Acβ-Sp17 | 1060 | 84 | 42 | 8 |
| 174 | GlcNAcβ1-6(Galβ1-3)GalNAcα-Sp8 | 1039 | 913 | 456 | 88 |
| 261 | Neu5Gcα2-3Galβ1-4Glcβ-Sp0 | 1034 | 440 | 220 | 43 |
| 18 | β-D-Glc-Sp8 | 1024 | 335 | 167 | 33 |
| 217 | Neu5Acα2-3Galβ1-3(Fucα1-4)GlcNAcβ-Sp8 | 1023 | 646 | 323 | 63 |
| 260 | Neu5Gcα2-3Galβ1-4GlcNAcβ-Sp0 | 1020 | 208 | 104 | 20 |
| 104 | Galα1-3Galβ1-3GlcNAcβ-Sp0 | 1017 | 297 | 149 | 29 |
| 245 | Neu5Acα2-6Galβ1-4GlcNAcβ-Sp0 | 1010 | 394 | 197 | 39 |

-continued

| Glycan number | Glycan name | Avg w/o Max & Min | StDev w/o Max & Min | SEM w/o Max & Min | % CV |
|---|---|---|---|---|---|
| 14 | α-Neu5Ac-Sp8 | 998 | 1046 | 523 | 105 |
| 283 | Galβ1-4GlcNAcβ1-3Galβ1-3GlcNAcβ-Sp0 | 978 | 514 | 257 | 53 |
| 156 | GlcNAcα1-3Galβ1-4GlcNAcβ-Sp8 | 969 | 276 | 138 | 29 |
| 310 | Manα1-3(Manα1-6)Manβ1-4GlcNAcβ1-4GlcNAcβ-Sp12 | 965 | 238 | 119 | 25 |
| 183 | GlcAa-Sp8 | 960 | 463 | 232 | 48 |
| 138 | Galβ1-4(Fucα1-3)GlcNAcβ1-4Galβ1-4(Fucα1-3)GlcNAcβ1-4Galβ1-4(Fucα1-3)GlcNAcβ-Sp0 | 948 | 595 | 297 | 63 |
| 96 | Galα1-3(Fucα1-2)Galβ1-4(Fucα1-3)GlcNAcβ-Sp0 | 948 | 260 | 130 | 27 |
| 6 | Neu5Acα2-6Galβ1-4GlcNAcβ1-2Manα1-3(Neu5Acα2-6Galβ1-4GlcNAcβ1-2Manα1-6)Manβ1-4GlcNAcβ1-4GlcNAcβ-Sp12 | 943 | 351 | 176 | 37 |
| 306 | GlcNAcβ1-3Man-Sp10 | 938 | 153 | 77 | 16 |
| 121 | Galβ1-3(GlcNAcβ1-6)GalNAcα-Sp8 | 936 | 748 | 374 | 80 |
| 258 | Neu5Gcα2-3Galβ1-3GlcNAcβ-Sp0 | 932 | 375 | 188 | 40 |
| 246 | Neu5Acα2-6Galβ1-4GlcNAcβ-Sp8 | 931 | 635 | 317 | 68 |
| 200 | Manβ1-4GlcNAcβ-Sp0 | 920 | 322 | 161 | 35 |
| 78 | Fucβ1-3GlcNAc-Sp8 | 911 | 464 | 232 | 51 |
| 94 | Galα1-2Galβ-Sp8 | 911 | 393 | 197 | 43 |
| 256 | Galβ1-4GlcNAcβ1-2Manα1-3 (Neu5Acα2-6Galβ1-4GlcNAcβ1-2Manα1-6)Manβ1-4GlcNAcβ1-4GlcNAcβ-Sp21 | 909 | 428 | 214 | 47 |
| 95 | Galα1-3(Fucα1-2)Galβ1-3GlcNAcβ-Sp0 | 908 | 245 | 123 | 27 |
| 8 | α-D-Glc-Sp8 | 904 | 417 | 209 | 46 |
| 103 | Galα1-3Galβ1-4(Fucα1-3)GlcNAcβ-Sp8 | 893 | 445 | 222 | 50 |
| 118 | Galβ1-3(Fucα1-4)GlcNAc-Sp8 | 890 | 624 | 312 | 70 |
| 9 | α-D-Man-Sp8 | 881 | 403 | 201 | 46 |
| 16 | β-Neu5Ac-Sp8 | 876 | 935 | 468 | 107 |
| 119 | Galβ1-3(Fucα1-4)GlcNAcβ-Sp8 | 872 | 283 | 141 | 32 |
| 278 | Galβ1-3GalNAc-Sp14 | 851 | 144 | 72 | 17 |
| 187 | KDNα2-3Galβ1-3GlcNAcβ-Sp0 | 839 | 386 | 193 | 46 |
| 69 | Fucα1-2Galβ1-4GlcNAcβ1-3Galβ1-4GlcNAc-Sp0 | 837 | 328 | 164 | 39 |
| 76 | Fucα1-3GlcNAcβ-Sp8 | 836 | 276 | 138 | 33 |
| 108 | Galα1-4(Fucα1-2)Galβ1-4GlcNAcβ-Sp8 | 819 | 58 | 29 | 7 |
| 212 | NeuAcα2-3(NeuAcα2-3Galβ1-3GalNAcβ1-4)Galβ1-4Glcβ-Sp0 | 818 | 1442 | 721 | 176 |
| 132 | Galβ1-3GlcNAcβ1-3Galβ1-4Glcβ-Sp10 | 816 | 353 | 176 | 43 |
| 105 | Galα1-3Galβ1-4GlcNAcβ-Sp8 | 806 | 184 | 92 | 23 |
| 308 | GlcNAcβ1-4GlcNAcβ-Sp12 | 796 | 360 | 180 | 45 |
| 160 | GlcNAcβ1-3(GlcNAcβ1-6)Galβ1-4GlcNAcβ-Sp8 | 794 | 416 | 208 | 52 |
| 284 | Neu5Acα2-3Galβ1-3GlcNAcβ1-3Galβ1-3GlcNAcβ-Sp0 | 777 | 491 | 245 | 63 |
| 188 | KDNα2-3Galβ1-4GlcNAcβ-Sp0 | 774 | 320 | 160 | 41 |
| 215 | Neu5Acα2-3GalNAcβ1-4GlcNAcβ-Sp0 | 762 | 252 | 126 | 33 |
| 294 | Galβ1-3Galβ1-4GlcNAcβ-Sp8 | 746 | 255 | 128 | 34 |
| 196 | Manα1-3(Manα1-2Manα1-6)Manα-Sp9 | 744 | 177 | 88 | 24 |
| 189 | Manα1-2Manα1-2Manα1-3Manα-Sp9 | 743 | 207 | 103 | 28 |
| 25 | GlcNAcβ1-3(GlcNAcβ1-4)(GlcNAcβ1-6)GlcNAc-Sp8 | 735 | 270 | 135 | 37 |
| 131 | Galβ1-3GlcNAcβ1-3Galβ1-4GlcNAcβ-Sp0 | 728 | 290 | 145 | 40 |
| 277 | Galβ1-3-(Neu5Aα2-3Galβ1-4GlcNacβ1-6)GalNAc-Sp14 | 722 | 324 | 162 | 45 |
| 136 | Galβ1-4(Fucα1-3)GlcNAcβ-Sp8 | 718 | 93 | 46 | 13 |
| 70 | Fucα1-2Galβ1-4GlcNAcβ1-3Galβ1-4GlcNAcβ1-3Galβ1-4GlcNAcβ-Sp0 | 713 | 861 | 430 | 121 |
| 110 | Galα1-4Galβ1-4GlcNAcβ-Sp8 | 712 | 183 | 91 | 26 |
| 129 | Galβ1-3GalNAcβ1-4Galβ1-4Glcβ-Sp8 | 702 | 224 | 112 | 32 |
| 71 | Fucα1-2Galβ1-4GlcNAcβ-Sp0 | 686 | 160 | 80 | 23 |
| 169 | GlcNAcβ1-4(GlcNAcβ1-6)GalNAcα-Sp8 | 686 | 229 | 115 | 33 |
| 122 | Galβ1-3(Neu5Acα2-6)GalNAcα-Sp8 | 679 | 157 | 79 | 23 |
| 106 | Galα1-3Galβ1-4Glcβ-Sp0 | 678 | 137 | 69 | 20 |
| 255 | Neu5Acβ2-6Galβ1-4GlcNAcβ-Sp8 | 671 | 153 | 76 | 23 |
| 130 | Galβ1-3Galβ-Sp8 | 668 | 285 | 143 | 43 |
| 144 | Galβ1-4GlcNAcβ1-3GalNAcα-Sp8 | 663 | 227 | 113 | 34 |
| 13 | α-L-Rhα-Sp8 | 662 | 245 | 123 | 37 |
| 22 | β-GlcNAc-Sp8 | 655 | 313 | 157 | 48 |
| 72 | Fucα1-2Galβ1-4GlcNAcβ-Sp8 | 646 | 95 | 47 | 15 |
| 157 | GlcNAcα1-6Galβ1-4GlcNAcβ-Sp8 | 644 | 323 | 162 | 50 |
| 307 | GlcNAcβ1-3GlcNAcβ-Sp10 | 640 | 336 | 168 | 53 |
| 180 | Glcβ1-4Glcβ-Sp8 | 608 | 316 | 158 | 52 |
| 191 | Manα1-2Manα1-3Manα-Sp9 | 607 | 104 | 52 | 17 |
| 134 | Galβ1-3GlcNAcβ-Sp8 | 603 | 103 | 51 | 17 |
| 21 | β-GlcNAc-Sp0 | 595 | 285 | 142 | 48 |
| 24 | (Galβ1-4GlcNAcβ)2-3,6-GalNAcα-Sp8 | 590 | 240 | 120 | 41 |
| 223 | NeuAcα2-3Galβ1-3GalNAcβ1-3Galα1-4Galβ1-4Glcβ-Sp0 | 580 | 191 | 95 | 33 |
| 162 | GlcNAcβ1-3Galβ-Sp8 | 577 | 435 | 217 | 75 |
| 135 | Galβ1-4(Fucα1-3)GlcNAcβ-Sp0 | 561 | 139 | 70 | 25 |
| 249 | Neu5Acα2-6Galβ1-4Glcβ-Sp0 | 560 | 377 | 189 | 67 |

-continued

| Glycan number | Glycan name | Avg w/o Max & Min | StDev w/o Max & Min | SEM w/o Max & Min | % CV |
|---|---|---|---|---|---|
| 48 | 9NAcNeu5Acα-Sp8 | 556 | 470 | 235 | 85 |
| 158 | GlcNAcβ1-2Galβ1-3GalNAcα-Sp8 | 550 | 417 | 208 | 76 |
| 264 | Neu5Gcα-Sp8 | 550 | 305 | 152 | 55 |
| 46 | NeuAcα2-3[6OSO3]Galβ1-4GlcNAcβ-Sp8 | 545 | 363 | 182 | 67 |
| 68 | Fucα1-2Galβ1-4(Fucα1-3)GlcNAcβ-Sp8 | 541 | 208 | 104 | 38 |
| 222 | Neu5Acα2-3Galβ-Sp8 | 526 | 277 | 139 | 53 |
| 298 | Galβ1-4GlcNAcα1-6Galβ1-4GlcNAcβ-Sp0 | 494 | 335 | 167 | 68 |
| 98 | Galα1-3(Fucα1-2)Galβ1-4Glcβ-Sp0 | 482 | 112 | 56 | 23 |
| 312 | Manα1-6(Manα1-3)Manα1-6(Manα1-3)Manβ-Sp10 | 453 | 292 | 146 | 64 |
| 133 | Galβ1-3GlcNAcβ-Sp0 | 452 | 165 | 82 | 36 |
| 57 | Fucα1-2Galβ1-3(Fucα1-4)GlcNAcβ-Sp8 | 450 | 268 | 134 | 60 |
| 114 | Galβ1-2Galβ-Sp8 | 449 | 324 | 162 | 72 |
| 198 | Manα1-6(Manα1-3)Manα1-6(Manα1-3)Manβ1-4GlcNAcβ1-4GlcNAcβ-Sp12 | 448 | 204 | 102 | 45 |
| 161 | GlcNAcβ1-3GalNAcα-Sp8 | 442 | 156 | 78 | 35 |
| 281 | Galβ1-4[Fucα1-3][6OSO3]Glc-Sp0 | 439 | 144 | 72 | 33 |
| 259 | Neu5Gcα2-3Galβ1-4(Fucα1-3)GlcNAcβ-Sp0 | 433 | 357 | 179 | 83 |
| 67 | Fucα1-2Galβ1-4(Fucα1-3)GlcNAcβ-Sp0 | 420 | 94 | 47 | 22 |
| 12 | α-L-Fuc-Sp9 | 410 | 303 | 151 | 74 |
| 159 | GlcNAcβ1-3(GlcNAcβ1-6)GalNAcα-Sp8 | 407 | 88 | 44 | 22 |
| 75 | Fucα1-3GlcNAcβ-Sp8 | 399 | 182 | 91 | 46 |
| 239 | Neu5Acα2-3Galβ1-4Glcβ-Sp0 | 395 | 156 | 78 | 39 |
| 290 | Galα1-3(Fucα1-2)Galβ-Sp18 | 389 | 246 | 123 | 63 |
| 11 | α-L-Fuc-Sp8 | 387 | 231 | 115 | 60 |
| 51 | GlcNAcβ1-2Manα1-3(GlcNAcβ1-2Manα1-6)Manβ1-4GlcNAcβ1-4GlcNAcβ-Sp13 | 383 | 164 | 82 | 43 |
| 5 | Galβ1-3GlcNAcβ1-2Manα1-3(Galβ1-3GlcNAcβ1-2Manα1-6)Manβ1-4GlcNAcβ1-4GlcNAcβ-Sp19 | 381 | 529 | 265 | 139 |
| 63 | Fucα1-2Galβ1-3GlcNAcβ-Sp0 | 362 | 187 | 93 | 52 |
| 241 | Galβ1-4GlcNAcβ1-2Manα1-3(Fucα1-3(Galβ1-4)GlcNAcβ1-2Manα1-6)Manβ1-4GlcNAcβ1-4GlcNAcβ-Sp20 | 352 | 68 | 34 | 19 |
| 155 | Galβ1-4Glcβ-Sp8 | 315 | 105 | 53 | 33 |
| 126 | Galβ1-3GalNAcβ-Sp8 | 288 | 265 | 132 | 92 |
| 195 | Manα1-3(Manα1-6)Manα-Sp9 | 269 | 92 | 46 | 34 |
| 88 | GalNAcβ1-3GalNAcα-Sp8 | 262 | 107 | 54 | 41 |
| 252 | Neu5Acα2-8Neu5Acα-Sp8 | 260 | 214 | 107 | 82 |
| 167 | GlcNAcβ1-3Galβ1-4Glcβ-Sp0 | 257 | 129 | 64 | 50 |
| 140 | Galβ1-4Ξ6OSO3]Glcβ-Sp8 | 256 | 345 | 172 | 135 |
| 177 | Glcα1-4Glcβ-Sp8 | 246 | 113 | 57 | 46 |
| 179 | Glcα1-6Glcα1-6Glcβ-Sp8 | 225 | 380 | 190 | 168 |
| 314 | Manα1-2Manα1-2Manα1-3(Manα1-2Manα1-6(Manα1-2Manα1-3)Manα1-6)Manα-Sp9 | 221 | 329 | 165 | 149 |
| 238 | Neu5Acα2-3Galβ1-4GlcNAcβ1-3Galβ1-4GlcNAcβ-Sp0 | 212 | 200 | 100 | 94 |
| 220 | Neu5Acα2-3Galβ1-3[6OSO3]GalNAcα-Sp8 | 210 | 153 | 77 | 73 |
| 142 | Galβ1-4GalNAcβ1-3(Fucα1-2)Galβ1-4GlcNAcβ-Sp8 | 204 | 126 | 63 | 62 |
| 61 | Fucα1-2Galβ1-3GlcNAcβ1-3Galβ1-4Glcβ-Sp10 | 196 | 67 | 34 | 34 |
| 102 | Galα1-3GalNAcβ-Sp8 | 188 | 198 | 99 | 105 |
| 170 | GlcNAcβ1-4Galβ1-4GlcNAcβ-Sp8 | 184 | 127 | 64 | 69 |
| 124 | Galβ1-3(Neu5Acα2-6)GlcNAcβ1-4Galβ1-4Glcβ-Sp10 | 173 | 146 | 73 | 84 |
| 100 | Galα1-3(Galα1-4)Galβ1-4GlcNAcβ-Sp8 | 168 | 112 | 56 | 66 |
| 186 | GlcAβ1-6Galβ-Sp8 | 158 | 171 | 86 | 108 |
| 4 | Neu5Gcβ2-6Galβ1-4GlcNAc-Sp8 | 152 | 96 | 48 | 63 |
| 73 | Fucα1-2Galβ1-4Glcβ-Sp0 | 148 | 205 | 103 | 139 |
| 49 | 9NAcNeu5Acα2-6Galβ1-4GlcNAcβ-Sp8 | 146 | 159 | 79 | 108 |
| 58 | Fucα1-2Galβ1-3GalNAcα-Sp8 | 136 | 171 | 86 | 126 |
| 250 | Neu5Acα2-6Galβ1-4Glcβ-Sp8 | 122 | 144 | 72 | 119 |
| 112 | Galα1-4GlcNAcβ-Sp8 | 115 | 82 | 41 | 72 |
| 165 | GlcNAcβ1-3Galβ1-4GlcNAcβ-Sp8 | 84 | 68 | 34 | 81 |
| 226 | Neu5Acα2-3Galβ1-3GlcNAcβ-Sp8 | 76 | 85 | 42 | 112 |
| 288 | [6OSO3]Galβ1-4[6OSO3]GlcNacβ-Sp0 | 72 | 130 | 65 | 180 |
| 153 | Galβ1-4GlcNAcβ-Sp8 | 48 | 58 | 29 | 120 |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. C. G. Figdor, Y. van Kooyk, G. J. Adema, Nat Rev Immunol 2, 77 (February, 2002).
2. E. Pyz, A. S. Marshall, S. Gordon, G. D. Brown, Ann Med 38, 242 (2006).
3. G. D. Brown, Nat Rev Immunol 6, 33 (January, 2006).
4. T. B. Geijtenbeek et al., Nat Immunol 1, 353 (October, 2000).
5. T. B. Geijtenbeek et al., Cell 100, 575 (Mar. 3, 2000).
6. C. F. d'Ostiani et al., J Exp Med 191, 1661 (May 15, 2000).
7. C. Fradin, D. Poulain, T. Jouault, Infect Immun 68, 4391 (August, 2000).
8. A. Cambi et al., Eur J Immunol 33, 532 (February, 2003).
9. M. G. Netea, J. W. Meer, I. Verschueren, B. J. Kullberg, Eur J Immunol 32, 1455 (May, 2002).
10. S. J. Lee et al., Science 295, 1898 (Mar. 8, 2002).
11. N. Maeda et al., J Biol Chem 278, 5513 (Feb. 21, 2003).
12. L. Tailleux et al., J Exp Med 197, 121 (Jan. 6, 2003).
13. T. B. Geijtenbeek et al., J Exp Med 197, 7 (Jan. 6, 2003).
14. A. M. Cooper et al., J Immunol 168, 1322 (Feb. 1, 2002).
15. J. Banchereau et al., Annu Rev Immunol 18, 767 (2000).
16. P. Jeannin et al., Immunity 22, 551 (May, 2005).
17. B. N. Gantner, R. M. Simmons, S. J. Canavera, S. Akira, D. M. Underhill, J Exp Med 197, 1107 (May 5, 2003).
18. H. Moriwaki et al., FEBS Lett 440, 29 (Nov. 27, 1998).
19. M. Wykes, G. MacPherson, Immunology 100, 1 (May, 2000).
20. M. Balazs, F. Martin, T. Zhou, J. Kearney, Immunity 17, 341 (September, 2002).
21. T. Kikuchi, S. Worgall, R. Singh, M. A. Moore, R. G. Crystal, Nat Med 6, 1154 (October, 2000).
22. B. Dubois et al., J Leukoc Biol 66, 224 (August, 1999).
23. H. Qi, J. G. Egen, A. Y. Huang, R. N. Germain, Science 312, 1672 (Jun. 16, 2006).
24. A. Bergtold, D. D. Desai, A. Gavhane, R. Clynes, Immunity 23, 503 (November, 2005).
25. C. R. Ruprecht, A. Lanzavecchia, Eur J Immunol 36, 810 (April, 2006).
26. N. L. Bernasconi, E. Traggiai, A. Lanzavecchia, Science 298, 2199 (Dec. 13, 2002).
27. P. A. Moore et al., Science 285, 260 (Jul. 9, 1999).
28. J. A. Gross et al., Nature 404, 995 (Apr. 27, 2000).
29. A. Craxton, D. Magaletti, E. J. Ryan, E. A. Clark, Blood 101, 4464 (Jun. 1, 2003).
30. I. MacLennan, C. Vinuesa, Immunity 17, 235 (September, 2002).
31. J. Banchereau, R. M. Steinman, Nature 392, 245 (Mar. 19, 1998).
32. J. Banchereau, P. de Paoli, A. Valle, E. Garcia, F. Rousset, Science 251, 70 (Jan. 4, 1991).
33. B. Beutler et al., Annu Rev Immunol 24, 353 (2006).
34. K. Hayashida, N. Kume, M. Minami, T. Kita, FEBS Lett 511, 133 (Jan. 30, 2002).
35. M. Kakutani, T. Masaki, T. Sawamura, Proc Natl Acad Sci USA 97, 360 (Jan. 4, 2000).
36. M. Colonna, J. Samaridis, L. Angman, Eur J Immunol 30, 697 (February, 2000).
37. J. Valladeau et al., J Immunol 167, 5767 (Nov. 15, 2001).
38. G. Jego et al., Immunity 19, 225 (August, 2003).
39. M. N. Wykes, L. Beattie, G. G. Macpherson, D. N. Hart, Immunology 113, 318 (November, 2004).
40. Y. Delneste et al., Immunity 17, 353 (September, 2002).
41. Y. Wang et al., Immunity 15, 971 (December, 2001).
42. A. Asea et al., Nat Med 6, 435 (April, 2000).
43. H. Bausinger et al., Eur J Immunol 32, 3708 (December, 2002).
44. E. E. Bates et al., J Immunol 163, 1973 (Aug. 15, 1999).

What is claimed is:

1. A method of delivering an antigen to an antigen presenting cell, comprising administering to the antigen presenting cell an effective amount of a composition comprising a recombinant fusion protein, said fusion protein comprising an anti-human dendritic cell asialoglycoprotein receptor (ASGPR) antibody or an antigen binding fragment thereof and one or more autoimmune antigens, wherein the antibody or fragment thereof comprises (a) an immunoglobulin heavy chain selected from the group consisting of SEQ ID NO: 5, 7, 9, and 11; and (b) an immunoglobulin light chain selected from the group consisting of SEQ ID NO: 6, 8, 10, and 12.

2. The method of claim 1, wherein the antigen is Smith protein, RNP ribonucleoprotein, SS-A protein, SS-B protein, acetylcholine receptor, luteinizing hormone, follicular stimulating hormone, testosterone, growth hormone, prolactin, glutamic acid decarboxylase 65 (GAD 65), myelin basic protein, myelin proteolipid protein, thyroglobulin, or thyroid stimulating hormone (TSH) receptor.

3. The method of claim 2, wherein the antigen is myelin basic protein.

4. The method of claim 1, wherein the antigen presenting cell is a dendritic cell.

5. The method of claim 1, wherein the antibody or fragment thereof comprises SEQ ID NO: 7 and SEQ ID NO: 8.

6. The method of claim 1, wherein the antibody or fragment thereof comprises SEQ ID NO: 9 and SEQ ID NO: 10.

7. The method of claim 1, wherein the antibody or fragment thereof comprises SEQ ID NO: 11 and SEQ ID NO: 12.

* * * * *